US009862739B2

(12) United States Patent
Metz et al.

(10) Patent No.: US 9,862,739 B2
(45) Date of Patent: Jan. 9, 2018

(54) METAL COMPLEXES, COMPRISING CARBENE LIGANDS HAVING AN O-SUBSTITUTED NON-CYCLOMETALATED ARYL GROUP AND THEIR USE IN ORGANIC LIGHT EMITTING DIODES

(71) Applicant: UDC IRELAND LIMITED, Dublin (IE)

(72) Inventors: Stefan Metz, Mannheim (DE); Korinna Dormann, Bad Durkheim (DE); Glauco Battagliarin, Mannheim (DE); Christian Eickhoff, Mannheim (DE); Flavio Luiz Benedito, Ludwigshafen (DE); Soichi Watanabe, Ludwigshafen (DE); Gerhard Wagenblast, Wachenheim (DE); Thomas Geβner, Heidelberg (DE); Christian Lennartz, Schifferstadt (DE); Peter Murer, Oberwil (CH)

(73) Assignee: UDC Ireland Limited, Dublin (IE)

( * ) Notice: Subject to any disclaimer, the term of this patent is extended or adjusted under 35 U.S.C. 154(b) by 0 days.

(21) Appl. No.: 15/300,582

(22) PCT Filed: Mar. 26, 2015

(86) PCT No.: PCT/EP2015/056491
§ 371 (c)(1),
(2) Date: Sep. 29, 2016

(87) PCT Pub. No.: WO2015/150203
PCT Pub. Date: Oct. 8, 2015

(65) Prior Publication Data
US 2017/0183367 A1 Jun. 29, 2017

(30) Foreign Application Priority Data

Mar. 31, 2014 (EP) .................... 14162805

(51) Int. Cl.
*C07F 15/00* (2006.01)
*H01L 51/50* (2006.01)
*H01L 51/00* (2006.01)
*C09K 11/06* (2006.01)

(52) U.S. Cl.
CPC .......... *C07F 15/0033* (2013.01); *C09K 11/06* (2013.01); *H01L 51/0085* (2013.01)

(58) Field of Classification Search
CPC ................ C07F 15/00; H01L 51/50
USPC ............ 546/10; 544/225; 548/108; 313/504
See application file for complete search history.

(56) References Cited

U.S. PATENT DOCUMENTS

2001/0015432 A1 8/2001 Igarashi
2001/0019782 A1 9/2001 Igarashi et al.
2002/0024293 A1 2/2002 Igarashi et al.
2002/0048689 A1 4/2002 Igarashi et al.
2002/0055014 A1 5/2002 Okada et al.
2002/0094453 A1 7/2002 Takiguchi et al.
2007/0224446 A1 9/2007 Nakano et al.
2009/0066226 A1 3/2009 Sugita et al.
2009/0153034 A1 6/2009 Lin et al.
2009/0284138 A1 11/2009 Yasukawa et al.
2011/0057559 A1 3/2011 Xin et al.
2011/0233528 A1 9/2011 Levermore et al.
2011/0266528 A1 11/2011 Langer et al.
2012/0261654 A1 10/2012 Yasukawa et al.
2012/0305894 A1 12/2012 Kim et al.
2013/0032766 A1* 2/2013 Molt .................. C07F 15/0033
                                                        252/519.2

FOREIGN PATENT DOCUMENTS

| EP | 1191612 | 3/2002 |
|---|---|---|
| EP | 1191613 | 3/2002 |
| EP | 1211257 | 6/2002 |
| EP | 1786050 | 5/2007 |
| EP | 1837926 | 9/2007 |
| EP | 1885818 | 2/2008 |
| EP | 1970976 | 9/2008 |
| EP | 1998388 | 12/2008 |
| EP | 09153776.1 | 2/2009 |

(Continued)

OTHER PUBLICATIONS

U.S. Appl. No. 61/669,677, filed Jul. 10, 2012, Shaefer et al.
Baldo et al., "Very high-efficiency green organic light-emitting devices based on electrophosphorescence," Appl. Phys. Lett., vol. 75, No. 1, 4-6 (1999).
Gao and Kahn, "Controlled p doping of the hole-transport molecular material N,N'-diphenyl-N,N'-bis(1-naphthyl)-1,1'-biphenyl-4,4'-diamine with tetrafluorotetracyanoquinodimethane," 2003, J. Appl. Phys. 94:359-366.

(Continued)

*Primary Examiner* — Charanjit Aulakh
(74) *Attorney, Agent, or Firm* — Riverside Law LLP

(57) ABSTRACT

Cyclometallated Ir complex comprising three N,N diaryl substituted carbene ligands, bearing substituents in the 2 position of the non-cyclometallated aryl ring; an organic electronic device, preferably an organic light-emitting diode (OLED), comprising at least one cyclometallated Ir complex as described above, a light-emitting layer comprising said cyclometallated Ir complex preferably as emitter material, preferably in combination with at least one host material, use of said cyclometallated Ir complex in an OLED and an apparatus selected from the group consisting of stationary visual display units, mobile visual display units, illumination units, units in items of clothing, units in handbags, units in accessories, units in furniture and units in wallpaper comprising said organic electronic device, preferably said OLED, or said light-emitting layer. The present invention further relates to a process for the preparation of said cyclometallated Ir complex.

17 Claims, No Drawings

(56) References Cited

FOREIGN PATENT DOCUMENTS

| | | |
|---|---|---|
| EP | 2034538 | 3/2009 |
| EP | 2180029 | 4/2010 |
| EP | 12175635.7 | 7/2012 |
| EP | 12185230.5 | 9/2012 |
| EP | 12191408.9 | 11/2012 |
| EP | 2551932 | 1/2013 |
| EP | 13160198.1 | 3/2013 |
| EP | 13178678.8 | 7/2013 |
| JP | 2008021687 | 1/2008 |
| JP | 2008066569 | 3/2008 |
| JP | 2008074939 | 4/2008 |
| JP | 2008084913 | 4/2008 |
| JP | 2008127326 | 6/2008 |
| JP | 2008207520 | 9/2008 |
| JP | 2009021336 | 1/2009 |
| JP | 2009059767 | 3/2009 |
| JP | 2009114369 | 5/2009 |
| JP | 2009114370 | 5/2009 |
| JP | 2009135183 | 6/2009 |
| JP | 2009170764 | 7/2009 |
| JP | 2009182298 | 8/2009 |
| JP | 2009267255 | 11/2009 |
| JP | 2010021336 | 1/2010 |
| JP | 2010040830 | 2/2010 |
| JP | 2010114180 | 5/2010 |
| JP | 2010135467 | 6/2010 |
| WO | 0070655 | 11/2000 |
| WO | 0141512 | 6/2001 |
| WO | 0202714 | 1/2002 |
| WO | 0215645 | 2/2002 |
| WO | 02060910 | 8/2002 |
| WO | 2005019373 | 3/2005 |
| WO | 2005113704 | 12/2005 |
| WO | 2006056418 | 6/2006 |
| WO | 2006067074 | 6/2006 |
| WO | 2006115301 | 11/2006 |
| WO | 2006121811 | 11/2006 |
| WO | 2006128800 | 12/2006 |
| WO | 2007077810 | 7/2007 |
| WO | 2007095118 | 8/2007 |
| WO | 2007114244 | 10/2007 |
| WO | 2007115970 | 10/2007 |
| WO | 2007115981 | 10/2007 |
| WO | 2007119816 | 10/2007 |
| WO | 2008000727 | 1/2008 |
| WO | 2008029652 | 3/2008 |
| WO | 2008029729 | 3/2008 |
| WO | 2008034758 | 3/2008 |
| WO | 2008035571 | 3/2008 |
| WO | 2008156105 | 12/2008 |
| WO | 2008156879 | 12/2008 |
| WO | 2009003898 | 1/2009 |
| WO | 2009003919 | 1/2009 |
| WO | 2009008099 | 1/2009 |
| WO | 2009008100 | 1/2009 |
| WO | 2009050281 | 4/2009 |
| WO | 2009050290 | 4/2009 |
| WO | 2009060742 | 5/2009 |
| WO | 2009060757 | 5/2009 |
| WO | 2009060779 | 5/2009 |
| WO | 2009060780 | 5/2009 |
| WO | 2009063757 | 5/2009 |
| WO | 2009084413 | 7/2009 |
| WO | 2009086028 | 7/2009 |
| WO | 2007108362 | 8/2009 |
| WO | 2007108459 | 8/2009 |
| WO | 2009104488 | 8/2009 |
| WO | 2010001830 | 1/2010 |
| WO | 2010004877 | 1/2010 |
| WO | 2008072596 | 3/2010 |
| WO | 2010040777 | 4/2010 |
| WO | 2010044342 | 4/2010 |
| WO | 2008090912 | 5/2010 |
| WO | 2010067746 | 6/2010 |
| WO | 2010068876 | 6/2010 |
| WO | 2010079051 | 7/2010 |
| WO | 2010079678 | 7/2010 |
| WO | 2008146838 | 8/2010 |
| WO | 2010086089 | 8/2010 |
| WO | 2010087222 | 8/2010 |
| WO | 2010090077 | 8/2010 |
| WO | 2010095564 | 8/2010 |
| WO | 2011004639 | 1/2011 |
| WO | 2011051404 | 5/2011 |
| WO | 2011073149 | 6/2011 |
| WO | 2011106344 | 9/2011 |
| WO | 2011157339 | 12/2011 |
| WO | 2011157779 | 12/2011 |
| WO | 2011157790 | 12/2011 |
| WO | 2012014621 | 2/2012 |
| WO | 2012048226 | 4/2012 |
| WO | 2012105310 | 8/2012 |
| WO | 2012115034 | 8/2012 |
| WO | 2012121936 | 9/2012 |
| WO | 2012130709 | 10/2012 |
| WO | 2012145173 | 10/2012 |
| WO | 2012147397 | 11/2012 |
| WO | 2012162325 | 11/2012 |
| WO | 2012162625 | 11/2012 |
| WO | 2012170461 | 12/2012 |
| WO | 2012170463 | 12/2012 |
| WO | 2012170571 | 12/2012 |
| WO | 2012172182 | 12/2012 |
| WO | 2012172482 | 12/2012 |
| WO | 2013031662 | 3/2013 |
| WO | 2013031794 | 3/2013 |
| WO | 2014044722 | 3/2014 |
| WO | 2014072320 | 5/2014 |
| WO | 2014147134 | 9/2014 |
| WO | 2015014835 | 2/2015 |

OTHER PUBLICATIONS

Werner et al., "Pyronin B as a donor for n-type doping of organic thin films," 2003, Appl. Phys. Lett. 82:4495-4497.

Pfeiffer et al., "Doped organic semiconductors: Physics and application in light emitting diodes", 2003, Organic Electronics 4:89-103.

Walzer et al., "Highly Efficient Organic Devices Based on Electrically Doped Transport Layers", 2007, Chem. Soc. Rev. 107:1233-1271.

Kahn et al., "Use of a High Electron-Affinity Molybdenum Dithiolene Complex to p-Dope Hole-Transport Layers", 2009, J. Am. Chem. Soc. 131:12530-12531.

Kido et al., "2-Phenylpyrimidine skeleton-based electron-transport materials for extremely efficient green organic light-emitting devices", 2008, Chem. Commun. 5821-5823.

Kido et al., "Wide-Energy-Gap Electron-Transport Materials Containing 3,5-Dipyridylphenyl Moieties for an Ultra High Efficiency Blue Organic Light-Emitting Device", 2008, Chem. Mater. 20:5951-5953.

\* cited by examiner

METAL COMPLEXES, COMPRISING CARBENE LIGANDS HAVING AN O-SUBSTITUTED NON-CYCLOMETALATED ARYL GROUP AND THEIR USE IN ORGANIC LIGHT EMITTING DIODES

CROSS-REFERENCE TO RELATED APPLICATIONS

The present application is a 35 U.S.C. §371 national stage patent application of International Patent Application No. PCT/EP2015/056491, filed on Mar. 26, 2015, and which claims priority to European Patent Application No. 14162085.7, filed on Mar. 31, 2014, all of which applications are incorporated by reference herein in their entireties.

The present invention relates to a cyclometallated Ir complex comprising three N,N diaryl substituted carbene ligands, bearing substituents in the 2 position of the non-cyclometallated aryl ring; an organic electronic device, preferably an organic light-emitting diode (OLED), comprising at least one cyclometallated Ir complex as described above, to a light-emitting layer comprising said cyclometallated Ir complex preferably as emitter material, preferably in combination with at least one host material, to the use of said cyclometallated Ir complex in an OLED and to an apparatus selected from the group consisting of stationary visual display units, mobile visual display units, illumination units, units in items of clothing, units in handbags, units in accessories, units in furniture and units in wallpaper comprising said organic electronic device, preferably said OLED, or said light-emitting layer. The present invention further relates to a process for the preparation of said cyclometallated Ir complex.

Organic electronics, i.e. organic electronic devices, are an important sector in the field of electronics. Organic electronics is a subfield of electronics which uses electronic circuits which comprise polymers or smaller organic compounds. Fields of use of organic electronics are the use of polymers or smaller organic compounds in organic electronic devices, for example in organic light-emitting diodes (OLED), light-emitting electrochemical cells (LEEC), organic photovoltaic cells (OPV) and organic field-effect transistors (OFET).

The use of suitable novel organic materials thus allows various new types of components based on organic electronics to be provided, such as displays, illumination, sensors, transistors, data stores or photovoltaic cells. This makes possible the development of new devices which are thin, light, flexible and producible at low cost.

The synthesis and provision of new materials for organic electronic devices is therefore an important research topic. Especially the synthesis and provision of dyes for use in organic electronic devices (useful for example as emitter materials in OLEDs and LEECs or as absorption dyes in OPVs) is important for providing organic electronic devices having good stabilities and long lifetimes as well as—in the case of OLEDs and LEECs—high quantum efficiencies.

A preferred field of use according to the present application is the use of relatively small organic compounds in organic light-emitting diodes (OLED). OLEDs exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cell-phones, smartphones, digital cameras, mp3 players, tablet computers, laptops, etc. In addition, white OLEDs give great advantage over the illumination technologies known to date, especially a particularly high efficiency.

The basic principles of the way in which OLEDs work and suitable structures (layers) of OLEDs are specified, for example, in WO 2005/113704 and the literature cited therein.

The light-emitting materials (emitters) used may be phosphorescent materials (phosphorescent emitters) as well as fluorescent materials (fluorescent emitters). The phosphorescent emitters are typically organometallic complexes which exhibit triplet emission in contrast to the fluorescent emitters which exhibit singlet emission (M. A. Baldow et al., Appl. Phys. Lett. 1999, 75, 4 to 6). For quantum-mechanical reasons up to four times the quantum efficiency, energy efficiency and power efficiency achieved with fluorescent emitters is possible when phosphorescent emitters are used.

Of particular interest are organic light-emitting diodes with a good color purity, low operational voltage, high efficiency, high efficacy, high resistance to thermal stress and long operational lifetime.

In order to implement the aforementioned properties in practice, it is necessary to provide suitable emitter materials. The selection of suitable emitter materials has a significant influence on parameters including the color purity, efficiency, lifetime and operating voltages of the OLEDs.

One important class of compounds useful in organic electronic devices, especially in OLEDs, preferably as phosphorescent emitters are cyclometallated transition metal carbene complexes. Such complexes are described for example in WO 2006/056418 A2, WO 2005/113704, WO 2007/115970, WO 2007/115981, WO 2008/000727, WO2009/050281, WO2009/050290, WO2011/051404, US2011/057559 WO2011/073149, WO2012/121936A2, US2012/0305894A1, WO2012/170571, WO2012/170461, WO 2012/170463, WO2006/121811, WO2007/095118, WO2008/156879, WO2008/156879, WO2010/068876, US2011/0057559, WO2011/106344, US2011/0233528, WO2012/048266 and WO2012/172482.

The cyclometallated transition metal carbene complexes according to the prior art mentioned above having the general formula $MA_3B_3$ may be present in form of their in many cases not isolatable meridional (mer) isomers and/or in form of their usually thermodynamically preferred facial (fac) isomers, both having different physical properties.

According to the present application, meridional and facial isomers of octahedral transition metal complexes are defined as follows:

In the case of complexes of the composition $MA_3B_3$, three groups of the same type can occupy either the corners of one face of the octahedron (facial isomer (fac isomer)) or a meridian, i.e. two of the three ligand bonding points are in trans positions relative to one another (meridional isomer (mer isomer)). For the definition of fac/mer isomers in octahedral metal complexes see, for example, J. Huheey, E. Keiter, R. Keiter, Anorganische Chemie: Prinzipien von Struktur and Reaktivitat, 2nd, revised edition, translated and expanded by Ralf Steudel, Berlin; New York: de Gruyter, 1995, pages 575, 576.

It is shown in the prior art mentioned above that in the case of carbene complexes comprising N-alkyl, N-aryl substituted carbene ligands, the mer isomer is formed predominantly which can be transformed into the thermodynamically preferred fac isomer. However, in the case of carbene complexes consisting of diaryl substituted carbene ligands the thermodynamically preferred fac isomer is usually formed predominantly.

According to the prior art mentioned above, transition metal complexes bearing carbene ligands are usually prepared according to one of the following three routes:
i) Deprotonation of (aza)benzimidazolium salts;
ii) Transmetallation of silver carbenes;
iii) Producing a carbene starting from the corresponding alkoxy derivative.

However, independently from the method used, in the case of asymmetric diaryl substituted carbene ligands, wherein both aryl residues are in general suitable for a cyclometallation with the central metal, it is not possible to influence the cyclometallation in order to achieve only one cyclometallation isomer of the carbene complex. The separation of the isomers is accompanied by a loss of material associated with low yields.

US 2012/0305894 A1 relates to a blue phosphorescent compound with high color purity and a high efficiency and an organic electroluminescent device using the same. The blue phosphorecent compound mentioned in the example according to US 2012/0305894 A1 is characterized by the following formula:

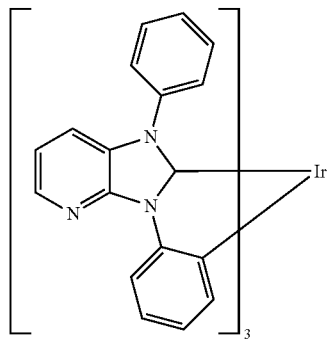

It is mentioned that the Ir complex shown above is obtained as a major isomer. However, it is not mentioned in US 2012/0305894 A1 how the formation of cyclometallation isomers may be avoided. Further, fac and mer isomers of the compounds described in US 2012/0305894 A1 are not mentioned.

WO 2012/121936 A2 discloses organometallic compounds comprising an imidazole carbene ligand having an N-containing ring fused to the imidazole ring. In particular, the N-containing ring fused to the imidazole ring may contain one nitrogen atom or more than one nitrogen atom. These materials are—according to WO 2012/121936 A2—useful as blue phosphorescent emitters for OLEDs.

WO 2011/073149 A1 relates to metal-carbene complexes comprising a central atom selected from iridium and platinum, and diazabenzimidazol carbene-ligands, to organic light-emitting diodes comprising said complexes, to light-emitting layers comprising at least one such metal-carbene complex, to a device selected from the group comprising lighting elements, stationary screens and mobile screens comprising such an OLED, and to the use of such a metal-carbene complex in OLEDs, for example as an emitter, matrix material, charge transport material, and/or charge or exciton blocker.

WO 2012/172482 A1 relates to metal-carbene complexes comprising a central atom selected from iridium and platinum, and specific azabenzimidazolocarbeneligands, to OLEDs (Organic Light Emitting Diode, OLED) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker. It is further clear from said document that mer isomers could only be obtained in the case of carbene complexes comprising N-alkyl, N-aryl substituted carbene ligands, while the examples disclosed concerning carbene complexes comprising diaryl substituted carbene ligands yield fac isomers.

The three documents, WO 2011/073149 A1, WO 2011/073149 A1 and WO 2012/172482 A1 disclose a number of carbene complexes comprising N-alkyl, N-aryl substituted carbene ligands. In such carbene complexes only one cyclometallation isomer is present.

It is an object of the present invention to provide metal-carbene complexes having aryl substituted carbene ligands only or mainly in form of their mer isomer. It is a further object of the present invention to provide metal carbene complexes having diaryl substituted carbene ligands in form of only one or mainly one cyclometallation isomer.

Said metal-carbene complexes having diaryl substituted carbene ligands are suitable for use in organic light-emitting diodes with a good color purity, low operational voltage, high efficiency, high efficacy, high resistance to thermal stress and especially long operational lifetime.

It has surprisingly been found by the inventors of the present application that the mer isomer of metal-carbene complexes having diaryl substituted carbene ligands usually shows significantly shorter emission decay times than the corresponding fac isomer. Thus, the radiative processes can better compete with the non-radiative ones. Consequently, metal-carbene complexes of the present invention, especially the mer isomers, exhibit efficient emissions and therefore are well suited as emitter materials for OLEDs with long operational lifetime.

It is now possible to isolate mer isomers of metal-carbene complexes having diaryl substituted carbene ligands exclusively or as main isomers.

Since only one or mainly one cyclometallation isomer is present, the separation of the isomers which is usually accompanied by a loss of material associated with low yields is in many cases not necessary.

This object is achieved by a cyclometallated Ir complex of formula (I)

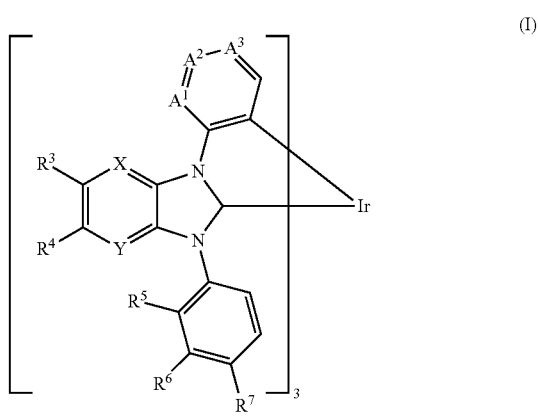

wherein
A¹ is CH or N;
A² is CR¹ or N;
A³ is CR² or N;
wherein in the case that A¹ and/or A³ are N, A² is CR¹;
R¹, R², R³, R⁴, R⁶ and R⁷
are each independently hydrogen; deuterium; a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, R¹, R², R³, R⁴, R⁶ and R⁷ are each independently hydrogen, deuterium, a linear or branched, substituted or unsubstituted alkyl radical, having from 1 to 6 carbon atoms; a substituted or unsubstituted cycloalkyl radical having a total of from 3 to 12 carbon atoms; an unsubstituted aryl radical, having from 6 to 12 carbon atoms, a monosubstituted aryl radical having from 6 to 18 carbon atoms, a disubstituted aryl radical having from 6 to 18 carbon atoms; an unsubstituted heteroaryl radical, having a total of from 5 to 16 carbon atoms and/or heteroatoms, a monosubstituted heteroaryl radical, having a total of from 5 to 18 carbon atoms and/or heteroatoms, a disubstituted heteroaryl radical, having a total of from 5 to 20 carbon atoms and/or heteroatoms; more preferably, the aryl radical or heteroaryl radical are selected from the group consisting of phenyl, pyridyl, primidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, cyclopentyl, cyclohexyl, methoxy, phenyl or $CF_3$; a group with donor or acceptor action, selected from OPh, halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$;
R¹⁰, R¹¹, R¹²
are each independently a linear or branched alkyl radical, having from 1 to 6 carbon atoms, preferably methyl, ethyl, n-propyl, iso-propyl, n-butyl, tert-butyl, sec-butyl or iso-butyl; a substituted or unsubstituted aryl radical, having from 6 to 12 carbon atoms, preferably phenyl or tolyl; a substituted or unsubstituted heteroaryl radical, having a total of from 5 to 15 carbon atoms and/or heteroatoms; a substituted or unsubstituted cycloalkyl radical having a total of from 3 to 7 carbon atoms, preferably cyclopentyl or cyclohexyl;
or
R¹ and R², R³ and R⁴ and/or R⁶ and R⁷ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms;

R⁵
is a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action;
preferably, R⁵ is a linear or branched, substituted or unsubstituted alkyl radical, having from 1 to 6 carbon atoms; a substituted or unsubstituted cycloalkyl radical having a total of from 3 to 12 carbon atoms; an unsubstituted aryl radical, having from 6 to 12 carbon atoms, a monosubstituted aryl radical having from 6 to 18 carbon atoms, a disubstituted aryl radical having from 6 to 18 carbon atoms; an unsubstituted heteroaryl radical, having a total of from 5 to 16 carbon atoms and/or heteroatoms, a monosubstituted heteroaryl radical, having a total of from 5 to 18 carbon atoms and/or heteroatoms, a disubstituted heteroaryl radical, having a total of from 5 to 20 carbon atoms and/or heteroatoms; more preferably, the aryl radical or heteroaryl radical are selected from the group consisting of phenyl, pyridyl, primidyl, pyrazinyl, carbazolyl, dibenzofuranyl, dibenzothiophenyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, cyclopentyl, cyclohexyl, methoxy, phenyl, $CF_3$ or CN; a group with donor or acceptor action, selected from $CF_3$, CN; or $SiR^{10}R^{11}R^{12}$, preferably $SiMe_3$, $SiPh_3$, $SiEt_3$ or $SiPh_2tBu$;
X is CH, CD or N;
Y is CR⁸ or N;
R⁸
is hydrogen; deuterium; a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, R⁸ is hydrogen, deuterium, a linear or branched, substituted or unsubstituted alkyl radical, having from 1 to 6 carbon atoms; a substituted or unsubstituted cycloalkyl radical having a total of from 3 to 12 carbon atoms; an unsubstituted aryl radical, having from 6 to 12 carbon atoms, a monosubstituted aryl radical having from 6 to 18 carbon atoms, a disubstituted aryl radical having from 6 to 18 carbon atoms; an unsubstituted heteroaryl radical, having a total of from 5 to 16 carbon atoms and/or heteroatoms, a monosubstituted heteroaryl radical, having a total of from 5 to 18 carbon atoms and/or heteroatoms, a disubstituted heteroaryl radical, having a total of from 5 to 20 carbon atoms and/or heteroatoms; more preferably, the aryl radical or heteroaryl radical are selected from the group consisting of phenyl, pyridyl, primidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, cyclopentyl, cyclohexyl, methoxy, phenyl, $CF_3$ or CN; a group with donor or acceptor action, selected from halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$.

The key of the present invention is the provision of Ir carbene complexes having diaryl substituted carbene ligands bearing a substituent at the 2 position of one of the aryl residues bound to one of the carbene nitrogen atoms. By substitution of the 2 position of the aryl residue, it is possible to obtain metal-carbene complexes having diaryl substituted carbene ligands only or mainly in form of their mer isomer. Further, cyclometallation of said substituted aryl residue with Ir is avoided respectively substantially reduced. Therefore, the specific cyclometallated Ir complexes of formula (I) according to the present invention are present in form of their mer isomer as only or predominant isomer and in form of only one or mainly one cyclometallation isomer. Additionally, the emission lifetime (emission decay time) of said complexes is short and the quantum yields are high to very high. Devices comprising the complexes according to the present invention show high efficiency and luminous efficacy as well as low voltage and especially long operational lifetime.

In the context of the present invention, cyclometallated Ir complex means that the aryl residue substituted to one of the carbene nitrogen atoms (i.e. nitrogen atoms of the of the carbene unit) undergoes metallation with formation of an Ir-carbon a bond, as shown in the following for a cyclometallated Ir complex of formula (I):

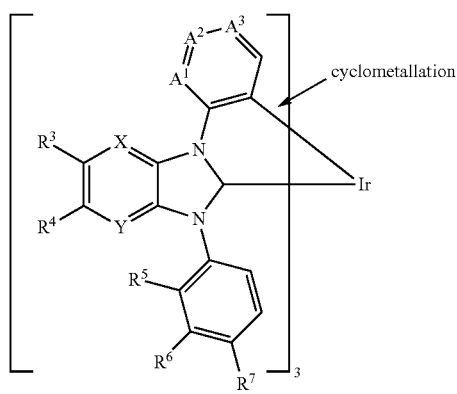

In the context of the present invention, cyclometallation isomer means that—in the case of an Ir complex of formula (I)—two cyclometallation isomers (isomer A and isomer B) are possible in principle:

(A)

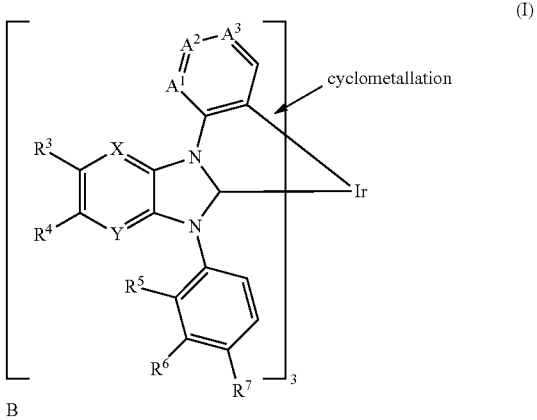

B

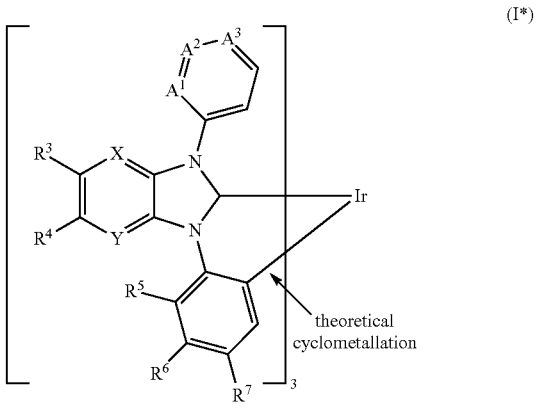

However, since the Ir carbene complex according to the present invention comprises at least one carbene ligand bearing a substituent at the 2 position of one of the aryl residues bound to one of the carbene nitrogen atoms ($R^5$), the formation of the cyclometallation isomer B is avoided respectively substantially reduced.

The 2 position of one of the aryl residues bound to one of the carbene nitrogen atoms in the Ir carbene complex according to the present invention is—in the context of the present invention—the position substituted with $R^5$.

It has been found by the inventors that a substitution of only one 2 position of one of the aryl residues bound to one of the carbene nitrogen atoms is sufficient to provide only or mainly the mer isomer and to avoid or to substantially reduce cyclometallation of said aryl residue with Ir.

In the context of the present invention, the terms aryl radical, unit or group, heteroaryl radical, unit or group, alkyl radical, unit or group, cycloalkyl radical, unit or group, cycloheteroalkyl radical, unit or group, and groups with donor or acceptor action are each defined as follows—unless stated otherwise:

In the aryl radicals, heteroaryl radicals, alkyl radicals, cycloalkyl radicals, cycloheteroalkyl radicals and groups with donor or acceptor action mentioned below, one or more hydrogen atoms (if present) may be substituted by deuterium atoms.

Aryl radicals or substituted or unsubstituted aryl radicals having 6 to 30, preferably 6 to 18 carbon atoms ($C_6$-$C_{30}$-aryl radicals) refer in the present invention to radicals which are derived from monocyclic, bicyclic or tricyclic aromatics which do not comprise any ring heteroatoms. When the systems are not monocyclic systems, the term "aryl" for the second ring also includes the saturated form (perhydro form) or the partly unsaturated form (for example the dihydro form or tetrahydro form), provided that the particular forms are known and stable. This means that the term "aryl" in the present invention encompasses, for example, also bicyclic or tricyclic radicals in which either both or all three radicals are aromatic, and bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to aryl radicals having a base structure of 6 to 13 carbon atoms, for example phenyl, naphthyl or fluorenyl, very particular preference is given to aryl radicals having a base structure of 6 carbon atoms.

The aryl radicals or $C_6$-$C_{30}$-aryl radicals may be unsubstituted or substituted by one or more further radicals. Suitable further radicals are selected from the group consisting of $C_1$-$C_{20}$-alkyl, $C_6$-$C_{24}$-aryl and substituents with donor or acceptor action, suitable substituents with donor or acceptor action are specified below. Preferred are unsubstituted aryl radicals, having from 6 to 12 carbon atoms, a monosubstituted aryl radicals having from 6 to 18 carbon atoms or disubstituted aryl radicals having from 6 to 18 carbon atoms. Preferred substituents are $C_1$-$C_{20}$-alkyl groups, $C_1$-$C_{20}$-alkoxy groups, CN, $CF_3$, halogen radicals, $SiR^{10}R^{11}R^{12}$, wherein $R^{10}$, $R^{11}$ and $R^{12}$ are specified below or amino groups ($NR^{32}R^{33}$ where suitable $R^{32}$ and $R^{33}$ radicals are specified below), more preferred substituents are methyl, ethyl, n-propyl, iso-propyl, n-butyl, tert-butyl, sec-butyl, iso-butyl, cyclopentyl, cyclohexyl, methoxy, phenyl or $CF_3$; a group with donor or acceptor action, selected from OPh, halogen radicals, preferably F or Cl, more preferably F; $CF_3$, CN; or $SiR^{10}R^{11}R^{12}$, preferably $SiMe_3$, $SiPh_3$, $SiEt_3$ or $SiPh_2tBu$.

Heteroaryl radicals or substituted or unsubstituted heteroaryl radicals having a total of 5 to 30, preferably 5 to 20 carbon atoms and/or heteroatoms are understood to mean monocyclic, bicyclic or tricyclic heteroaromatics, some of which can be derived from the aforementioned aryl, in which at least one carbon atom in the aryl base structure has been replaced by a heteroatom. Preferred heteroatoms are N, O and S. The base structure of the heteroaryl radicals is especially preferably selected from systems such as pyridine, pyrimidine and pyrazine and five-membered heteroaromatics such as thiophene, pyrrole, imidazole, thiazole, oxazole or furan. These base structures may optionally be fused to one or two six-membered aromatic radicals. Suitable fused heteroaromatics are carbazolyl, benzimidazolyl, benzofuranyl, benzothiazolyl, benzoxazolyl, dibenzofuranyl, dibenzothiophenyl, indolyl or benzimidazo[1,2-a]benzimidazolyl. Particularly preferred base structures are pyridyl, primidyl, pyrazinyl, carbazolyl, dibenzofuranyl, dibenzothiophenyl, indolyl, benzofuranyl and benzothiophenyl.

The base structure may be substituted at one, more than one or all substitutable positions, suitable substituents being the same as those already specified under the definition of $C_6$-$C_{30}$-aryl. Preferred are unsubstituted heteroaryl radicals, having a total of from 5 to 16 carbon atoms and/or heteroatoms, monosubstituted heteroaryl radicals, having a total of from 5 to 18 carbon atoms and/or heteroatoms and disubstituted heteroaryl radicals, having a total of from 5 to 20 carbon atoms and/or heteroatoms.

An alkyl radical in the context of the present application is a linear or branched alkyl radical, optionally interrupted by at least one heteroatom, and having 1 to 20 carbon atoms. Preference is given to $C_1$- to $C_{10}$-alkyl radicals, particular preference to $C_1$- to $C_6$-alkyl radicals. In addition, the alkyl radicals may be unsubstituted or substituted by one or more substituents. Preferred substituents are selected from the group consisting of groups with donor or acceptor action, preferably $C_1$-$C_{20}$-alkoxy, halogen, more preferably F, $C_1$-$C_{20}$-haloalkyl, e.g. $CF_3$; deuterium; a substituted or unsubstituted cycloalkyl radical having a total of from 3 to 30 carbon atoms; a substituted or unsubstituted heterocycloalkyl radical, interrupted by at least one heteroatom, selected from O, S and N, and having a total of from 3 to 30 carbon atoms and/or heteroatoms; a substituted or unsubstituted aryl radical, having a total of from 6 to 30 carbon atoms; or a substituted or an unsubstituted heteroaryl radical, having a total of from 5 to 30 carbon atoms and/or heteroatoms, selected from O, S and N. Suitable aryl substituents are specified above and suitable alkoxy and halogen substituents are specified below. Examples of suitable alkyl groups are methyl, ethyl, propyl, butyl, pentyl, hexyl, heptyl and octyl, and also $C_1$-$C_{20}$-haloalkyl-, $C_6$-$C_{30}$-aryl-, $C_1$-$C_{20}$-alkoxy- and/or halogen-substituted, especially F-substituted, derivatives of the alkyl groups mentioned, for example $CF_3$ or $CF_2CF_3$. This comprises both the n-isomers of the radicals mentioned and branched isomers such as isopropyl, isobutyl, isopentyl, sec-butyl, tert-butyl, iso-butyl, neopentyl, 3,3-dimethylbutyl, 3-ethylhexyl, etc. Preferred alkyl groups are methyl, ethyl, n-propyl, isopropyl, n-butyl, sec-butyl, iso-butyl, tert-butyl, $CF_3$ and $CF_2CF_3$. Most preferred alkyl radicals are $CF_3$, methyl, ethyl, n-propyl, iso-propyl, n-butyl, tert-butyl, sec-butyl and iso-butyl.

A cycloalkyl radical is understood in the context of the present invention to mean a substituted or unsubstituted cycloalkyl radical having 3 to 30 carbon atoms. Preferred are cycloalkyl radicals having 3 to 18, more preferably 3 to 12 and most preferably 3 to 7 carbon atoms in the base structure (ring) to understand. Suitable substituents are the substituents mentioned for the alkyl groups. Examples of suitable cycloalkyl groups, which may be unsubstituted or substituted by the radicals mentioned above for the alkyl groups, are cyclopentyl, cyclohexyl, cycloheptyl, cyclooctyl, cyclononyl and cyclodecyl. They may also be polycyclic ring systems such as decalinyl, norbornyl, bornanyl or adamantyl.

A heterocycloalkyl radical or a substituted or unsubstituted heterocycloalkyl radical having 3 to 30 carbon atoms and/or heteroatoms is understood to mean heterocyclo-alkyl radicals having 3 to 18, preferably 5 to 10 and more preferably 5 to 8 ring atoms, where at least one carbon atom in the heterocycloalkyl base structure has been replaced by a heteroatom. Preferred heteroatoms are N, O and S. Suitable substituents are the substituents mentioned for the alkyl groups. Examples of suitable heterocycloalkyl groups, which may be unsubstituted or substituted by the radicals mentioned above for the alkyl groups, are radicals derived from the following heterocycles: pyrrolidine, thiolane, tetrahydrofuran, 1,2-oxathiolane, oxazolidine, piperidine, thiane, oxane, dioxane, 1,3-dithiane, morpholine, piperazine. They may also be polycyclic ring systems.

Suitable alkoxy radicals and alkylthio radicals derive correspondingly from the aforementioned alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. In this context, $C_3H_7$, $C_4H_9$ and $C_8H_{17}$ comprise both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

In the context of the present application, groups with donor or acceptor action are understood to mean the following groups:

$C_1$-$C_{20}$-alkoxy, $C_6$-$C_{30}$-aryloxy, $C_1$-$C_{20}$-alkylthio, $C_6$-$C_{30}$-arylthio, $SiR^{10}R^{11}R^{12}$, halogen radicals, halogenated $C_1$-$C_{20}$-alkyl radicals, carbonyl (—CO($R^{32}$)), carbonylthio (—C=O(S$R^{32}$)), carbonyloxy (—C=O(O$R^{32}$)), oxycarbonyl (—OC=O($R^{32}$)), thiocarbonyl (—SC=O($R^{32}$)), amino (—N$R^{32}R^{33}$), OH, pseudohalogen radicals, amido (—C=O(N$R^{32}R^{33}$)), —N$R^{32}$C=O($R^{33}$), phosphonate (—P(O)(O$R^{32}$)$_2$), phosphate (—OP(O)(O$R^{32}$)$_2$), phosphine (—P$R^{32}R^{33}$), phosphine oxide (P(O)$R^{32}_2$), sulfate (—OS(O)$_2$O$R^{32}$), sulfoxide (—S(O)$R^{32}$), sulfonate (—S(O)$_2$ O$R^{32}$), sulfonyl (—S(O)$_2R^{32}$), sulfonamide (—S(O)$_2$ N$R^{32}R^{33}$), NO$_2$, boronic esters (—OB(O$R^{32}$)$_2$), imino (—C=N$R^{32}R^{33}$)), borane radicals, stannate radicals, hydrazine radicals, hydrazone radicals, oxime radicals, nitroso groups, diazo groups, vinyl groups, sulfoximines, alanes, germanes, boroxines and borazines.

Preferred substituents with donor or acceptor action are selected from the group consisting of: $C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{10}R^{11}R^{12}$; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —C(O)OC$_1$-$C_4$-alkyl, preferably —C(O)OMe, P(O)$R_2$, preferably P(O)Ph$_2$, and SO$_2R_2$, preferably SO$_2$Ph.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{10}R^{11}R^{12}$, where suitable $R^{10}$, $R^{11}$ and $R^{12}$ radicals are specified below, diphenylamino, or —C(O)OC$_1$-$C_4$-alkyl. Even more preferred are OPh, halogen radicals, preferably F or Cl, more preferably F; $CF_3$, CN; or $SiR^{10}R^{11}R^{12}$, preferably SiMe$_3$, SiPh$_3$, SiEt$_3$ or SiPh$_2$tBu.

The aforementioned groups with donor or acceptor action are not intended to rule out the possibility that further radicals and groups among those specified above may also have donor or acceptor action. For example, the aforementioned heteroaryl radicals are likewise groups with donor or acceptor action, and the $C_1$-$C_{20}$-alkyl radicals are groups with donor action.

The $R^{32}$ and $R^{33}$ radicals mentioned are each independently:

Hydrogen, substituted or unsubstituted $C_1$-$C_{20}$-alkyl or substituted or unsubstituted $C_6$-$C_{30}$-aryl or substituted or unsubstituted heteroaryl having 5 to 30 ring atoms, suitable and preferred alkyl and aryl radicals having been specified above. More preferably, the $R^{32}$, $R^{33}$ and $R^{34}$ radicals are $C_1$-$C_6$-alkyl, e.g. methyl, ethyl, i-propyl or tert-butyl, or phenyl or pyridyl, most preferably methyl or phenyl.

The $R^{10}$, $R^{11}$ and $R^{12}$ radicals mentioned are each independently:

a linear or branched alkyl radical, having from 1 to 6 carbon atoms, preferably methyl, ethyl, n-propyl, iso-propyl, n-butyl, tert-butyl, sec-butyl or iso-butyl; a substituted or unsubstituted aryl radical, having from 6 to 18 carbon atoms, preferably phenyl or tolyl; a substituted or unsubstituted heteroaryl radical, having a total of from 5 to 18 carbon atoms and/or heteroatoms; a substituted or unsubstituted cycloalkyl radical having a total of from 3 to 18 carbon atoms, preferably cyclopentyl or cyclohexyl.

Cyclometallated Ir Complex of Formula (I)

The metal in the cyclometallated Ir complex of formula (I) is preferably Ir(III).

The radicals, groups and symbols in the bidentate ligands of formula (I) of the cyclometallated Ir complex preferably have—independently of each other—the following meanings:

$R^1$, $R^2$, $R^3$, $R^4$, $R^6$ and $R^7$ are each independently hydrogen; deuterium; a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action;

preferably, $R^1$, $R^2$, $R^3$, $R^4$, $R^6$ and $R^7$ are each independently hydrogen, deuterium, a linear or branched, substituted or unsubstituted alkyl radical, having from 1 to 6 carbon atoms; a substituted or unsubstituted cycloalkyl radical having a total of from 3 to 12 carbon atoms; an unsubstituted aryl radical, having from 6 to 12 carbon atoms, a monosubstituted aryl radical having from 6 to 18 carbon atoms, a disubstituted aryl radical having from 6 to 18 carbon atoms; an unsubstituted heteroaryl radical, having a total of from 5 to 16 carbon atoms and/or heteroatoms, a monosubstituted heteroaryl radical, having a total of from 5 to 18 carbon atoms and/or heteroatoms, a disubstituted heteroaryl radical, having a total of from 5 to 20 carbon atoms and/or heteroatoms; more preferably, the aryl radical or heteroaryl radical are selected from the group consisting of phenyl, pyridyl, primidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, cyclopentyl, cyclohexyl, methoxy, phenyl or $CF_3$; a group with donor or acceptor action, selected from OPh, halogen radicals, preferably F or Cl, more preferably F; $CF_3$, CN; or $SiR^{10}R^{11}R^{12}$, preferably SiMe$_3$, SiPh$_3$, SiEt$_3$ or SiPh$_2$tBu;

or $R^1$ and $R^2$, $R^3$ and $R^4$ and/or $R^6$ and $R^7$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms.

More preferably, $R^1$, $R^2$, $R^3$, $R^4$, $R^6$ and $R^7$ are each independently hydrogen; deuterium; methyl, ethyl, n-propyl, iso-propyl, n-butyl, tert-butyl, sec-butyl, iso-butyl, cyclopentyl, cyclohexyl, $OCH_3$, $OCF_3$; phenyl, pyridyl, primidyl, pyrazinyl, carbazolyl, dibenzofuranyl, dibenzothiophenyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, $CF_3$ or phenyl; a group with donor or acceptor action, selected from F, $CF_3$, CN and $SiPh_3$; most preferably, $R^1$, $R^2$, $R^3$, $R^4$, $R^6$ and $R^7$ are each independently hydrogen; deuterium; methyl, ethyl, n-propyl, iso-propyl, n-butyl, tert-butyl, sec-butyl, iso-butyl; phenyl, pyridyl, primidyl, pyrazinyl, carbazolyl, dibenzofuranyl, dibenzothiophenyl, wherein the aforementioned radicals may be unsubstituted or substituted by methyl, ethyl, iso-propyl, tert-butyl, iso-butyl or methoxy; $CF_3$ or CN.

$R^{10}$, $R^{11}$, $R^{12}$ are each independently a linear or branched alkyl radical, having from 1 to 6 carbon atoms, preferably methyl, ethyl, n-propyl, iso-propyl, n-butyl, tert-butyl, sec-butyl or iso-butyl; a substituted or unsubstituted aryl radical, having from 6 to 12 carbon atoms, preferably phenyl or tolyl; a substituted or unsubstituted heteroaryl radical, having a total of from 5 to 15 carbon atoms and/or heteroatoms; a substituted or unsubstituted cycloalkyl radical having a total of from 3 to 7 carbon atoms, preferably cyclopentyl or cyclohexyl.

$R^5$ is a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, $R^5$ is a linear or branched, substituted or unsubstituted alkyl radical, having from 1 to 6 carbon atoms; a substituted or unsubstituted cycloalkyl radical having a total of from 3 to 12 carbon atoms; an unsubstituted aryl radical, having from 6 to 12 carbon atoms, a monosubstituted aryl radical having from 6 to 18 carbon atoms, a disubstituted aryl radical having from 6 to 18 carbon atoms; an unsubstituted heteroaryl radical, having a total of from 5 to 16 carbon atoms and/or heteroatoms, a monosubstituted heteroaryl radical, having a total of from 5 to 18 carbon atoms and/or heteroatoms, a disubstituted heteroaryl radical, having a total of from 5 to 20 carbon atoms and/or heteroatoms; more preferably, the aryl radical or heteroaryl radical are selected from the group consisting of phenyl, pyridyl, primidyl, pyrazinyl, carbazolyl, dibenzofuranyl, dibenzothiophenyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, cyclopentyl, cyclohexyl, methoxy, phenyl, $CF_3$ or CN; a group with donor or acceptor action, selected from $CF_3$, CN; or $SiR^{10}R^{11}R^{12}$, preferably $SiMe_3$, $SiPh_3$, $SiEt_3$ or $SiPh_2tBu$.

More preferably, $R^5$ is methyl, ethyl, n-propyl, iso-propyl, n-butyl, tert-butyl, sec-butyl, iso- butyl, cyclopentyl, cyclohexyl, $OCH_3$, $OCF_3$; phenyl, pyridyl, primidyl, pyrazinyl, wherein the aforementioned radicals may be substituted by, preferably monosubstituted by methyl, ethyl, n-propyl, iso-propyl, n-butyl, tert-butyl, sec-butyl, iso-butyl, methoxy or phenyl or unsubstituted; a group with donor or acceptor action, selected from $CF_3$ and CN;

most preferably, $R^5$ is methyl, ethyl, n-propyl, iso-propyl, n-butyl, sec-butyl, iso-butyl; phenyl, tolyl or pyridyl.

Particularly preferred are complexes of formula (I), wherein:

$R^1$, $R^2$, $R^3$, $R^4$, $R^6$ and $R^7$ are each independently hydrogen; deuterium; methyl, ethyl, n-propyl, iso-propyl, n-butyl, tert-butyl, sec-butyl, iso-butyl, cyclopentyl, cyclohexyl, $OCH_3$, $OCF_3$; phenyl, pyridyl, primidyl, pyrazinyl, carbazolyl, dibenzofuranyl, dibenzothiophenyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, $CF_3$ or phenyl; a group with donor or acceptor action, selected from F, $CF_3$, CN and $SiPh_3$; and $R^5$ is methyl, ethyl, n-propyl, iso-propyl, n-butyl, tert-butyl, sec-butyl, iso-butyl, cyclopentyl, cyclohexyl, $OCH_3$, $OCF_3$; phenyl, pyridyl, primidyl, pyrazinyl, wherein the aforementioned radicals may be substituted by, preferably monosubstituted by methyl, ethyl, n-propyl, iso-propyl, n-butyl, tert-butyl, sec-butyl, iso-butyl, methoxy or phenyl unsubstituted; a group with donor or acceptor action, selected from $CF_3$ and CN.

Even more preferred are complexes of formula (I), wherein:

$R^1$, $R^2$, $R^3$, $R^4$, $R^6$ and $R^7$ are each independently hydrogen; deuterium; methyl, ethyl, n-propyl, iso-propyl, n-butyl, tert-butyl, sec-butyl, iso-butyl; phenyl, pyridyl, primidyl, pyrazinyl, carbazolyl, dibenzofuranyl, dibenzothiophenyl, wherein the aforementioned radicals may be unsubstituted or substituted by methyl, ethyl, iso-propyl, tert-butyl, iso-butyl or methoxy; $CF_3$ or CN; and $R^5$ is methyl, ethyl, n-propyl, iso-propyl, n-butyl, sec-butyl, iso-butyl; phenyl, tolyl or pyridyl.

X is CH, CD or N, preferably CH or N.

Y is $CR^8$ or N, preferably CH or N.

Preferably, X and Y are each independently CH, CD or N, preferably CH or N.

In one preferred embodiment of the present invention

X is N; and

Y is $CR^8$, preferably CH.

In a further preferred embodiment of the present invention

X is N; and

Y is N.

In a further preferred embodiment of the present invention

X is CH or CD, preferably CH; and

Y is $CR^8$, preferably CH.

In a further embodiment of the present invention

X is CH or CD, preferably CH; and

Y is N.

$R^8$ is hydrogen; deuterium; a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; preferably, $R^8$ is hydrogen, deuterium, a linear or branched, substituted or unsubstituted alkyl radical, having from 1 to 6 carbon atoms; a substituted or unsubstituted cycloalkyl radical having a total of from 3 to 12 carbon atoms; an unsubstituted aryl radical, having from 6 to 12 carbon atoms, a monosubstituted aryl radical having from 6 to 18 carbon atoms, a disubstituted aryl radical having from 6 to 18 carbon atoms; an unsubstituted heteroaryl radical, having a total of from 5 to 16 carbon atoms and/or heteroatoms, a monosubstituted heteroaryl radical, having a total of from 5 to 18 carbon atoms and/or heteroatoms, a disubstituted heteroaryl radical, having a total of from 5 to 20 carbon atoms and/or heteroatoms; more preferably, the aryl radical or heteroaryl radical are selected from the group consisting of phenyl, pyridyl, primidyl, pyrazinyl, carbazolyl, dibenzofuranyl, dibenzothiophenyl, fluorenyl, indolyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, cyclopentyl, cyclohexyl, methoxy, phenyl, $CF_3$ or CN; a group with donor or acceptor action, selected from halogen radicals, preferably F or Cl, more preferably F; $CF_3$; CN; or $SiR^{10}R^{11}R^{12}$, preferably $SiMe_3$, $SiPh_3$, $SiEt_3$ or $SiPh_2tBu$.

The carbene ligands in the cyclometallated Ir complexes of formula (I) are monoanionic bidentate ligands.

Preferably, the three carbene ligands in the cyclometallated Ir complexes of the general formula (I) are identical.

In a preferred embodiment of the present invention, the cyclometallated Ir complexes of formula (I) are meridional (mer) complexes.

Preferred cyclometallated Ir complexes of formula (I) are:
Compounds of formula (I)
wherein the radicals and groups $R^1$, $R^2$, $R^3$, $R^4$, $R^6$, $R^5$, $R^7$, X and Y have the following meanings:

| Cpd. | X | Y | $R^7$ | $R^6$ | $R^5$ | $R^4$ | $R^3$ | $R^2$ | $R^1$ |
|---|---|---|---|---|---|---|---|---|---|
| 1 | N | N | H | H | methyl | H | H | H | H |
| 2 | N | CH | H | H | methyl | H | H | H | H |
| 3 | CH | CH | H | H | methyl | H | H | H | H |
| 4 | CH | N | H | H | methyl | H | H | H | H |
| 5 | N | CH | H | H | methyl | CN | H | H | tert-butyl |
| 6 | N | N | H | H | methyl | CN | H | H | tert-butyl |
| 7 | CH | CH | H | H | Methyl | CN | H | H | tert-butyl |
| 8 | CH | N | H | H | Methyl | CN | H | H | tert-butyl |
| 9 | N | CH | H | H | Methyl | $CF_3$ | H | H | H |
| 10 | N | N | H | H | methyl | $CF_3$ | H | H | H |
| 11 | CH | CH | H | H | methyl | $CF_3$ | H | H | H |
| 12 | CH | N | H | H | methyl | $CF_3$ | H | H | H |
| 13 | N | N | H | H | methyl | H | o-tolyl | H | H |
| 14 | N | CH | H | H | methyl | H | o-tolyl | H | H |
| 15 | CH | CH | H | H | methyl | H | o-tolyl | H | H |
| 16 | CH | N | H | H | methyl | H | o-tolyl | H | H |
| 17 | N | N | H | H | phenyl | H | H | H | H |
| 18 | N | CH | H | H | phenyl | H | H | H | H |
| 19 | CH | CH | H | H | phenyl | H | H | H | H |
| 20 | CH | N | H | H | phenyl | H | H | H | H |
| 21 | N | N | Phenyl | H | methyl | H | H | H | H |
| 22 | N | CH | Phenyl | H | methyl | H | H | H | H |
| 23 | CH | CH | phenyl | H | methyl | H | H | H | H |
| 24 | CH | N | phenyl | H | methyl | H | H | H | H |
| 25 | N | N | H | H | —$CH_3$ | H | H | H | H |
| 26 | N | N | H | H | —$CH_2CH_3$ | H | H | H | H |
| 27 | N | N | H | H | iso-propyl | H | H | H | H |
| 28 | N | N | H | H | —$CH_3$ | H | H | H | iso-butyl |
| 29 | N | N | H | H | —Ph | H | H | H | iso-butyl |
| 30 | N | N | H | H | neopentyl | H | H | H | H |
| 31 | N | N | H | H |  | H | H | H | H |
| 32 | N | N | H | H |  | H | H | H | H |
| 33 | N | N | H | H | —$CH_3$ | H | H | H | tert-butyl |
| 34 | N | N | H | H | —Ph | H | H | H | tert-butyl |
| 35 | N | N | N |  | —$CH_3$ | H | H | H | H |
| 36 | N | N | H |  | —$CH_3$ | H | H | H | H |
| 37 | N | N | H | H |  | H | H | H | H |

-continued
| Cpd. | X | Y | R⁷ | R⁶ | R⁵ | R⁴ | R³ | R² | R¹ |
|---|---|---|---|---|---|---|---|---|---|
|  | N | N | H | H | —CH₃ | H | H | H |  |
| 38 | N | N | H | H | —CH₃ | H | H | H | 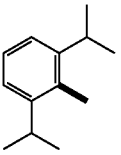 |
| 39 | N | N | H | H | —CH₃ | H | H | H | 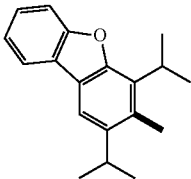 |
| 40 | N | N | H | H | —CH₃ | H | H | H | 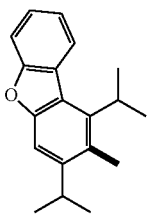 |
| 41 | N | N | H | H | —CH₃ | H | H | H | 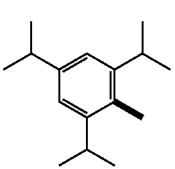 |
| 42 | N | N | H | H | —CH₃ | H | H | H | 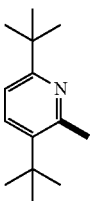 |
| 43 | N | N | H | H | —Ph | H | H | H | 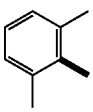 |
| 44 | N | N | H | H | —Ph | H | H | H | 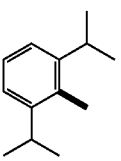 |
| 45 | N | N | H | H | —Ph | H | H | H | 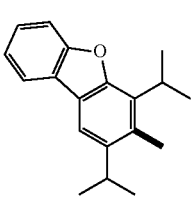 |

-continued

| Cpd. | X | Y | R⁷ | R⁶ | R⁵ | R⁴ | R³ | R² | R¹ |
|---|---|---|---|---|---|---|---|---|---|
| 46 | N | N | H | H | —Ph | H | H | H | (1-isopropyl, 2-methyl, 3-isopropyl dibenzofuran) |
| 47 | N | N | H | H | —Ph | H | H | H | (2,4,6-triisopropyl-3,5-dimethylphenyl) |
| 48 | N | N | H | H | —Ph | H | H | H | (2,6-di-tert-butyl-3-methylpyridinyl) |
| 49 | N | CH | H | H | —CH₃ | H | H | H | H |
| 50 | N | CH | H | H | —CH₂CH₃ | H | H | H | H |
| 51 | N | CH | H | H | iso-propyl | H | H | H | H |
| 52 | N | CH | H | H | —CH₃ | H | H | H | iso-butyl |
| 53 | N | CH | H | H | —Ph | H | H | H | iso-butyl |
| 54 | N | CH | H | H | neopentyl | H | H | H | H |
| 55 | N | CH | H | H | cyclopentyl | H | H | H | H |
| 56 | N | CH | H | H | cyclohexyl | H | H | H | H |
| 57 | N | CH | H | H | —CH₃ | H | H | H | tert-butyl |
| 58 | N | CH | H | H | —Ph | H | H | H | tert-butyl |
| 59 | N | CH | H | phenyl | —CH₃ | H | H | H | H |
| 60 | N | CH | H | 4-pyridinyl | —CH₃ | H | H | H | H |
| 61 | N | CH | H | H | —CH₃ | H | H | H | (2,3,4-trimethylphenyl) |
| 62 | N | CH | H | H | —CH₃ | H | H | H | (2,6-diisopropyl-3-methylphenyl) |
| 63 | N | CH | H | H | —CH₃ | H | H | H | (1-isopropyl, 2-methyl, 3-isopropyl dibenzofuran) |

-continued

| Cpd. | X | Y | R⁷ | R⁶ | R⁵ | R⁴ | R³ | R² | R¹ |
|---|---|---|---|---|---|---|---|---|---|
| 64 | N | CH | H | H | —CH₃ | H | H | H | (dibenzofuran with two isopropyl and methyl substituents) |
| 65 | N | CH | H | H | —CH₃ | H | H | H | (2,6-diisopropylphenyl with methyl) |
| 66 | N | CH | H | H | —CH₃ | H | H | H | (pyridyl with two tert-butyl and methyl substituents) |
| 67 | N | CH | H | H | —Ph | H | H | H | (2,3-dimethylphenyl) |
| 68 | N | CH | H | H | —Ph | H | H | H | (2,6-diisopropylphenyl with methyl) |
| 69 | N | CH | H | H | —Ph | H | H | H | (dibenzofuran with two isopropyl and methyl substituents) |
| 70 | N | CH | H | H | —Ph | H | H | H | (dibenzofuran with two isopropyl and methyl substituents) |
| 71 | N | CH | H | H | —Ph | H | H | H | (2,4,6-triisopropylphenyl) |

-continued
| Cpd. | X | Y | R⁷ | R⁶ | R⁵ | R⁴ | R³ | R² | R¹ |
|---|---|---|---|---|---|---|---|---|---|
| 72 | N | CH | H | H | —Ph | H | H | H | 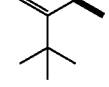 |
| 73 | CH | N | H | H | —CH₃ | H | H | H | H |
| 74 | CH | N | H | H | —CH₂CH₃ | H | H | H | H |
| 75 | CH | N | H | H | iso-propyl | H | H | H | H |
| 76 | CH | N | H | H | —CH₃ | H | H | H | iso-butyl |
| 77 | CH | N | H | H | —Ph | H | H | H | iso-butyl |
| 78 | CH | N | H | H | neopentyl | H | H | H | H |
| 79 | CH | N | H | H |  | H | H | H | H |
| 80 | CH | N | H | H |  | H | H | H | H |
| 81 | CH | N | H | H | —CH₃ | H | H | H | tert-butyl |
| 82 | CH | N | H | H | —Ph | H | H | H | tert-butyl |
| 83 | CH | N | H |  | —CH₃ | H | H | H | H |
| 84 | CH | N | H |  | —CH₃ | H | H | H | H |
| 85 | CH | N | H | H | —CH₃ | H | H | H | 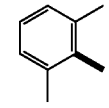 |
| 86 | CH | N | H | H | —CH₃ | H | H | H | 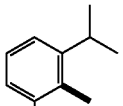 |
| 87 | CH | N | H | H | —CH₃ | H | H | H | 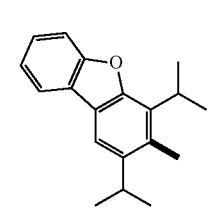 |
| 88 | CH | N | H | H | —CH₃ | H | H | H | 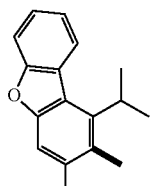 |

-continued
| Cpd. | X | Y | R⁷ | R⁶ | R⁵ | R⁴ | R³ | R² | R¹ |
|---|---|---|---|---|---|---|---|---|---|
| 89 | CH | N | H | H | —CH₃ | H | H | H | 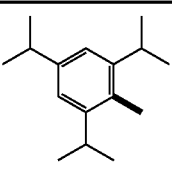 |
| 90 | CH | N | H | H | —CH₃ | H | H | H | 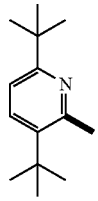 |
| 91 | CH | N | H | H | —Ph | H | H | H | 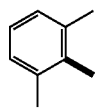 |
| 92 | CH | N | H | H | —Ph | H | H | H | 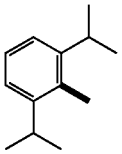 |
| 93 | CH | N | H | H | —Ph | H | H | H | 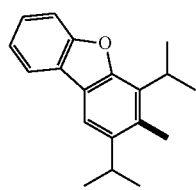 |
| 94 | CH | N | H | H | —Ph | H | H | H | 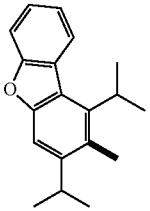 |
| 95 | CH | N | H | H | —Ph | H | H | H | 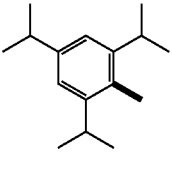 |
| 96 | CH | N | H | H | —Ph | H | H | H | 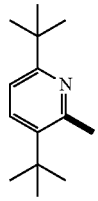 |
| 97 | CH | CH | H | H | —CH₃ | H | H | H | H |
| 98 | CH | CH | H | H | —CH₂CH₃ | H | H | H | H |
| 99 | CH | CH | H | H | iso-propyl | H | H | H | H |
| 100 | CH | CH | H | H | —CH₃ | H | H | H | iso-butyl |
| 101 | CH | CH | H | H | —Ph | H | H | H | iso-butyl |
| 102 | CH | CH | H | H | neopentyl | H | H | H | H |

-continued
| Cpd. | X | Y | R⁷ | R⁶ | R⁵ | R⁴ | R³ | R² | R¹ |
|---|---|---|---|---|---|---|---|---|---|
| 103 | CH | CH | H | H |  | H | H | H | H |
| 104 | CH | CH | H | H |  | H | H | H | H |
| 105 | CH | CH | H | H | —CH₃ | H | H | H | tert-butyl |
| 106 | CH | CH | H | H | —Ph | H | H | H | tert-butyl |
| 107 | CH | CH | H | 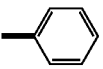 | —CH₃ | H | H | H | H |
| 108 | CH | CH | H | 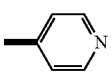 | —CH₃ | H | H | H | H |
| 109 | CH | CH | H | H | —CH₃ | H | H | H | 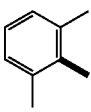 |
| 110 | CH | CH | H | H | —CH₃ | H | H | H | 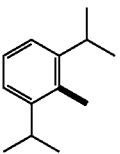 |
| 111 | CH | CH | H | H | —CH₃ | H | H | H | 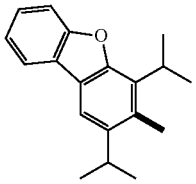 |
| 112 | CH | CH | H | H | —CH₃ | H | H | H | 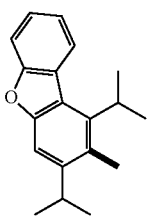 |
| 113 | CH | CH | H | H | —CH₃ | H | H | H | 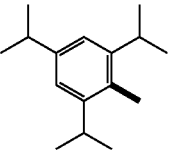 |
| 114 | CH | CH | H | H | —CH₃ | H | H | H | 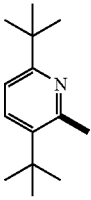 |
| 115 | CH | CH | H | H | —Ph | H | H | H | 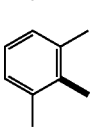 |

-continued
| Cpd. | X | Y | R⁷ | R⁶ | R⁵ | R⁴ | R³ | R² | R¹ |
|---|---|---|---|---|---|---|---|---|---|
| 116 | CH | CH | H | H | —Ph | H | H | H | 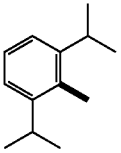 |
| 117 | CH | CH | H | H | —Ph | H | H | H | 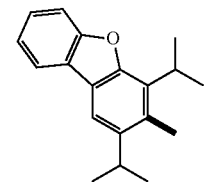 |
| 118 | CH | CH | H | H | —Ph | H | H | H | 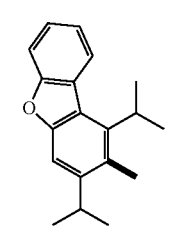 |
| 119 | CH | CH | H | H | —Ph | H | H | H | 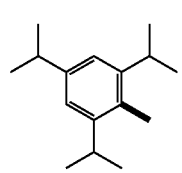 |
| 120 | CH | CH | H | H | —Ph | H | H | H | 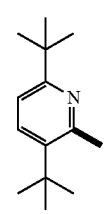 |
Particularly preferred inventive cyclometallated Ir complexes of formula (I) are the following complexes:
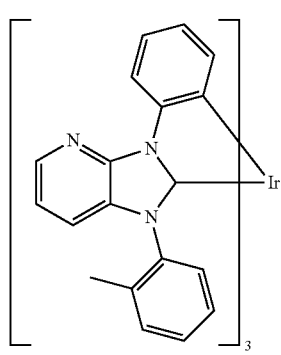
-continued
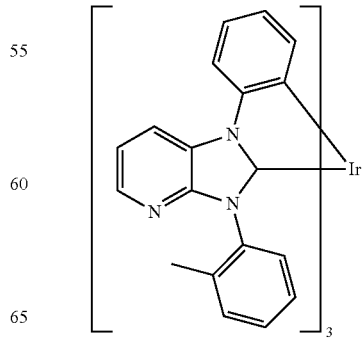

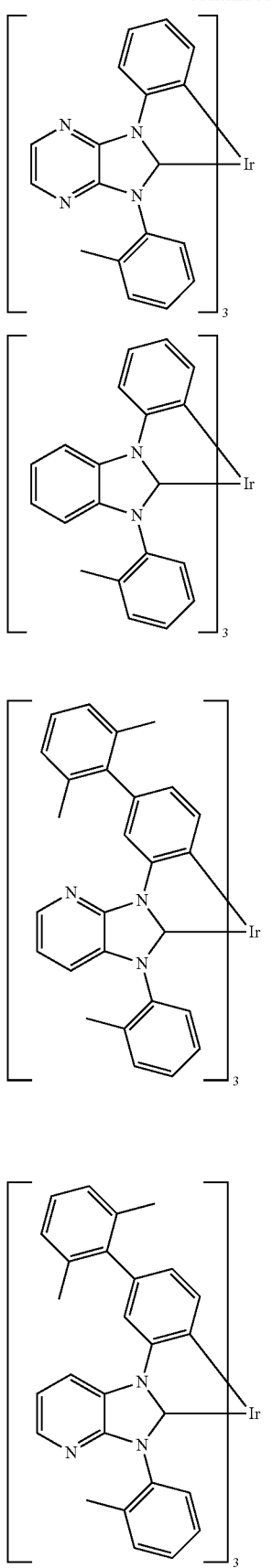
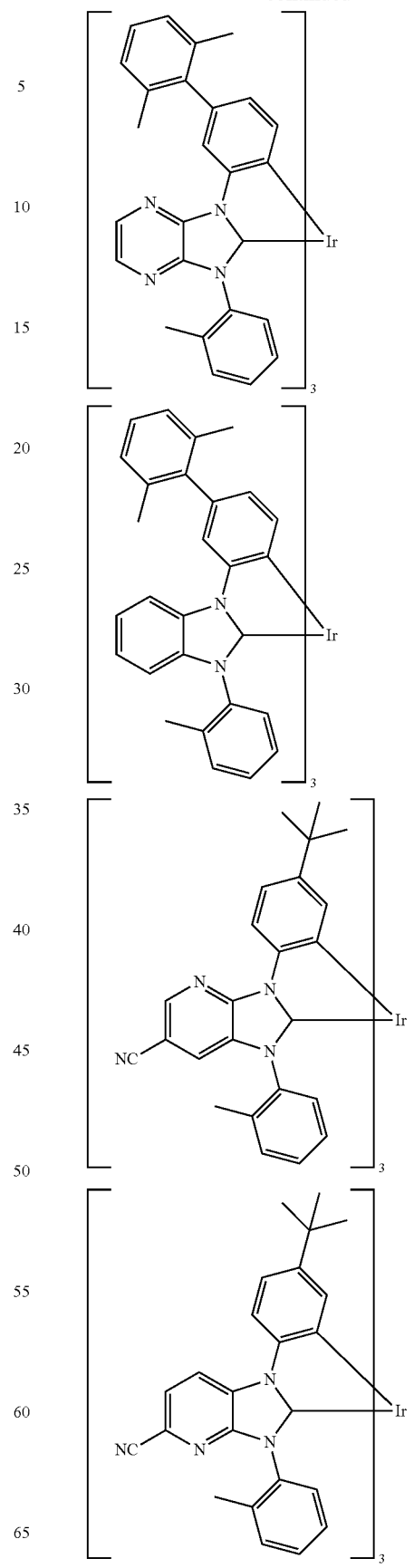

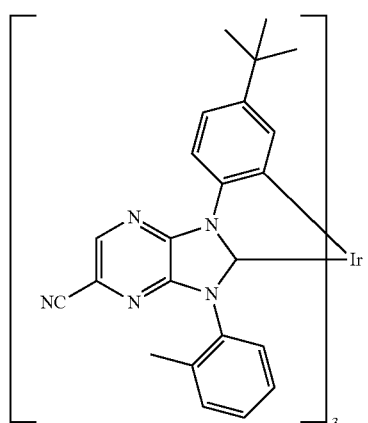
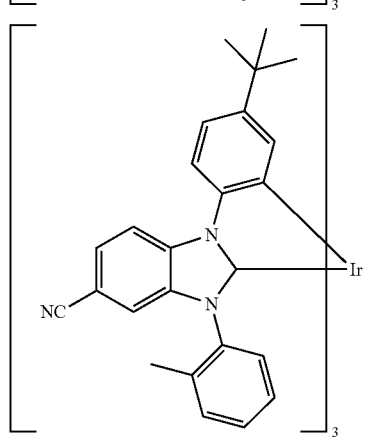
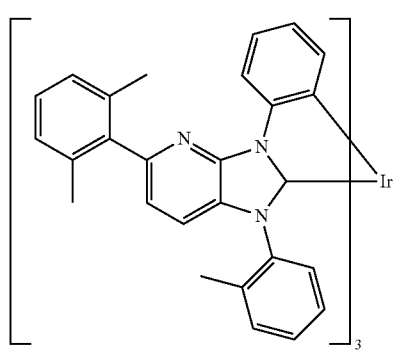
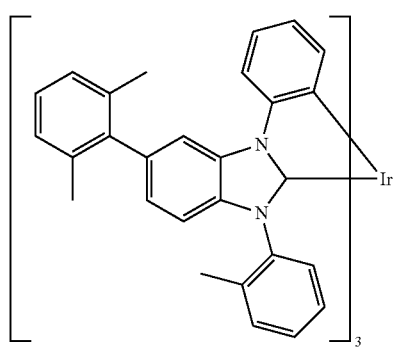
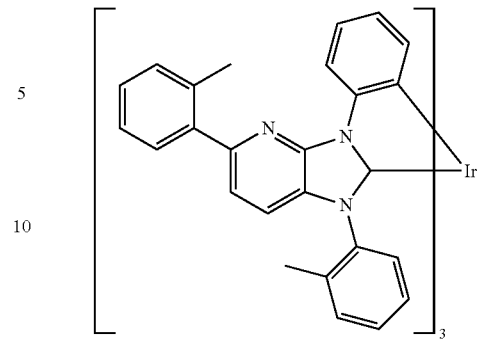
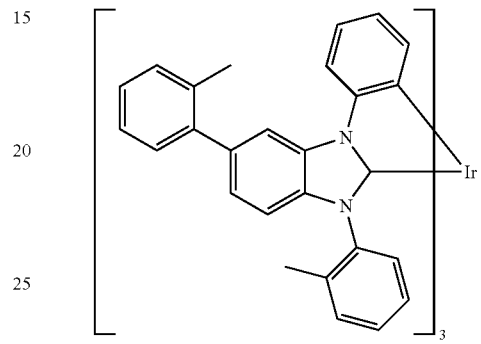
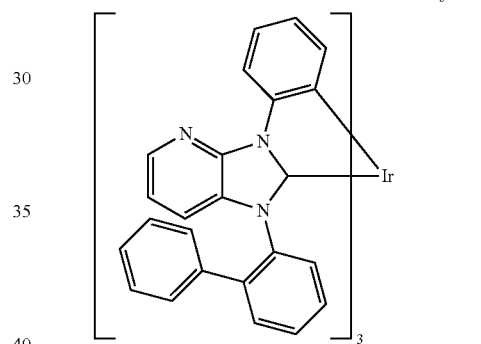
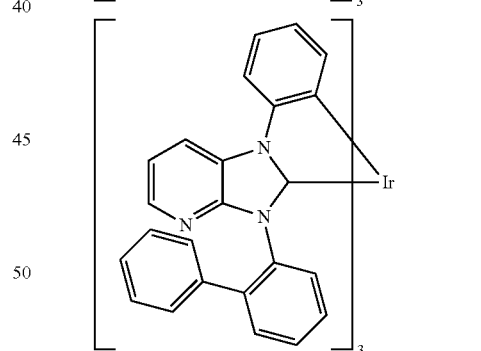
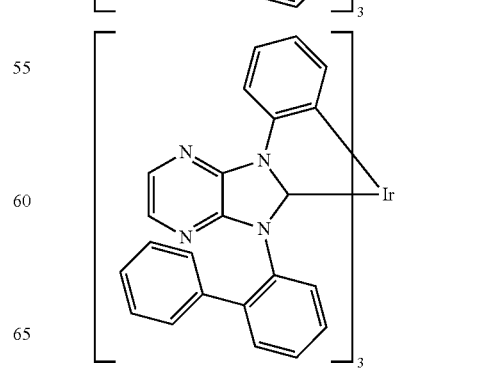

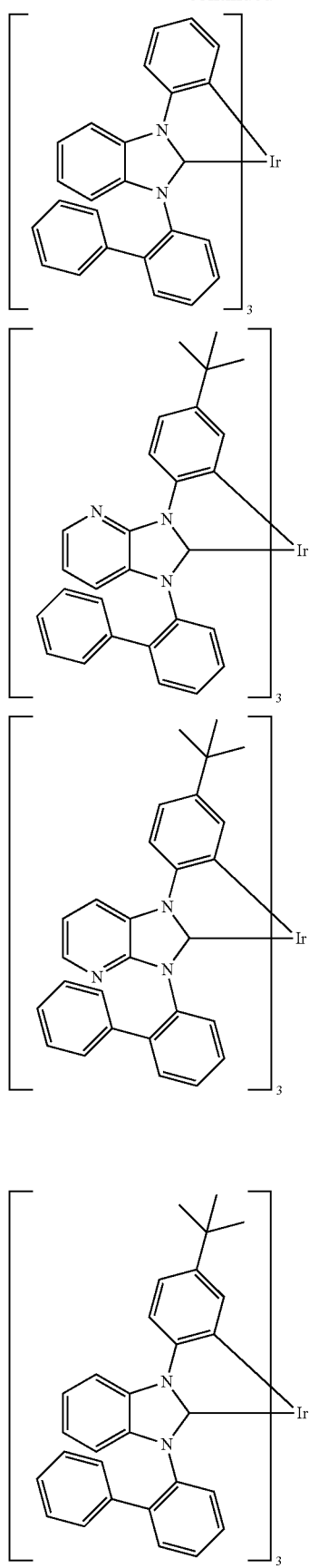
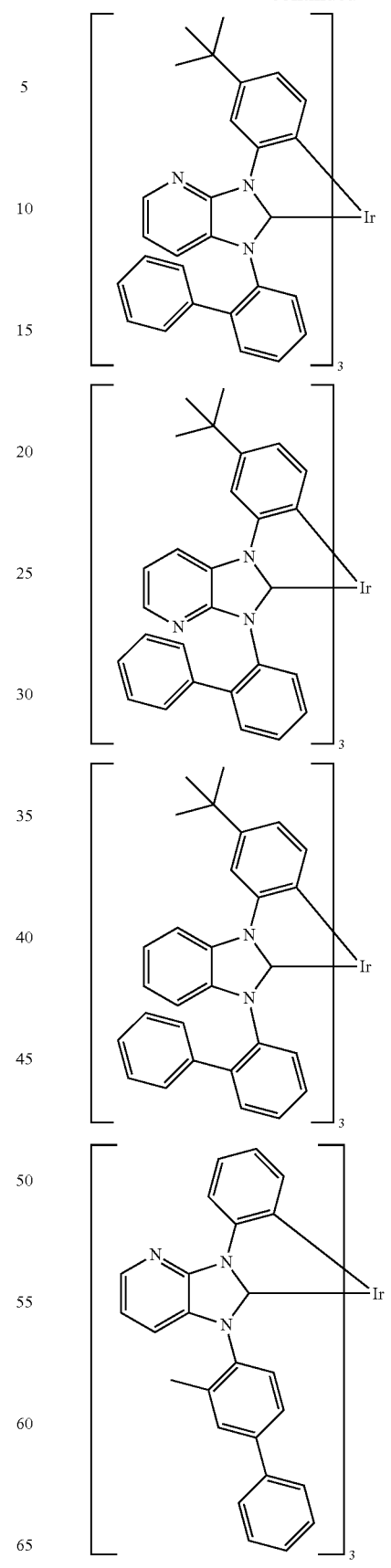

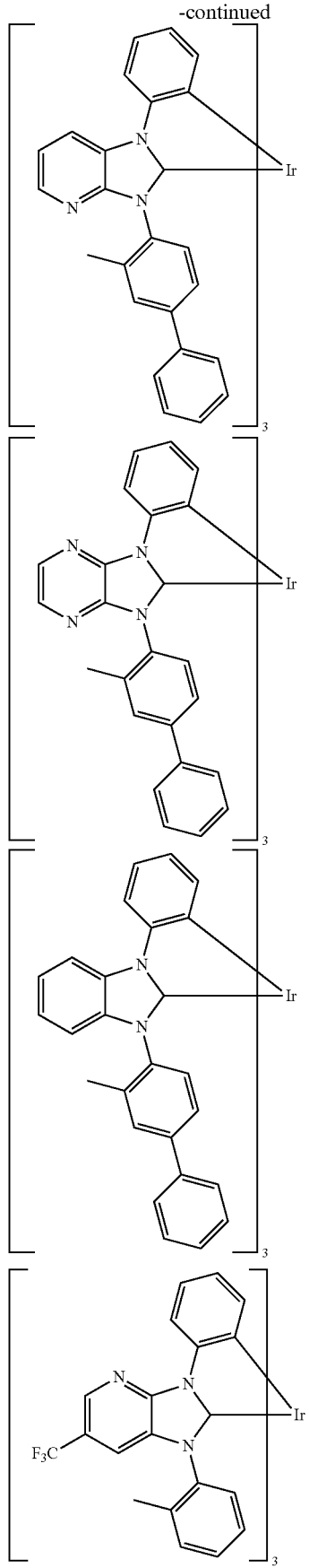
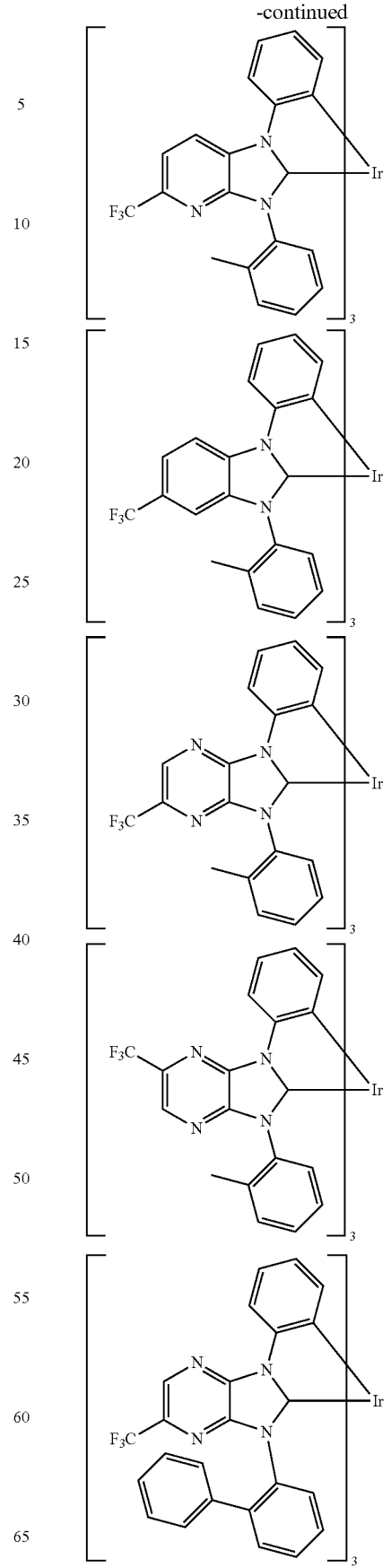

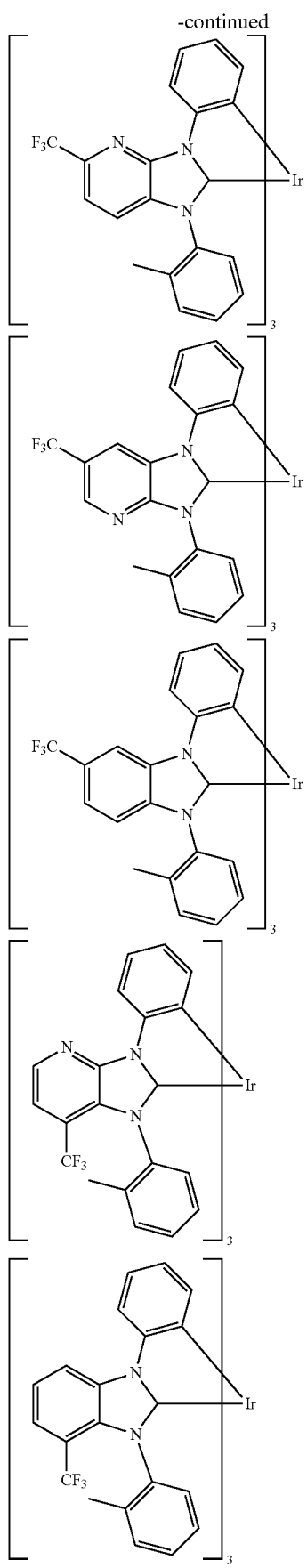
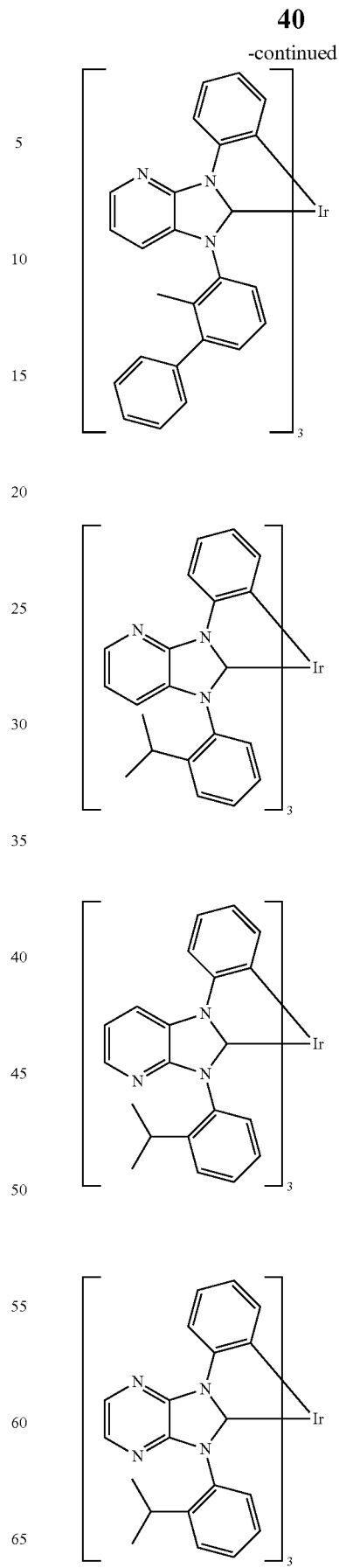

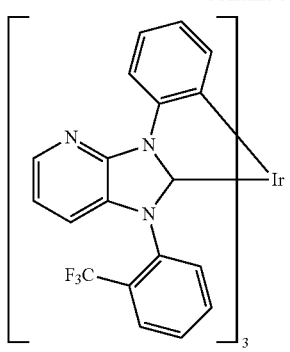
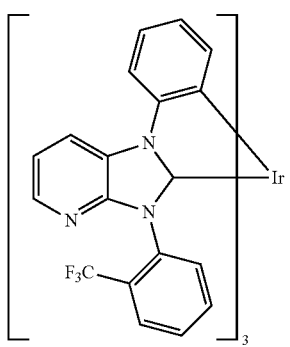
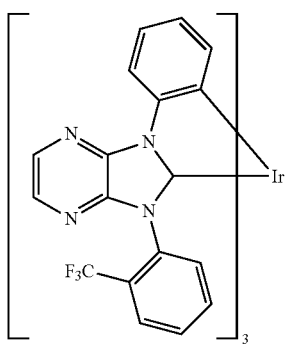
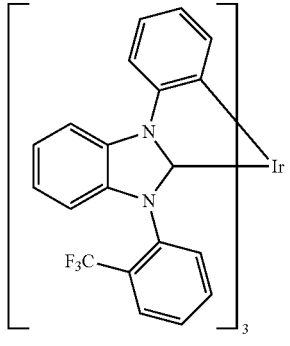
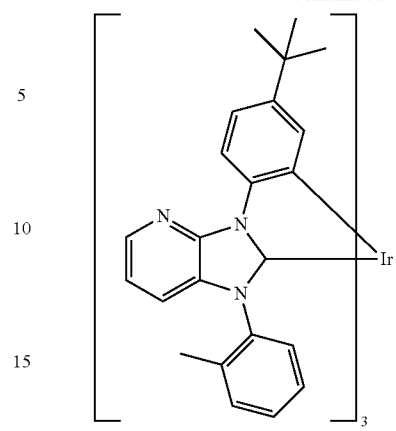
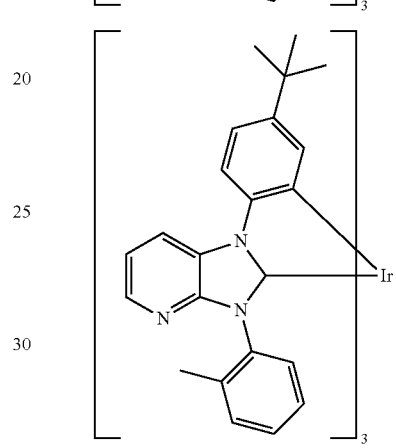
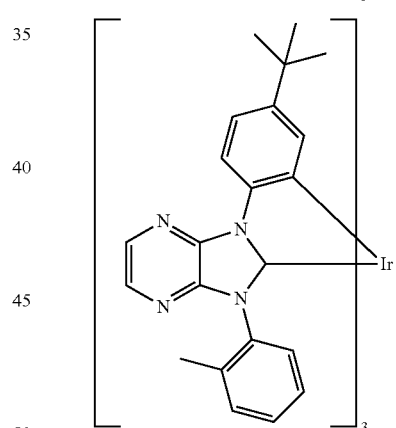
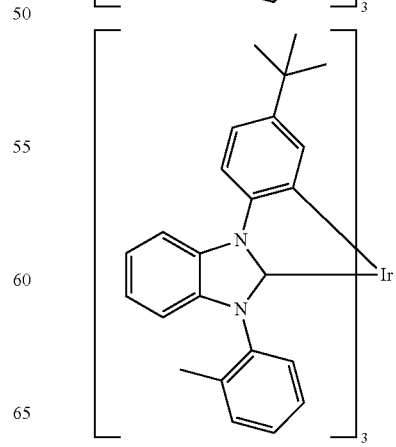

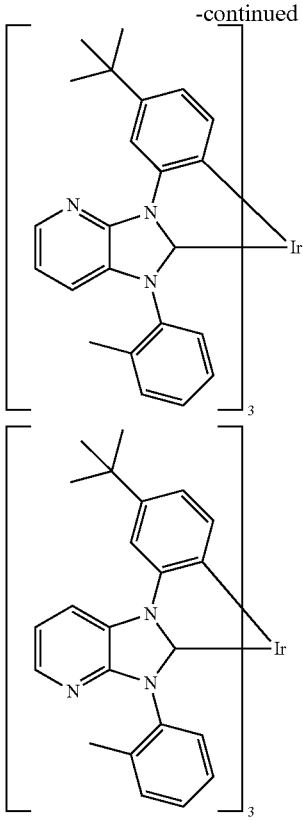
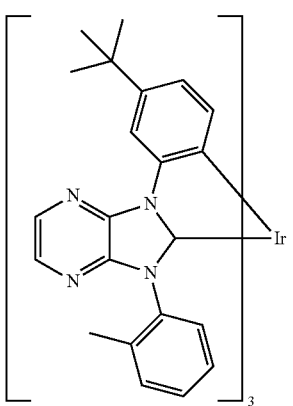
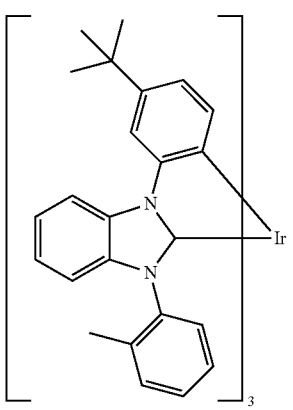
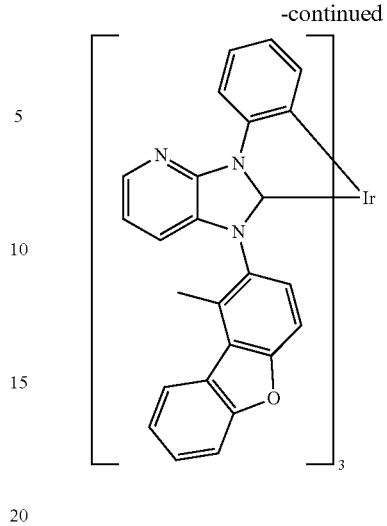
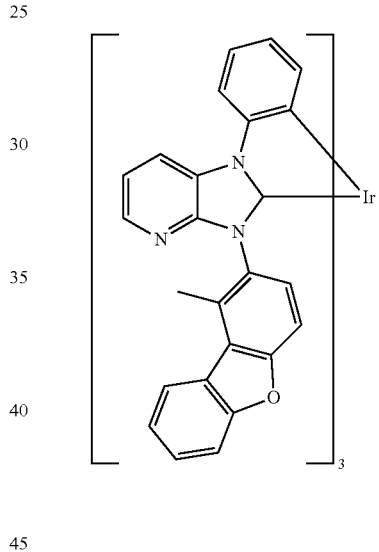
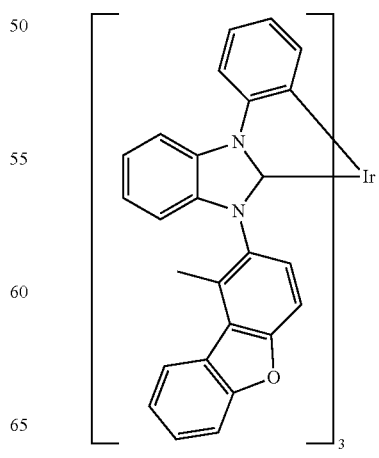

-continued
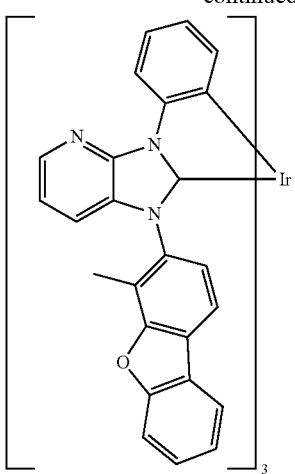
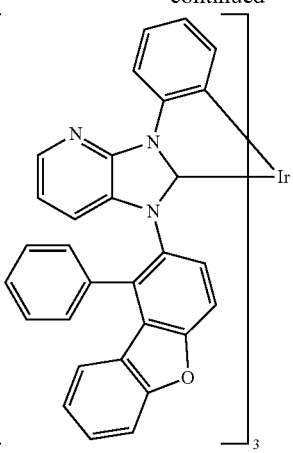
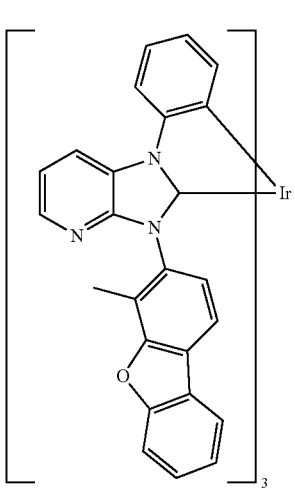
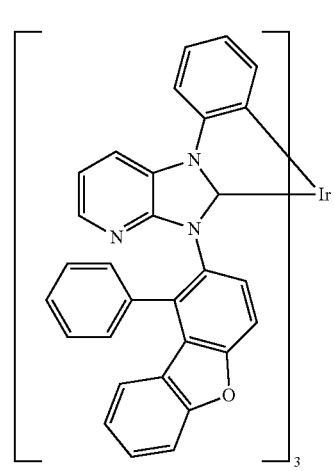
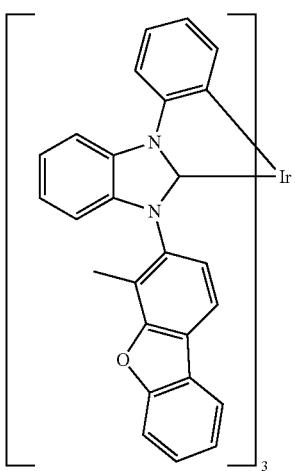
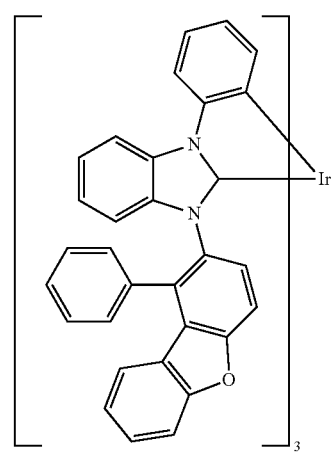

Most preferred inventive cyclometallated Ir complexes of formula (I) are the following complexes:
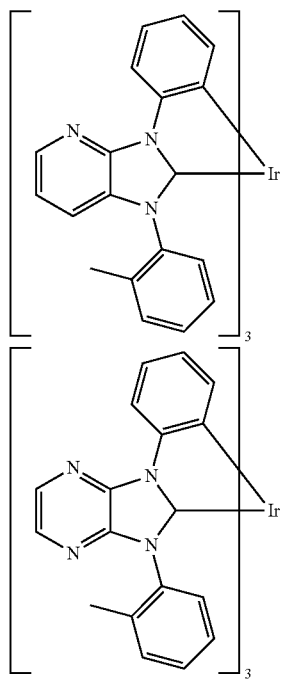
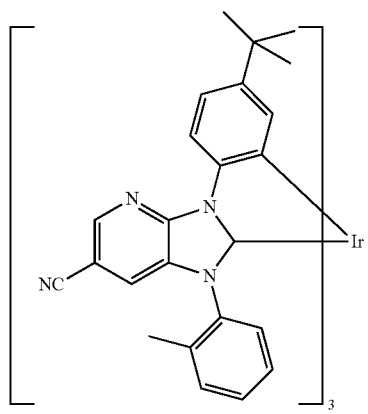
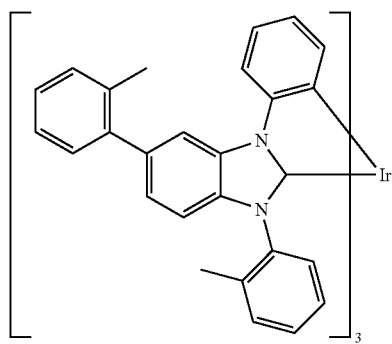
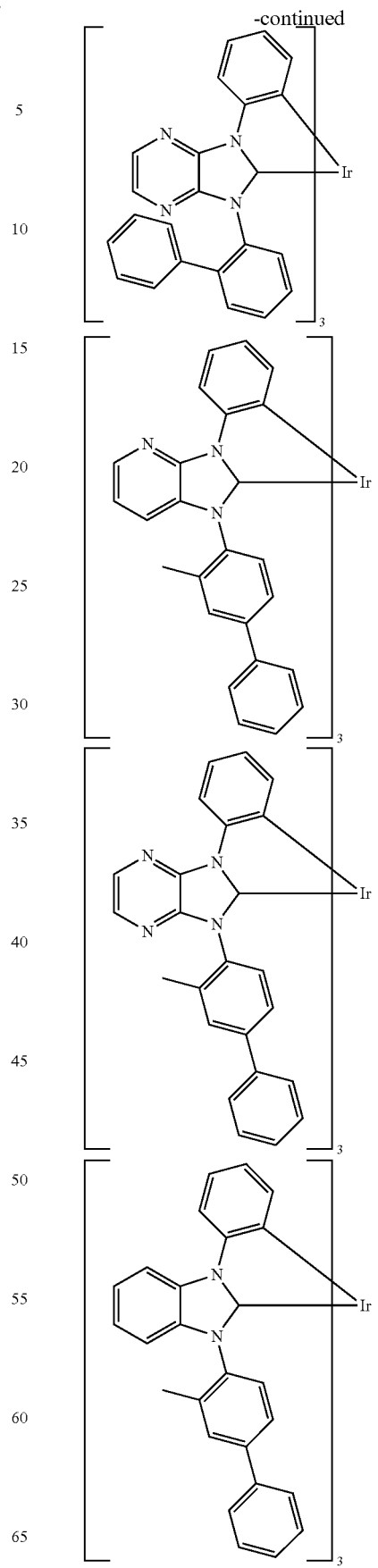

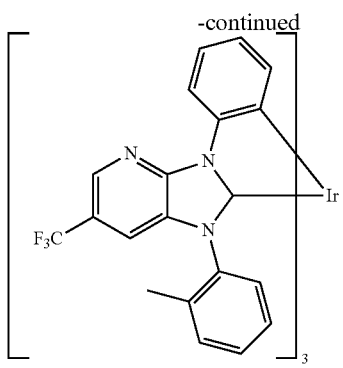

The present invention also relates to a process for preparing the inventive cyclometallated Ir complexes of formula (I) by contacting suitable compounds comprising Ir with the appropriate ligands or ligand precursors.

In one embodiment of the process according to the invention, a suitable compound comprising iridium and appropriate carbene ligands, preferably in deprotonated form as the free carbene or in the form of a protected carbene, for example as the silver-carbene complex, are contacted.

The present invention therefore relates—in one embodiment—to a process according to the invention wherein the ligand precursor used is a corresponding Ag-carbene complex.

In a further preferred embodiment of the process according to the invention, the ligand precursors used are organic compounds which are reacted with suitable Ir comprising compounds. The carbene can be released from precursors of the carbene ligands by removing volatile substances, for example lower alcohols such as methanol or ethanol, for example at elevated temperature and/or under reduced pressure and/or using molecular sieves which bind the alcohol molecules eliminated. Corresponding processes are known to those skilled in the art.

The present invention also relates to the process according to the invention wherein the ligand precursor used is a compound of the general formula (IV)

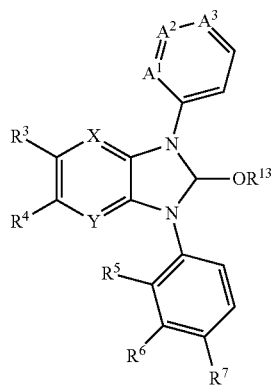

(IV)

wherein $A^1$, $A^2$, $A^3$, $R^3$, $R^4$, $R^6$, $R^5$, $R^7$, X and Y are each as already defined above for the compounds of the general formula (I), and $R^{13}$ is defined as follows:

$R^{13}$ is independently $SiR^{14}R^{15}R^{16}$, aryl, heteroaryl, alkyl, cycloalkyl or heterocycloalkyl, $R^{14}$, $R^{15}$, $R^{16}$ are each independently aryl, heteroaryl, alkyl, cycloalkyl or heterocycloalkyl.

The definitions of aryl, heteroaryl, alkyl, cycloalkyl and heterocycloalkyl have been specified above.

In a particularly preferred embodiment, $R^{13}$ is alkyl, especially $C_1$-$C_{20}$-alkyl, preferably $C_1$-$C_{10}$-alkyl, more preferably $C_1$-$C_8$-alkyl, for example methyl, ethyl, propyl such as n-propyl, isopropyl, butyl such as n-butyl, isobutyl, tert-butyl, pentyl, hexyl, heptyl or octyl.

$R^{13}$ in the compound of the general formula (IV) is most preferably methyl or ethyl.

Compounds of the general formula (IV) are generally obtainable by processes known to those skilled in the art. Compounds of the general formula (IV) can be obtained for example by reacting compounds of the general formula (Va)

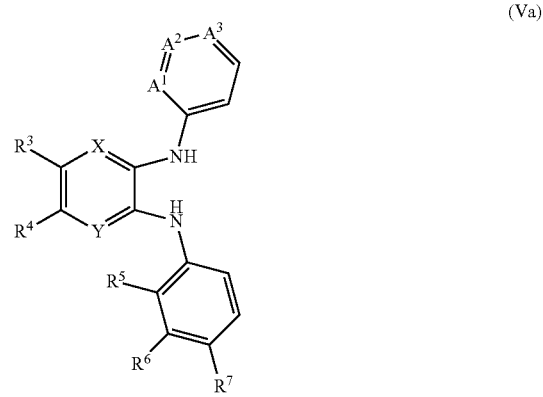

(Va)

or the corresponding Cl or $BF_4$ salt of formula (Vb)

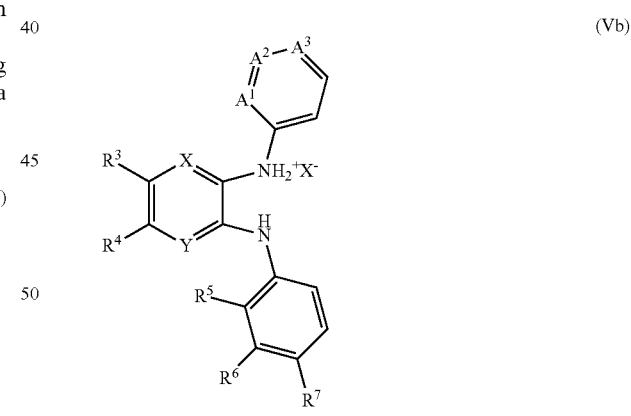

(Vb)

wherein $X^-$ is $Cl^-$ or $BF_4^-$, with compounds of the general formula (VI)

$$HC(OR^{13})_3 \qquad (VI),$$

or by reacting compounds of the general formula (Va) or (Vb) in a first step with Vilsmeier reagent ((chloromethylene) dimethylammonium chloride) and a sodium salt selected from $NaBF_4$, NaCl, NaBr or NaI to obtain a compound of formula (Vc)

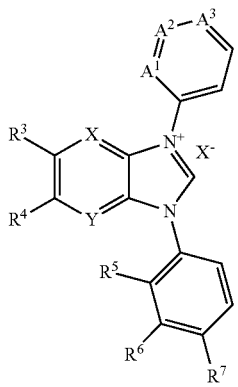

(Vc)

wherein X⁻ is $BF_4^-$, Cl⁻, Br or I⁻ and
in a second step with $R^{13}OH$ or $M''OR^{13}$, wherein M'' is an alkali metal salt, preferably Na,
and
where $A^1$, $A^2$, $A^3$, $R^3$, $R^4$, $R^6$, $R^5$, $R^7$, X, Y and $R^{13}$ are each as already defined above for the compounds of the general formula (IV) or for the cyclometallated Ir complexes of formula (I).

This preparation of the compounds of the general formula (IV) can be effected in the presence or in the absence of a solvent. Suitable solvents are specified below. In one preferred embodiment, the compounds of the general formula (IV) are prepared in substance, or the compound of the general formula (VI) is added in an excess, such that it functions as a solvent.

Compounds of the general formulae (Va), (Vb), (Vc) and (VI) are commercially available and/or obtainable by processes known to those skilled in the art; for example, compounds of the general formula (Va), (Vb), (Vc) are obtainable by reacting the appropriate chlorides with the appropriate amines.

The compounds of the general formula (IV) are prepared generally at a temperature of 10 to 150° C., preferably 40 to 120° C., more preferably 60 to 110° C.

The reaction time is generally 2 to 48 hours, preferably 6 to 24 hours, more preferably 8 to 16 hours.

After the reaction has ended, the desired product can be isolated and purified by customary processes known to those skilled in the art, for example filtration, recrystallization, column chromatography, etc.

Appropriate compounds, especially complexes comprising iridium, are known to those skilled in the art. Particularly suitable compounds comprising iridium comprise, for example, ligands such as halides, preferably chloride, 1,5-cyclooctadiene (COD), cyclooctene (COE), phosphines, cyanides, alkoxides, pseudohalides and/or alkyl.

Particularly preferred complexes comprising iridium are selected from the group consisting of $[Ir(COD)Cl]_2$, $[Ir(COE)_2Cl]_2$ $IrCl_3 \times H_2O$, $Ir(acac)_3$, $Ir(COD)_2BF_4$, $Ir(COD)_2$ BARF (BARF=tetrakis[3,5-bis(trifluoromethyl)phenyl]borate)) and mixtures thereof.

The carbene ligand precursors are deprotonated, preferably before the reaction, for example, by basic compounds known to those skilled in the art, for example basic metalates, basic metal acetates, acetylacetonates or alkoxides, or bases such as $KO^tBu$, $NaO^tBu$, $LiO^tBu$, NaH, silylamides, $Ag_2O$ and phosphazene bases. Particular preference is given to deprotonating with $Ag_2O$ to obtain the corresponding Ag-carbene, which is reacted with the compound comprising M to give the inventive complexes.

Particularly preferably, the carbene can be released from precursors of the carbene ligands by removing volatile substances, for example lower alcohols.

The process according to the invention for preparing the cyclometallated Ir complexes of formula (I) according to the present invention using the compounds of the general formula (IV) has the advantage that the compounds of the general formula (IV) are stable intermediates which can be handled readily and can be isolated under standard laboratory conditions. In addition, the compounds of the general formula (IV) are soluble in customary organic solvents, such that the preparation of the inventive cyclometallated Ir complexes of formula (I) in homogeneous solution is possible, such that a workup of the desired product, i.e. of the cyclometallated Ir complexes of formula (I) is more readily possible, for example for isolation and/or purification.

The contacting is preferably effected in a solvent. Suitable solvents are known per se to those skilled in the art and are preferably selected from the group consisting of aromatic or aliphatic solvents, for example benzene, toluene, xylene or mesitylene, cyclic or acyclic ethers, for example dioxane or THF, alcohols, esters, amides, ketones, nitriles, halogenated compounds and mixtures thereof. Particularly preferred solvents are toluene, xylenes, mesitylene and dioxane. The molar ratio of metal-noncarbene complex used to carbene ligand precursor used is generally 1:10 to 10:1, preferably 1:1 to 1:6, more preferably 1:3 to 1:5.

The contacting is generally effected at a temperature of 20 to 200° C., preferably 50 to 150° C., more preferably 60 to 150° C.

The reaction time depends on the desired carbene complex and is generally 0.02 to 50 hours, preferably 0.1 to 24 hours, more preferably 1 to 24 hours.

The cyclometallated Ir complexes of formula (I) obtained after the reaction can optionally be purified by processes known to those skilled in the art, for example washing, crystallization or chromatography.

The particular advantage of the process according to the present invention is the formation of only or mainly the mer isomer of the cyclometallated Ir complexes according to the present invention. This is due to the fact that asymmetric diaryl substituted carbene ligands bearing a substituent at the 2 position of one of the aryl residues bound to one of the carbene nitrogen atoms are present in the cyclometallated Ir complexes and the corresponding compounds of formulae (IV), (Va), (Vb) or (Vc) are used in the preparation of the cyclometallated Ir complexes. It has surprisingly been found by the inventors of the present invention that it is now possible to isolate the mer isomers of metal-carbene complexes having diaryl substituted carbene ligands as main products.

In the process of the present invention, the weight ratio of mer to fac isomer of the cyclometallated Ir complexes of formula (I) is in general 100%-50% (mer) to 0%-50% (fac), preferably, 100%-60% (mer) to 0%-40% (fac), more preferably 100%-75% (mer) to 0%-25% (fac).

It should be considered that it is in general not possible to convert the thermodynamically preferred fac isomer of cyclometallated Ir carbene complexes back into the mer isomer.

A further advantage of the process according to the present invention is the formation of only one or mainly one cyclometallation isomer of the cyclometallated Ir complexes according to the present invention. This is also due to the fact that asymmetric diaryl substituted carbene ligands bearing a substituent at the 2 position of one of the aryl residues bound to one of the carbene nitrogen atoms are present in the cyclometallated Ir complexes and the corresponding compounds of formulae (IV), (Va), (Vb) or (Vc) are used in the preparation of the cyclometallated Ir complexes. Since only one or mainly one cyclometallation isomer is present, the separation of the isomers which is usually accompanied by a loss of material associated with low yields is not necessary.

In a further embodiment, the present invention relates to an organic electronic device comprising at least one cyclometallated Ir complex according to the present invention.

Structures of the Organic Electronic Devices

Suitable structures of the organic electronic devices are known to those skilled in the art. Preferred organic electronic devices are selected from organic light-emitting diodes (OLED), light-emitting electrochemical cells (LEEC), organic photovoltaic cells (OPV) and organic field-effect transistors (OFET). More preferred organic electronic devices are OLEDs.

The organic light-emitting diode (OLED) is usually a light-emitting diode (LED) in which the emissive electroluminescent layer is a film of organic compound which emits light in response to an electric current. This layer of organic semiconductor is usually situated between two electrodes. Generally, at least one of these electrodes is transparent. The cyclometallated Ir complex of formula (I) may be present in any desired layer, preferably in the emissive electroluminescent layer (light-emitting layer), of the OLED as emitter material.

The light-emitting electrochemical cell (LEEC) is usually a solid-state device that generates light from an electric current (electroluminescence). LEEC's are usually composed of two metal electrodes connected by (e.g. sandwiching) an organic semiconductor containing mobile ions. Aside from the mobile ions, their structure is very similar to that of an organic light-emitting diode (OLED). The cyclometallated Ir complex of formula (I) may be present in any desired layer as emitter material.

The organic field-effect transistor (OFET) generally includes a semiconductor layer formed from an organic layer with hole transport capacity and/or electron transport capacity; a gate electrode formed from a conductive layer; and an insulation layer introduced between the semiconductor layer and the conductive layer. A source electrode and a drain electrode are mounted on this arrangement in order thus to produce the transistor element. In addition, further layers known to those skilled in the art may be present in the organic transistor. The cyclometallated Ir complex of formula (I) may be present in any desired layer.

The organic photovoltaic cell (OPV) (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is usually formed from two sublayers, i.e. a layer with p-type semiconductor character or hole transport capacity, and a layer formed with n-type semiconductor character or electron transport capacity. In addition, it is possible for further layers known to those skilled in the art to be present in the organic solar cell. The cyclometallated Ir complex of formula (I) may be present in any desired layer, of the OPV, preferably as absorption dye.

The organic electronic device is most preferably an OLED or LEEC or OPV, wherein the cyclometallated Ir complex of formula (I) is preferably employed in the light-emitting layer and or hole transport layer, more preferably as emitter material in OLEDs or LEECs, preferably OLEDs, or as absorption dye in OPVs. The organic electronic device is most preferably an OLED, wherein the cyclometallated Ir complex of formula (I) is employed in the light-emitting layer and/or hole transport layer. Even more preferably, the metal-carbene complex of formula (I) is employed as emitter material.

The present invention therefore preferably relates to an organic electronic device which is an OLED, wherein the OLED comprises (a) an anode,
(b) a cathode,
(c) a light-emitting layer between the anode and the cathode,
(d) optionally a hole transport layer between the light-emitting layer and the anode, wherein the cyclometallated Ir complex of formula (I) is present in the light-emitting layer and/or—if present—in the hole transport layer of the OLED.

The structure of the inventive OLED will be described in detail below.

Cyclometallated Ir Complex of Formula (I) as Emitter Material

According to the present invention, the cyclometallated Ir complexes of formula (I) are employed in an organic electronic device, preferably in an OLED. More preferably, the cyclometallated Ir complexes of formula (I) are employed as emitter material, preferably as emitter material in the light-emitting layer of an OLED. Suitable OLEDs are known in the art and the preferred structures of suitable OLEDs are described above and—in more detail—below.

The cyclometallated Ir complexes of formula (I) are preferably phosphorescence emitter showing emission of light by phosphorescence. However, this does not exclude that the phosphorescence emitter additionally shows emission of light by fluorescence.

The phosphorescence emitter show phosphorescence emission from triplet excited states, preferably at the operating temperatures of the OLED. Generally, the operating temperatures of the OLED are −40 to +90° C. Phosphorescence may be preceded by a transition from a triplet excited state to an intermediate non-triplet state from which the emissive decay occurs.

The emission decay time (intensity reduced to $1/e=0.367879441$ times its initial value) $\tau_0$ to of the luminescence emission of the cyclometallated Ir complex of formula (I) is preferably of from 0.1 to 20 micro seconds, more preferably of from 0.1 to 10 micro seconds, most preferably of from 0.1 to 4 micro seconds.

The mer complexes of the present invention are characterized by very short emission decay times compared with the corresponding fac isomers. The emission decay time of the mer complexes $\tau_0$ to is in many cases half as long as the emission decay time of the corresponding fac complexes.

The emission decay time of the complexes of formula (I), wherein X is N; and Y is $CR^8$, preferably CH, or N is in a particularly preferred embodiment 0.1 to 2 micro seconds, even more preferably 0.1 to 1.5 micro seconds.

Further Emitter Materials

The cyclometallated Ir complex of formula (I) may be employed alone as the only emitter material or in a mixture with one or more cyclometallated Ir complexes of formula (I) and/or one or more further emitter materials, preferably in the light-emitting layer of an OLED. Suitable further emitter materials are known by a person skilled in the art.

Suitable further emitter materials are for example:

Phosphorescence emitter compounds based on metal complexes, and especially the complexes of the metals Ru, Rh, Ir, Pd and Pt, in particular the complexes of Ir Suitable metal complexes for use in the inventive organic electronic device, preferably in the OLEDs, are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO 2010/086089, WO 2012/121936 A2, US 2011/0057559, WO 2011/106344, US 2011/0233528 and WO 2011/157339, WO2008156879, WO2010068876, US20110233528, WO2012048266, WO2013031662, WO2013031794.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)(pyridinato-N,C$^{3'}$)(acetylacetonate), tris(2-phenylquinoline)iridium(III), iridium(III) bis(2-(4,6-difluorophenyl)pyridinato-N,C$^{2}$)picolinate, iridium(III) bis(1-phenylisoquinoline)(acetylacetonate), bis(2-phenylquinoline)(acetylacetonato)iridium(III), iridium(III) bis(dibenzo[f,h]quinoxaline)-(acetylacetonate), iridium(III) bis(2-methyldibenzo[f,h]quinoxaline)(acetylacetonate), bis [1-(9,9-dimethyl-9H-fluoren-2-yl)isoquinoline](acetylacetonato)iridium(III), bis(2-phenylbenzo-thiazolato)(acetylacetonato)iridium(III), bis(2-(9,9-dihexylfluorenyl)-1-pyridine)(acetyl-acetonato)iridium(III), bis(2-benzo[b]thiophen-2-ylpyridine)(acetylacetonato)iridium(III).

Preferred further phosphorescence emitters are carbene complexes. Carbene complexes which are suitable phosphorescent blue emitters are specified in the following publications: WO 2006/056418 A2, WO 2005/113704, WO 2007/115970, WO 2007/115981, WO 2008/000727, WO2009050281, WO2009050290, WO2011051404, US2011/057559 WO2011/073149, WO2012/121936A2, US2012/0305894A1, WO2012170571, WO2012170461, WO 2012170463, WO2006121811, WO2007095118, WO2008156879, WO2008156879, WO2010068876, US20110057559, WO2011106344, US20110233528, WO2012048266 and WO2012172482.

Preferably, the cyclometallated Ir complex of formula (I) is employed alone—as the only emitter material, preferably in the light-emitting layer of an OLED.

Host Material

The cyclometallated Ir complex of formula (I) or the mixture of emitter materials mentioned above may be employed, preferably in the light-emitting layer of an OLED, without further additional components or with one or more further components in addition to the emitter material. For example, a fluorescent dye may be present in the light-emitting layer of an OLED in order to alter the emission color of the emitter material. In addition—in a preferred embodiment—one or more host (matrix) material can be used. This host material may be a polymer, for example poly(N-vinylcarbazole). The host material may, however, likewise be a small molecule, for example 4,4'-N,N'-dicarbazolebiphenyl (CDP=CBP) or tertiary aromatic amines, for example TCTA.

Suitable as host material are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the host materials specified in the following applications: WO2008/034758, WO2009/003919.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO201004433A2 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709, European patent applications EP12175635.7 and EP12185230.5 and EP12191408.9 (in particular page 25 to 29 of EP12191408.9), WO2012048266, WO2012145173, WO2012162325, and EP2551932.

In a particularly preferred embodiment, one or more compounds of the general formula (IX) specified hereinafter are used as host material:

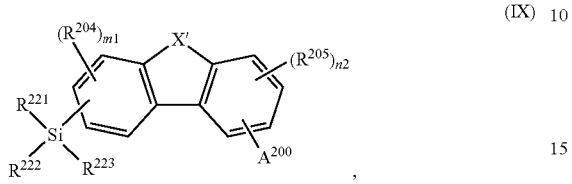
(IX)

wherein

X' is NR, S, O or PR;

R is aryl, heteroaryl, alkyl, cycloalkyl, or heterocycloalkyl;

$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;

$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;

$R^{204}$ and $R^{205}$ are independently of each other alkyl, cycloalkyl, heterocycloalkyl, aryl, heteroaryl, a group $A^{200}$, or a group having donor, or acceptor characteristics;

n2 and m1 are independently of each other 0, 1, 2, or 3;

$R^{206}$, $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl.

Compounds of formula (IX) and their preparation processes, such as, for example,

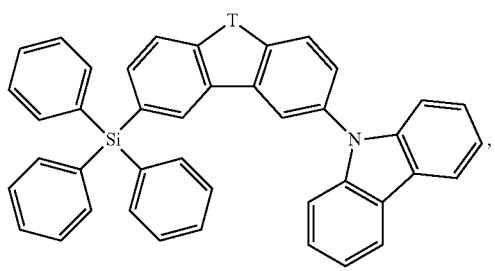

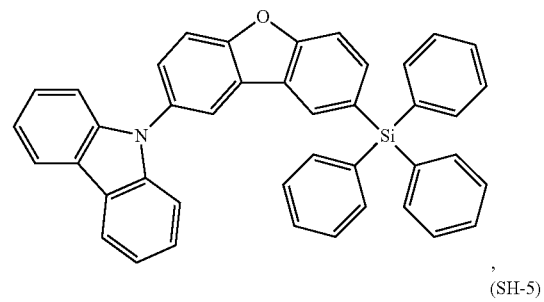
(SH-4)

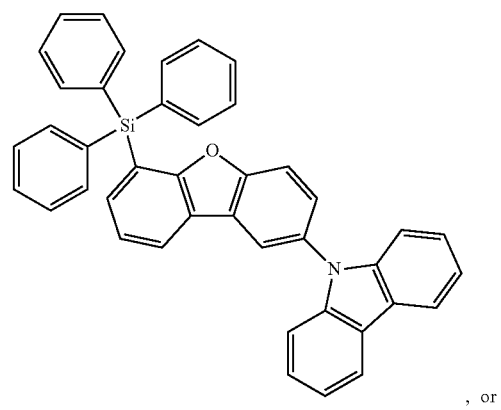
(SH-5)

, or

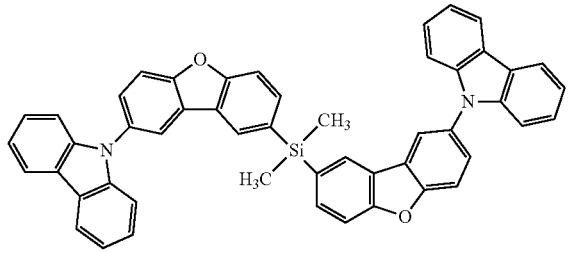
(SH-6)

are described in WO 2010/079051 A1 (in particular pages on 19 to 26 and in tables on pages 27 to 34, pages 35 to 37 and pages 42 to 43).

Additional host materials on basis of dibenzofurane are, for example, described in US 2009066226, EP1 885 818 B1, EP 1 970 976, EP 1 998 388 and EP 2 034 538. Examples of particularly preferred host materials are shown below:

-continued
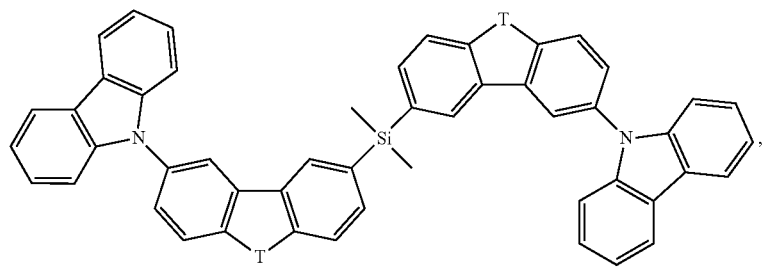
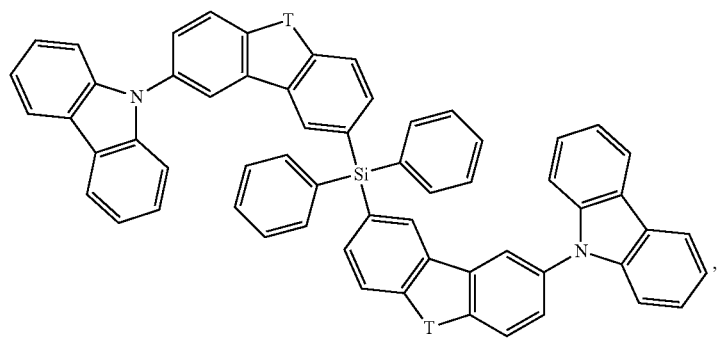
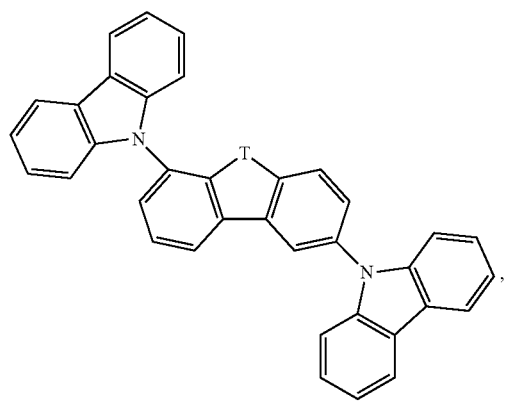
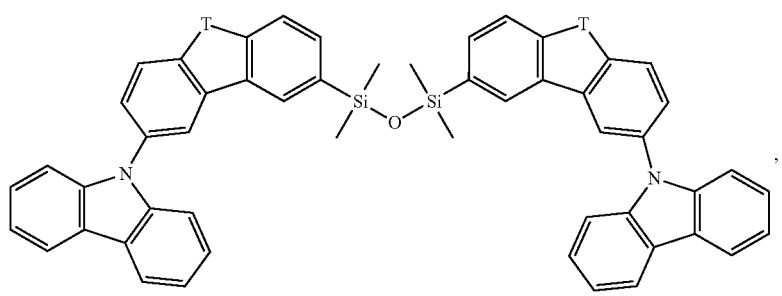

-continued
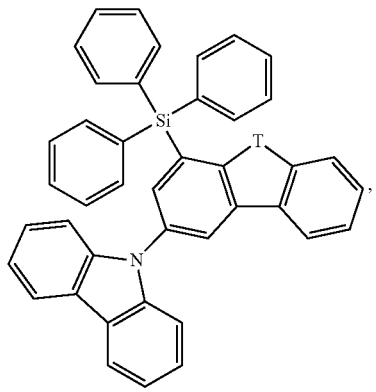
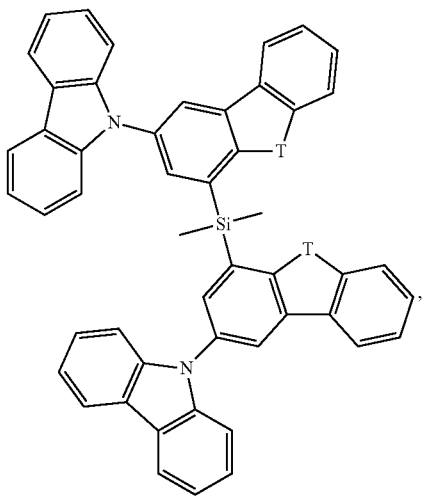
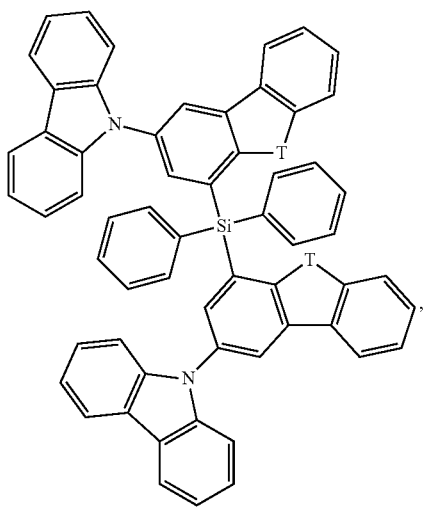
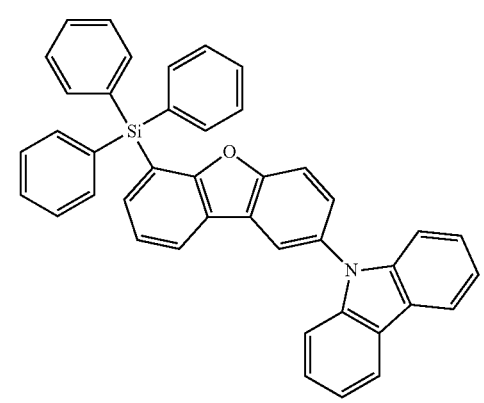
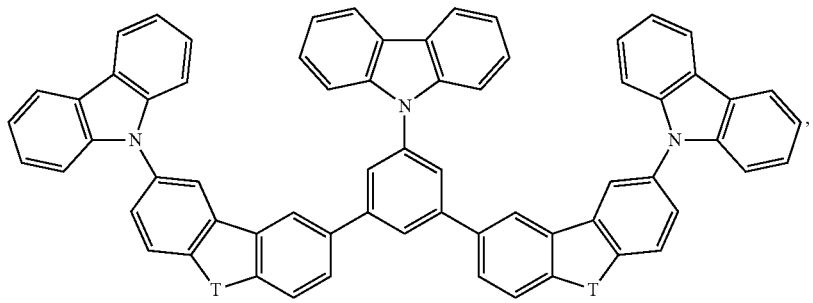
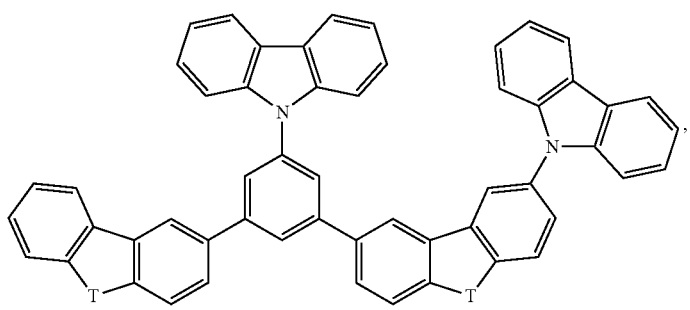

-continued
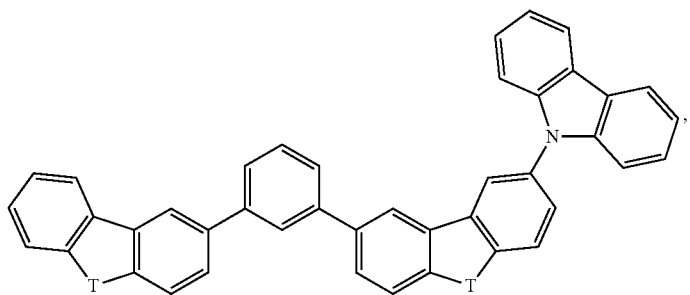
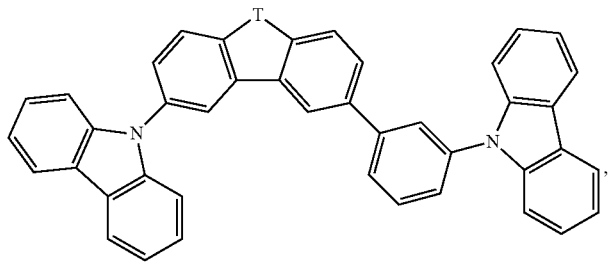
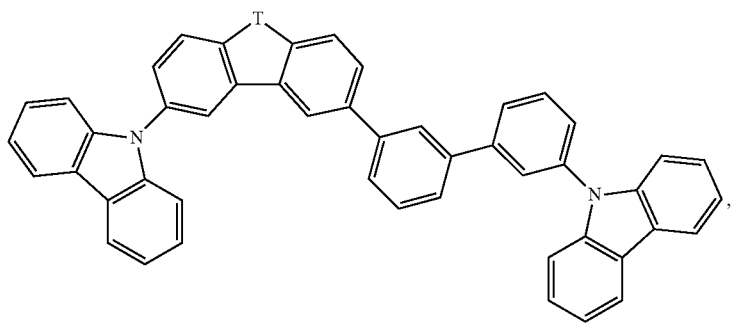
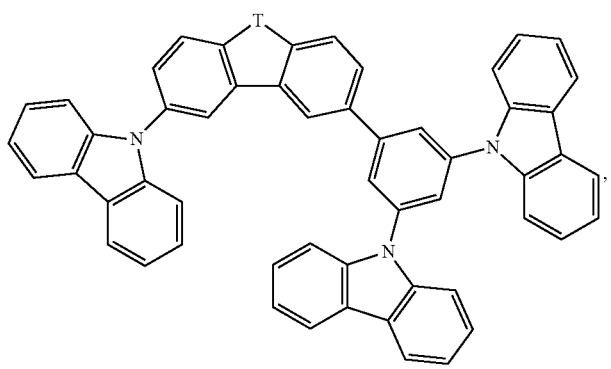
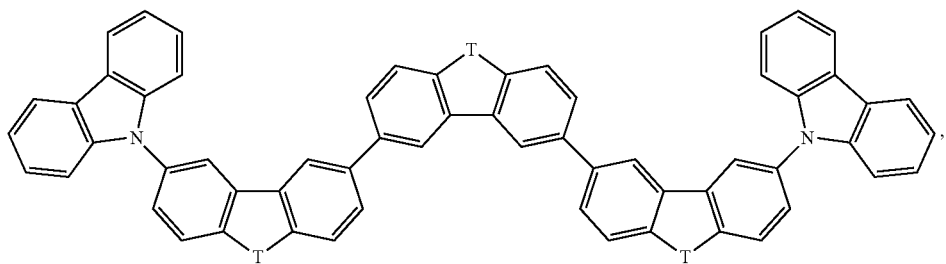

-continued
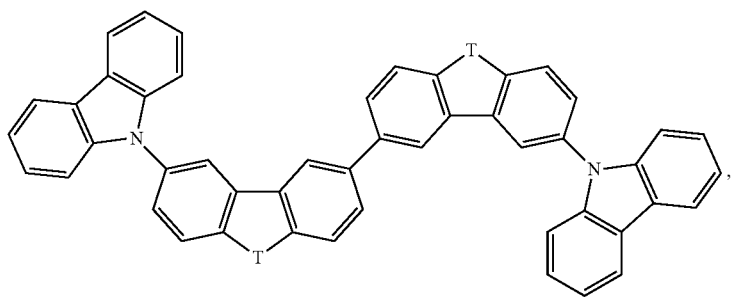
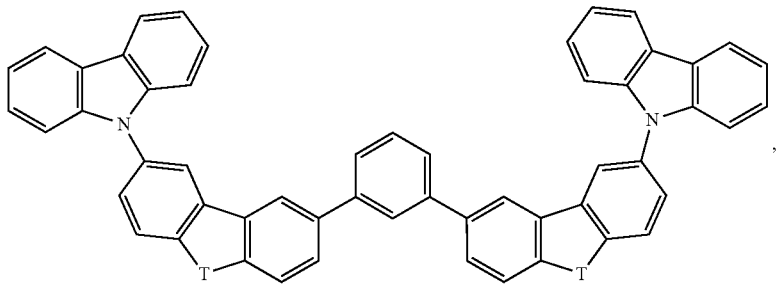
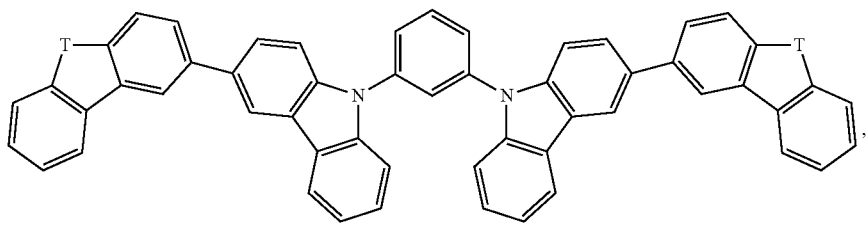
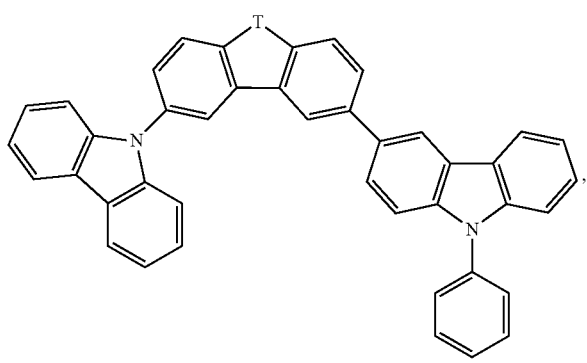
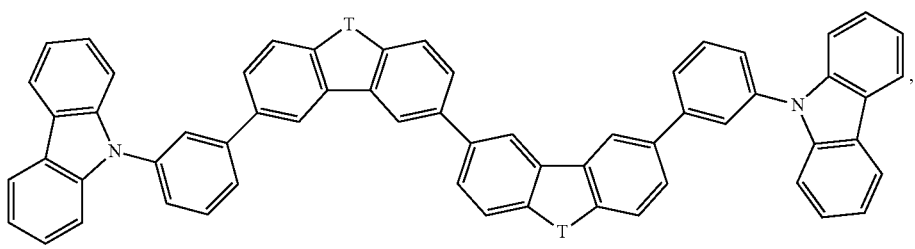

-continued
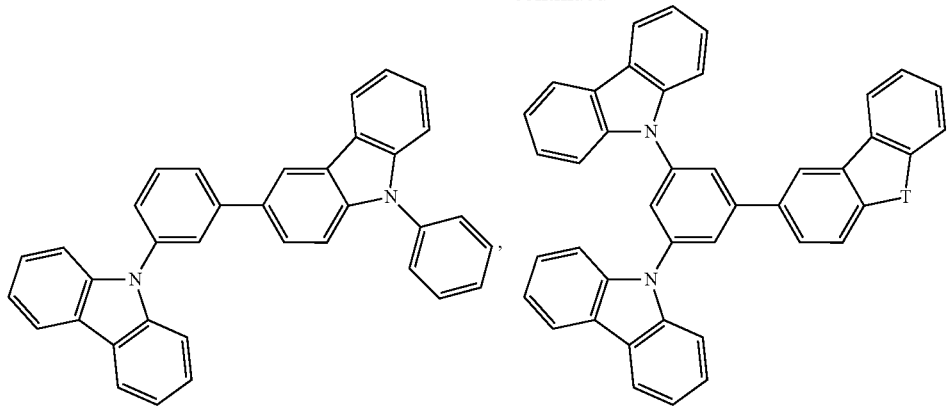
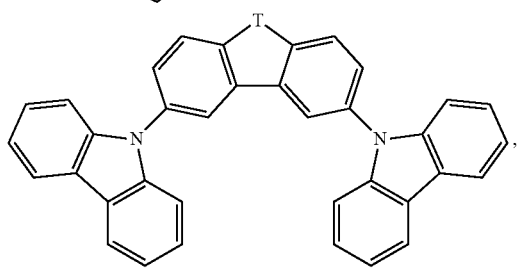
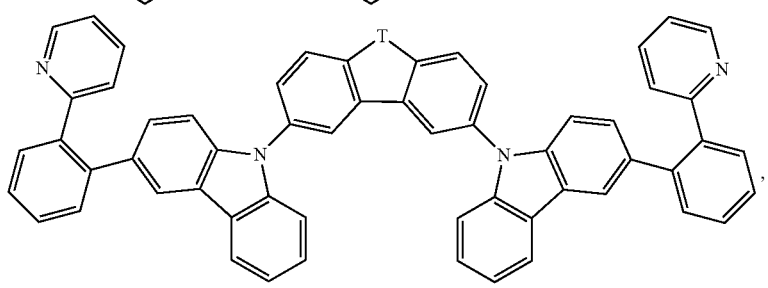
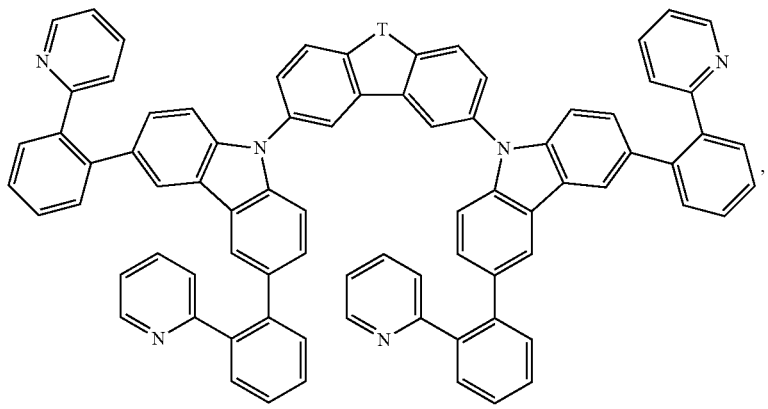
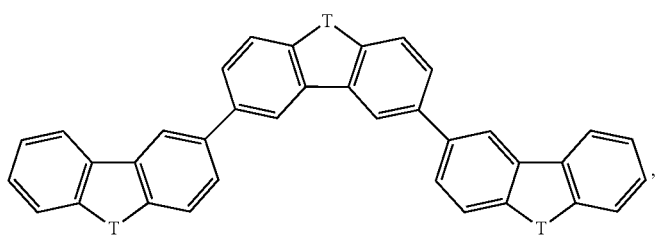

-continued
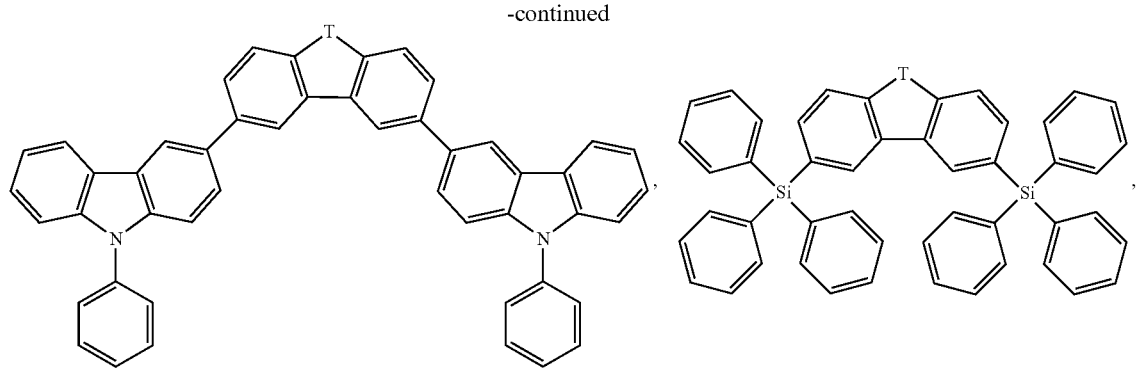
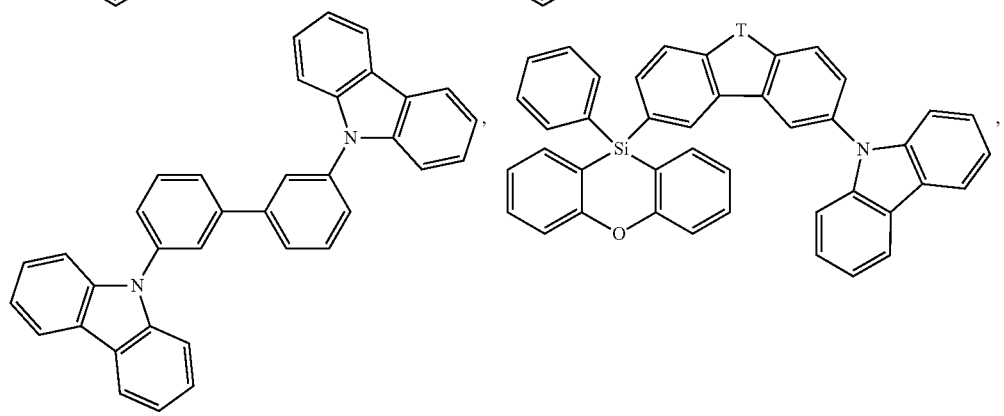
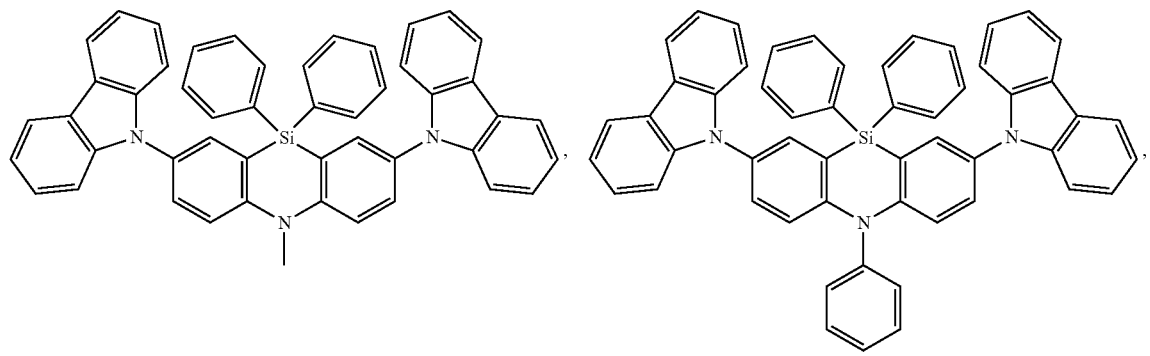
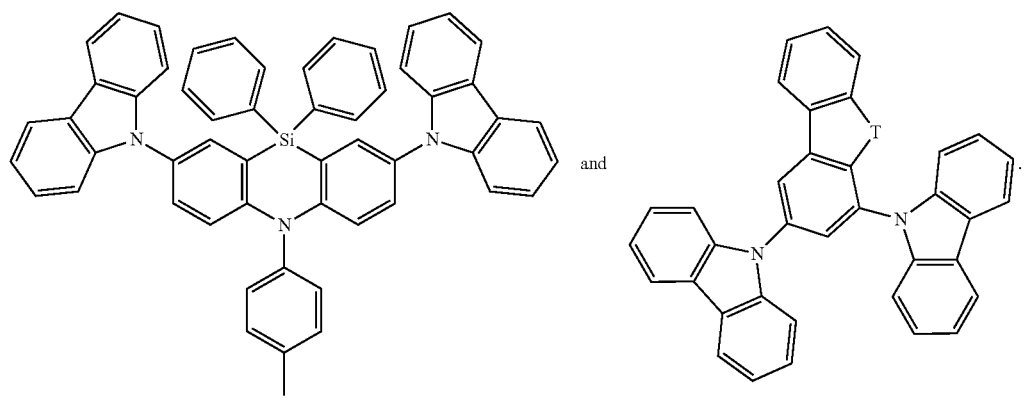
and
In the above-mentioned compounds T is O, or S, preferably O. If T occurs more than one time in a molecule, all groups T have the same meaning.

The more preferred host compounds are shown below:
(SH-1)
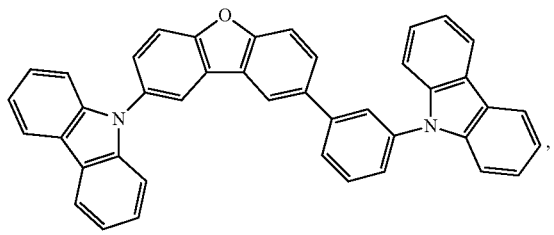
(SH-2)
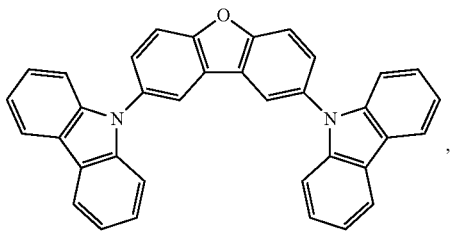
(SH-3), (SH-4), (SH-5), (SH-6)
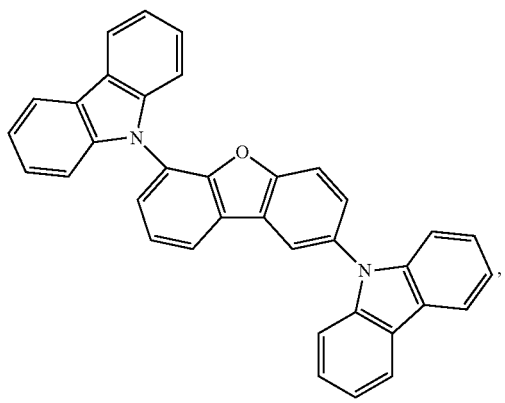
(SH-7a)
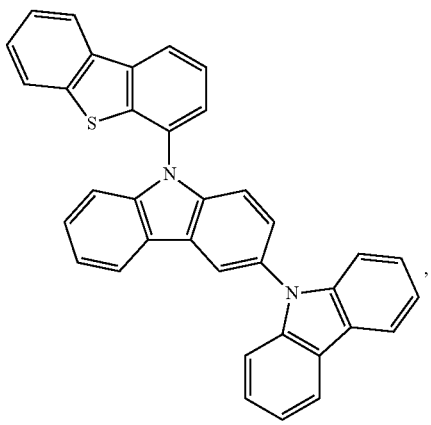
(SH-7b)
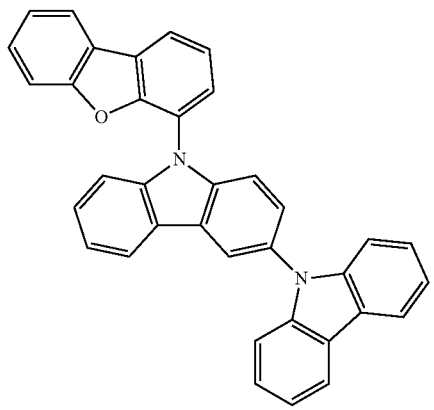
(SH-8)
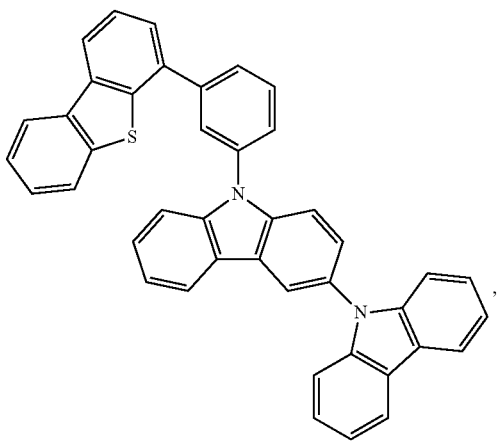
(SH-9)
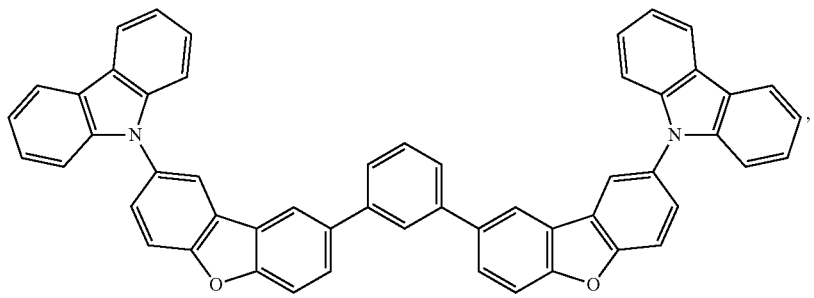

-continued
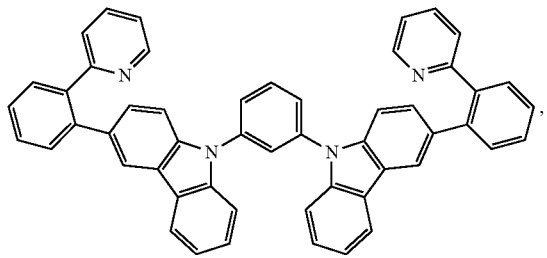
(SH-10)
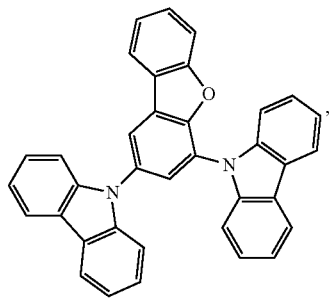
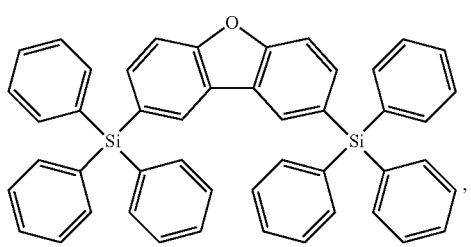
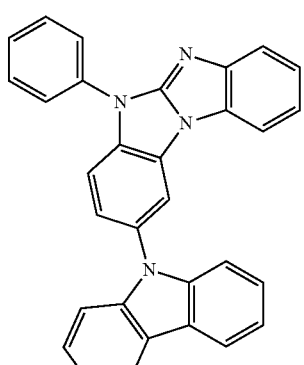
(SH-11)
(SH-12)
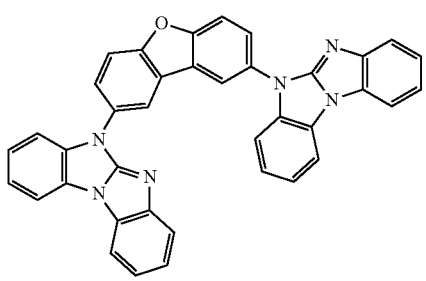
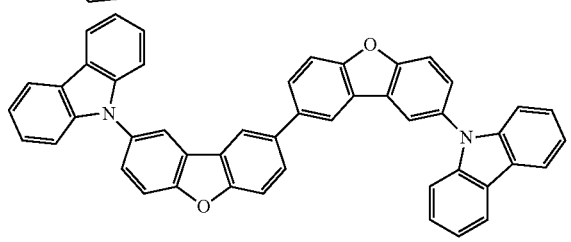
(SH-13; published in WO 2011/004639, compound I-8)
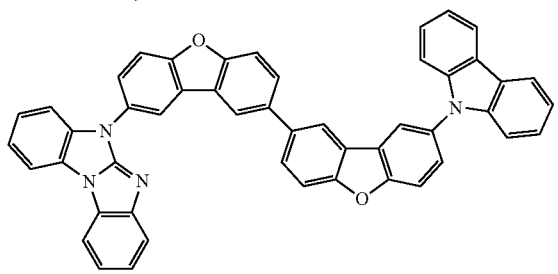
(published in WO2012/130709)
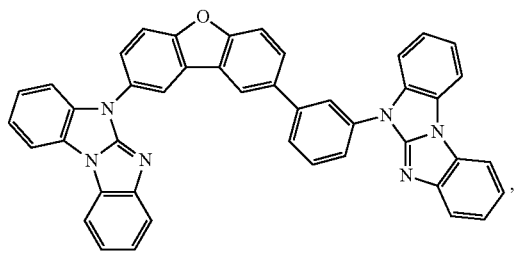
(published in WO2012/130709)
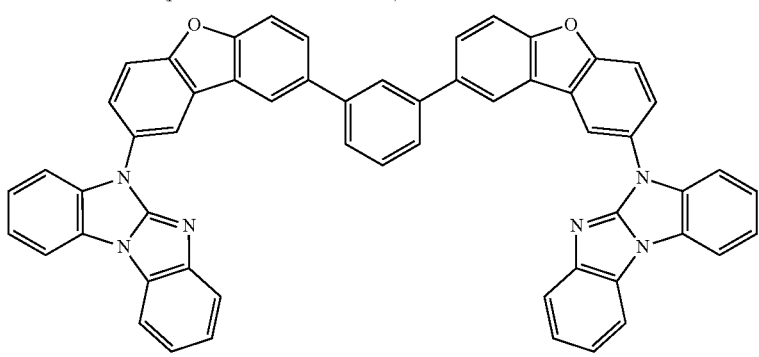
(published in WO2012/130709)

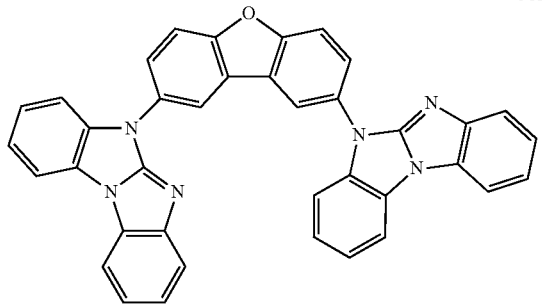
(published in WO2012/130709)
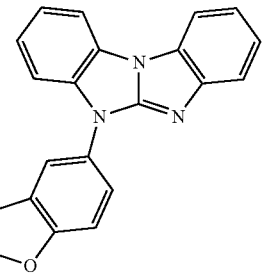
(published in WO2012/130709)
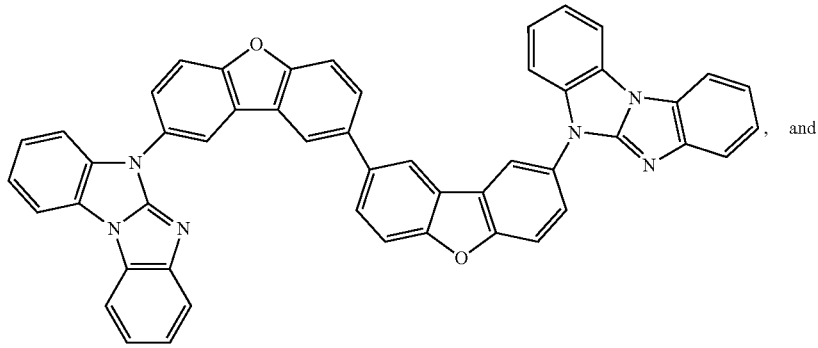, and
(published in WO2012/130709)
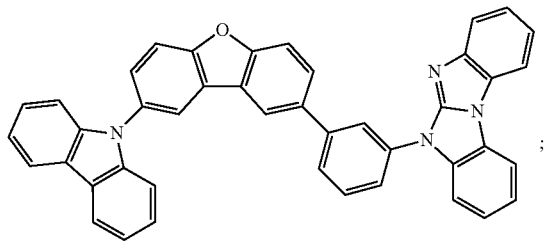;
(published in WO2012/130709)
as well as the host materials published in WO2012048266, WO2012145173, WO2012162325, and EP2551932.
The most preferred host compounds are shown below:
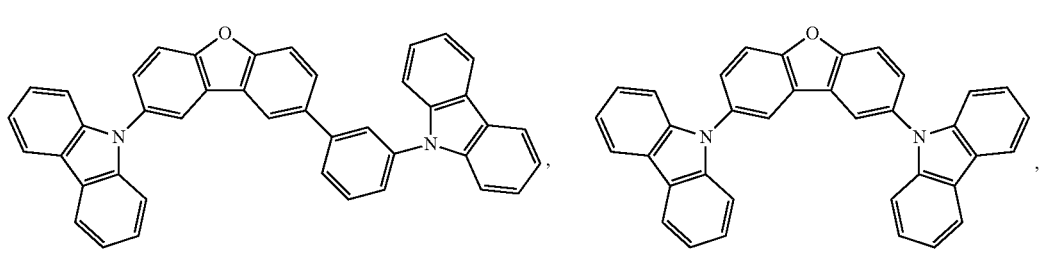
(SH-1; published in WO 2009/008100, example 4)
(SH-2)

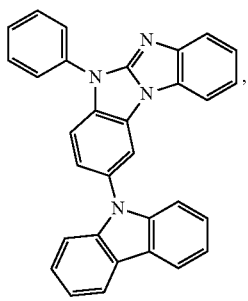

(SH-11; disclosed in EP12175635.7 and US61/669677)

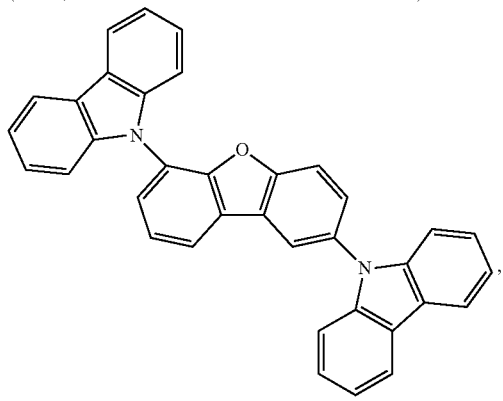

(published in WO 2011/004639, compound I-1, synthesis described in [0163])

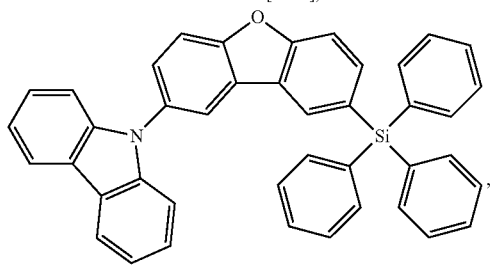

(SH-4, published in WO 2010/079051, compound 14)

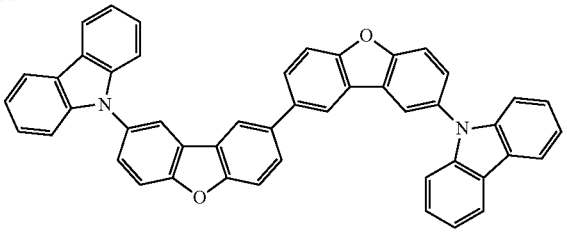

(SH-13; published in WO 2011/004639, compound I-8)

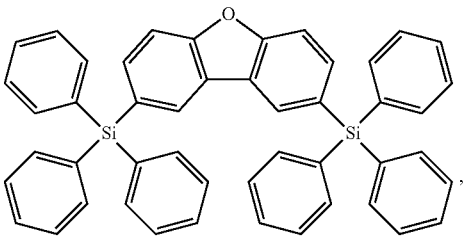

(published in WO2009/003898, compound 4g)

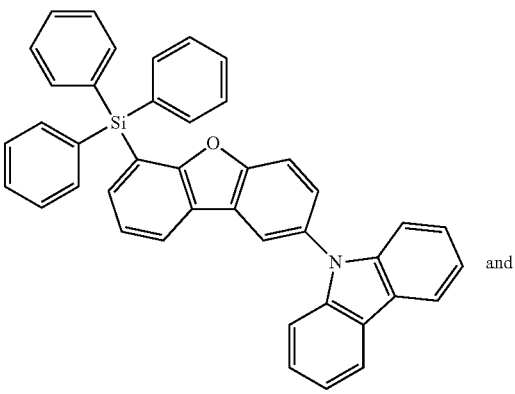

and (SH-5, published in WO 2010/079051, structure on page 22, X = O)

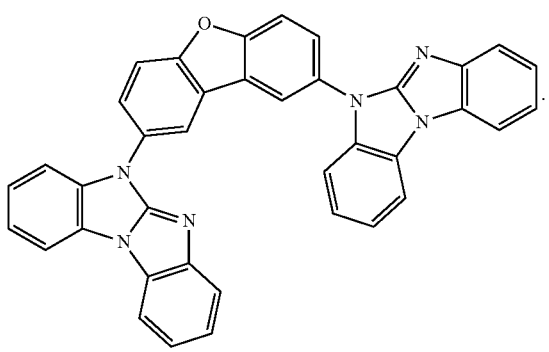

(SH-12; published in WO 2012/130709)

The present invention therefore also concerns the organic electronic device, preferably the OLED, according to the present invention, wherein the at least one cyclometallated Ir complex of formula (I) is employed in combination with at least one host material. Suitable and preferred host materials are mentioned above.

More preferably, the at least one host material comprises at least one dibenzofuranyl unit and/or at least one benzimidazo[1,2-a]benzimidazolyl unit and/or at least one carbazolyl and/or at least one dibenzothiofuranyl unit. Suitable host materials and preferred host materials comprising at least one dibenzofuranyl unit and/or at least one benzimidazo[1,2-a]benzimidazolyl unit and/or at least one carbazolyl and/or at least one dibenzothiofuranyl unit are mentioned above. The at least one cyclometallated Ir complex of formula (I) which is employed in combination with at least one host material is preferably employed in the light-emitting layer of an OLED.

Preferably, the light-emitting layer comprises at least one emitter material, which is a cyclometallated Ir complex of formula (I) according to the present invention, and at least one host material. Suitable and preferred emitter materials as well as suitable and preferred host materials are mentioned above.

Most preferably, the organic electronic device, preferably the OLED, comprises a light-emitting layer comprising at least one cyclometallated Ir complex of formula (I) as emitter material in an amount of 5 to 40% by weight, preferably 5 to 30% by weight, more preferably 5 to 20 by weight, and at least one host material or at least one host material and at least one co-host material as described below, wherein preferred host materials are mentioned above and preferred co-hosts are mentioned below, in an amount of 60 to 95% by weight, preferably 70 to 95% by weight, more preferably 80 to 95% by weight (the amount is either the amount of the at least one host or the amount of the sum of the at least one host and the at least one co-host—the ratio of at least one host to at least one co-host is given below), where the amount of the at least one emitter material and the at least one host material or the at least one host material and the at least one co-host, adds up to a total of 100% by weight.

The light-emitting layer may comprise a second host compound (co-host). The second host compound can be one compound or it can be a mixture of two or more compounds. Ir carbene complexes, preferably the Ir carbene complexes Ir(DPBIC)$_3$, Ir(DPABIC)$_3$ or Ir(DPABIC)$_2$(DPBIC) which are described below, may be added as second host.

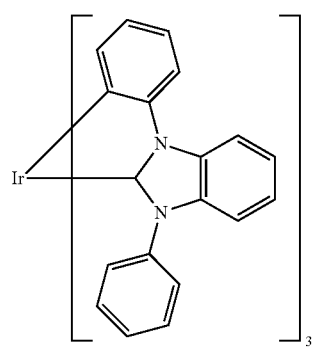

Ir(DPBIC)$_3$ (as described in WO 2005/019373A2)

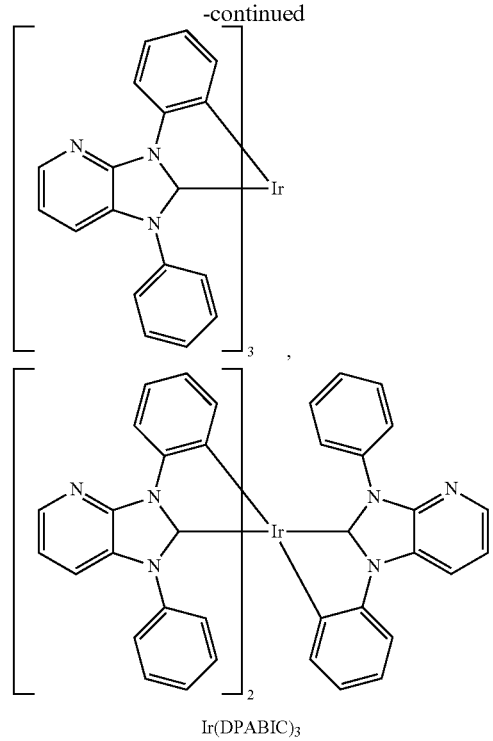

Ir(DPABIC)$_3$ (as described as complex Em1 in WO2012/172182 (synthesis: example 1) and in the not yet published EP application EP 13162776.2)

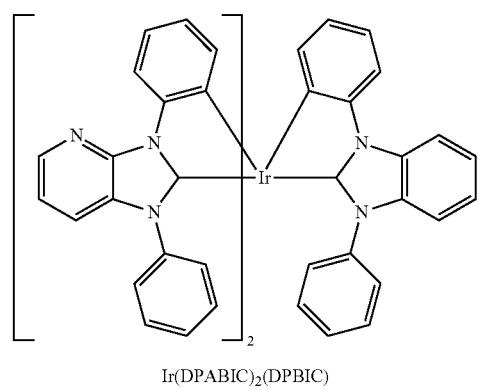

Ir(DPABIC)$_2$(DPBIC)

(as described as complex Em10 in WO2012/172482 (synthesis: example 10)).

Mixed matrix materials with two hosts selected from those hosts mentioned above, or one host from those hosts mentioned above and one co-host as described above, comprise preferably 5% by weight to 15% by weight of at least one, preferably one, co-host and 60% by weight to 90% by weight of a further host selected from the hosts as mentioned above.

The layer thickness of the light-emitting layer in the inventive OLED is preferably from 1 to 100 nm, more preferably 5 to 60 nm. Preferred OLED structures are mentioned above and—in more detail—below.

Device Structure—OLED Structure

Suitable structures of the organic electronic devices are known to those skilled in the art. Preferred organic electronic devices are selected from organic light-emitting diodes (OLED), light-emitting electrochemical cells (LEEC), organic photovoltaic cells (OPV) and organic field-effect transistors (OFET). More preferred organic electronic devices are OLEDs.

The device structures of said OLEDs, LEECs, OPVs and OFETs have been described above in general terms. In the following, the device structures of preferred OLEDs (which are preferred electronic devices according to the present invention) are described.

As mentioned above, the present invention preferably relates to an organic electronic device which is an OLED, wherein the OLED comprises
(a) an anode,
(b) a cathode,
(c) a light-emitting layer between the anode and the cathode,
(d) optionally a hole transport layer between the light-emitting layer and the anode,
wherein the cyclometallated Ir complex of formula (I) is present in the light-emitting layer and/or—if present—in the hole transport layer of the OLED.

Preferred cyclometallated Ir complexes of formula (I) are mentioned before.

The layer sequence in the inventive OLED is preferably as follows:
1. anode (a)
2. hole-transport layer (d)
3. electron/exciton blocking layer (e)
4. light-emitting layer (c)
5. cathode (b)

Layer sequences different from the aforementioned construction are also possible, and are known to those skilled in the art. For example, it is possible that the OLED does not have all of the layers mentioned; for example, an OLED with the layers (a) (anode), (c) (light-emitting layer) and (b) (cathode) and layer (d) (hole-transport layer) or layer (e) (electron/exciton blocking layer) are likewise suitable.

The OLEDs may additionally have a blocking layer for holes/excitons (f) adjacent to the cathode side of the light-emitting layer (c) and/or an electron transport layer (g) adjacent to the cathode side of the blocking layer for holes/excitons (f), if present, respectively adjacent to the cathode side of the light-emitting layer (c), if the blocking layer for holes/excitons (f) is not present.

The present invention therefore more preferably relates to an inventive OLED having the following layer sequence:
1. anode (a)
2. hole-transport layer (d)
3. electron/exciton blocking layer (e)
4. light-emitting layer (c)
5. blocking layer for holes/excitons (f)
6. electron transport layer (g)
7. cathode (b)

In a further embodiment, the inventive OLED, in addition to layers (a), (b), (c), (d), (e), (f) and (g), comprises at least one of the further layers mentioned below:
A hole injection layer (h) between the anode (a) and the hole-transport layer (d);
an electron injection layer (i) between the electron-transport layer (g) and the cathode (b).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole-transport layer should be matched to the work function of the anode, and the LUMO (lowest unoccupied molecular orbital) of the electron conductor layer should be matched to the work function of the cathode, provided that the aforementioned layers are present in the inventive OLEDs.

Hole-Transport Material (d) and/or the Electron/Exciton Blocker Material (e)

The hole-transport material and/or the electron/exciton blocker material in the OLED of the present invention may be an Ir metal-carbene complex comprising one, two or three, preferably three, bidentate ligands of formula (III) and/or (III')

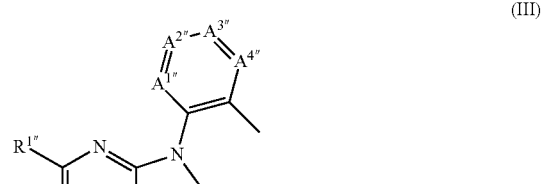

(III)

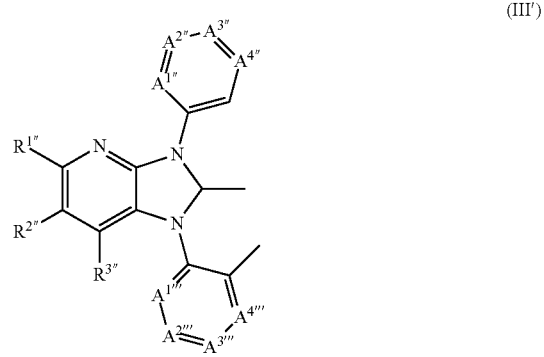

(III')

wherein

R$^{1''}$, R$^{2''}$ and R$^{3''}$ are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably, R$^{1''}$, R$^{2''}$ and R$^{3''}$ are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, preferably F or Cl, more preferably F; CF$_3$, SiPh$_3$ and SiMe$_3$;

or

R$^{1''}$ and R$^{2''}$ or R$^{2''}$ and R$^{3''}$ form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;

A$^{1''}$ is CR$^{4''}$ or N, preferably CR$^{4''}$;
A$^{2''}$ is CR$^{5''}$ or N, preferably CR$^{5''}$;
A$^{3''}$ is CR$^{6''}$ or N, preferably CR$^{6''}$;
A$^{4''}$ is CR$^{7''}$ or N, preferably CR$^{7''}$;
A$^{1'''}$ is CR$^{4'''}$ or N, preferably CR$^{4'''}$;
A$^{2'''}$ is CR$^{5'''}$ or N, preferably CR$^{5'''}$;
A$^{3'''}$ is CR$^{6'''}$ or N, preferably CR$^{6'''}$;
A$^{4'''}$ is CR$^{7'''}$ or N, preferably CR$^{7'''}$;
R$^{4''}$, R$^{5''}$, R$^{6''}$, R$^{7''}$, R$^{4'''}$, R$^{5'''}$, R$^{6'''}$ and R$^{7'''}$ are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having from 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably, R$^{4''}$, R$^{5''}$, R$^{6''}$, R$^{7''}$, R$^{4'''}$, R$^{5'''}$, R$^{6'''}$ and R$^{7'''}$ are each independently hydrogen, a linear or branched alkyl radical, optionally bearing at least one functional group, optionally interrupted by at least one heteroatom and having a total of from 1 to 20 carbon and/or heteroatoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from halogen radicals, preferably F or Cl, more preferably F; CF$_3$, CN, SiPh$_3$ and SiMe$_3$;

or

R$^{4''}$ and R$^{5''}$, R$^{5''}$ and R$^{6''}$ or R$^{6''}$ and R$^{7''}$ or R$^{4'''}$ and R$^{5'''}$, R$^{5'''}$ and R$^{6'''}$ or R$^{6'''}$ and R$^{7'''}$ form, independently of each other, together with the carbon atoms to which they are bonded, a saturated or unsaturated or aromatic, optionally substituted ring, which is optionally interrupted by at least one heteroatom, has a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms.

Preferred Ir metal-carbene complexes suitable as hole-transport materials and/or the electron/exciton blocker materials in the OLED of the present invention are described in detail in the EP application No. 13162776.2.

In the case that the OLED comprises a material different from the materials mentioned before in the hole-transport layer or in the electron/exciton blocking layer, suitable materials are mentioned below.

Hole-Transport Layer (d)

Further suitable hole-transport materials for layer (d) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transport material. Customarily used hole-transporting molecules are selected from the group consisting of

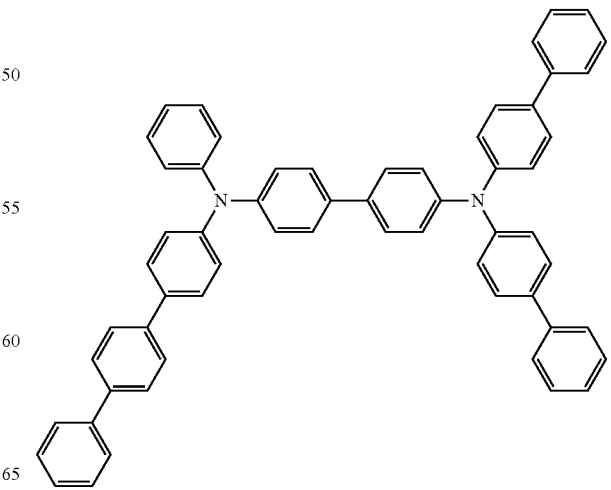

(4-phenyl-N-(4-phenylphenyl)-N-[4-[4-(N-[4-(4-phenyl-phenyl)phenyl]anilino)phenyl]phenyl]aniline),

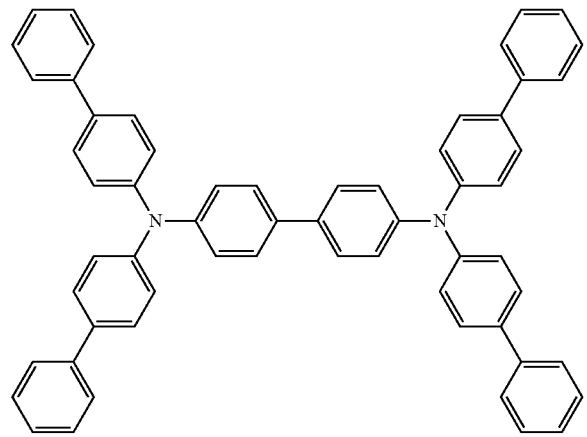 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

(4-phenyl-N-(4-phenylphenyl)-N-[4-[4-(4-phenyl-N-(4-phenylphenyl)anilino)phenyl]phenyl]aniline),

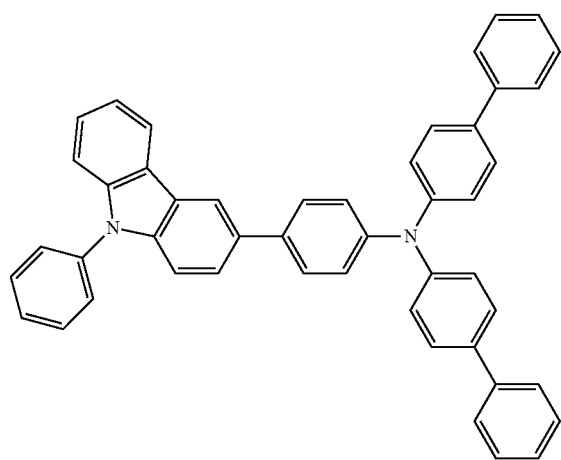 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazol-3-yl)phenyl]-N-(4-phenylphenyl)aniline),

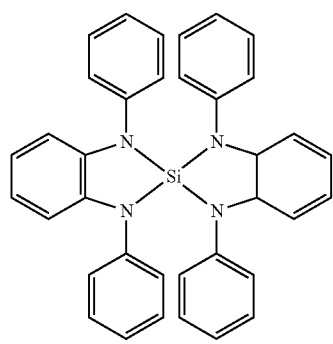 [SMILES: C1=CC2C(C=C1)N(c1ccccc1)[Si]1(N(c3ccccc3)c3ccccc3N1c1ccccc1)N2c1ccccc1]

1,1',3,3'-tetraphenylspiro[1,3,2-benzodiazasilole-2,2'-3a,7a-dihydro-1,3,2-benzodiazasilole],

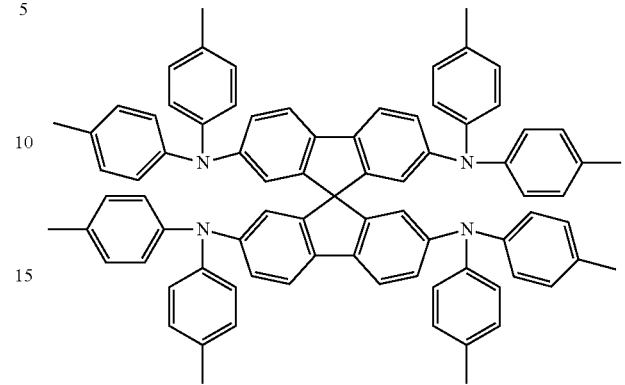

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (αNPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9H-fluorene, benzidine compounds such as N,N'-bis(naphthalen-1-yl)-N,N'-bis(phenyl)benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

The hole-transport materials mentioned above are commercially available and/or prepared by processes known by a person skilled in the art.

In a preferred embodiment it is possible to use specific metal carbene complexes as hole-transport materials. Suitable carbene complexes are, for example, carbene complexes as described in WO2005/019373A2, WO2006/056418 A2, WO2005/113704, WO2007/115970, WO2007/115981 and WO2008/000727. One example of a suitable carbene complex is Ir(DPBIC)$_3$ with the formula:

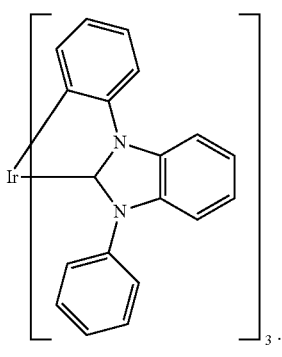

The preparation of Ir(DPBIC)₃ is for example mentioned in WO 2005/019373 A2.

Another example of a suitable carbene complex is Ir(DPABIC)₃

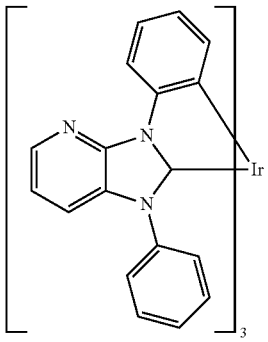

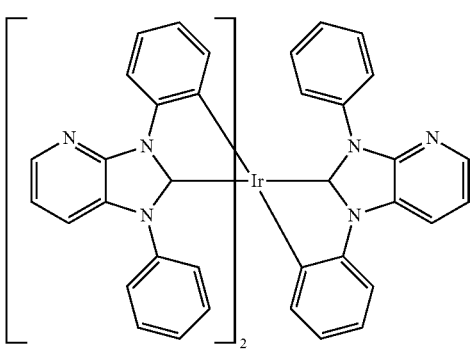

The preparation of Ir(DPABIC)₃ is for example mentioned in WO2012/172182 (complex Em1; synthesis: example 1)).

Another example of a suitable carbene complex is

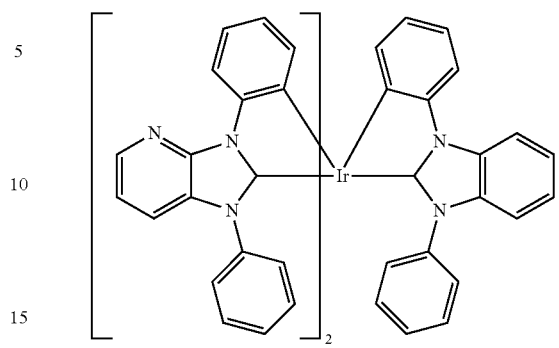

Ir(DPABIC)₂(DPBIC)

The preparation of Ir(DPABIC)₂(DPBIC) is for example mentioned in WO2012/172482 (complex Em10 in (synthesis: example 10)).

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide as doping material, for example $MoO_2$, $MoO_3$, $WO_x$, $ReO_3$ and/or $V_2O_5$, preferably $MoO_3$ and/or $ReO_3$, more preferably $MoO_3$ or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium) tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-tetracyanoquinodimethane, dicyanomethylene-1,3,4,5,7,8-hexafluoro-6H-naphthalen-2-ylidene)malononitrile ($F_6$-TNAP), Mo(tfd)₃ (from Kahn et al., J. Am. Chem. Soc. 2009, 131 (35), 12530-12531), compounds as described in EP1988587 and in EP2180029 and quinone compounds as mentioned in EP 09153776.1.

Preferably, the hole-transport layer comprises 50 to 90% by weight, of the hole-transport material and 10 to 50% by weight of the doping material, wherein the sum of the amount of the hole-transport material and the doping material is 100% by weight.

Electron/Excitors Blocking Layer (e)

Blocking layers may also be used to block excitons from diffusing out of the emissive layer.

Further suitable metal complexes for use as electron/exciton blocker material are, for example, carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application. One example of a suitable carbene complex is Ir(DPBIC)$_3$ with the formula:

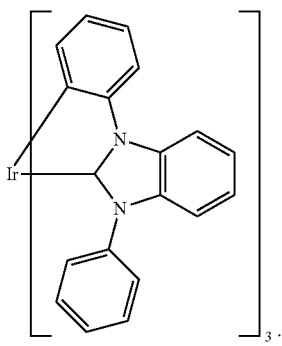

Another example of a suitable carbene complex is Ir(DPABIC)$_3$

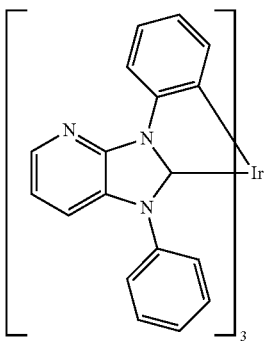

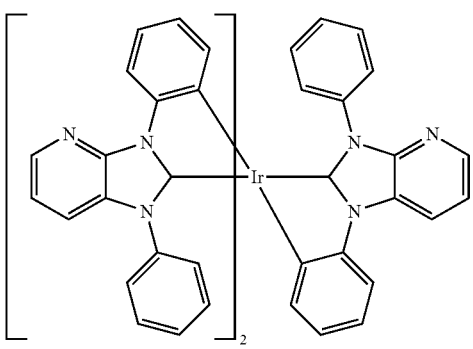

Another example of a suitable carbene complex is

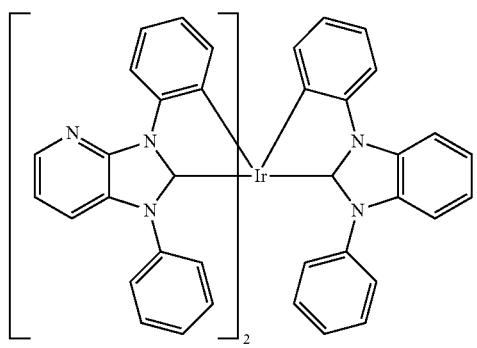

Ir(DPABIC)$_2$(DPBIC)

Anode (a)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

The anode materials mentioned above are commercially available and/or prepared by processes known by a person skilled in the art.

Cathode (b)

The cathode (b) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

The cathode materials mentioned above are commercially available and/or prepared by processes known by a person skilled in the art.

Further Layers in the Inventive OLED
Blocking Layer for Holes/Excitons (f)

Among the materials mentioned below as electron transport materials, some may fulfil several functions. For example, some of the electron transport materials are simultaneously hole-blocking materials when they have a low-lying HOMO or exciton-blocking materials when they have a sufficiently high triplet energy. These can be used, for example, in the blocking layer for holes/excitons (f). However, it is likewise possible that the function as a hole/exciton blocker is also adopted by the layer (g), such that the layer (f) can be dispensed with.

Electron Transport Layer (g)

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxyquinolato)aluminum ($Alq_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

The electron-transport materials mentioned above are commercially available and/or prepared by processes known by a person skilled in the art.

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIa) below. More preferably, in mixed electron-transporting layers, in addition to at least one phenanthroline compound, alkaline earth metal or alkali metal hydroxyquinolate complexes, for example Liq (8-hydroxyquinolatolithium), are used. Suitable alkaline earth metal or alkali metal hydroxyquinolate complexes are specified below (formula VII). Reference is made to WO2011/157779.

The electron transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the above-mentioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP 1786050, or with compounds as described in EP1 837 926 B1.

In a preferred embodiment, the electron transport layer comprises at least one compound of the general formula (VII)

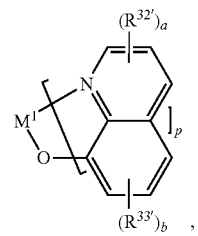

in which $R^{32'}$ and $R^{33'}$ are each independently F, $C_1$-$C_8$-alkyl, or $C_6$-$C_{14}$-aryl, which is optionally substituted by one or more $C_1$-$C_8$-alkyl groups, or two $R^{32'}$ and/or $R^{33'}$ substituents together form a fused benzene ring which is optionally substituted by one or more $C_1$-$C_8$-alkyl groups;

a and b are each independently 0, 1, 2 or 3, $M^1$ is an alkaline metal atom or alkaline earth metal atom, p is 1 when $M^1$ is an alkali metal atom, p is 2 when $M^1$ is an alkali metal atom.

A very particularly preferred compound of the formula (VII) is

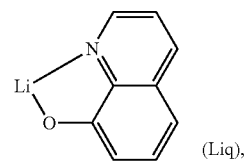

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transporting layer comprises at least one compound of the formula (VIII),

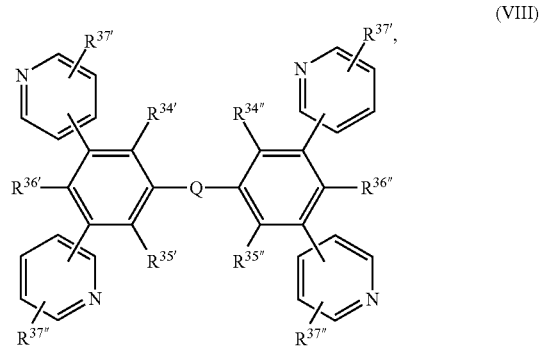

in which $R^{34'}$, $R^{35'}$, $R^{36'}$, $R^{37'}$, $R^{34''}$, $R^{35''}$, $R^{36''}$ and $R^{37''}$ are each independently hydrogen, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;

D is —CO—; —COO—; —S—; —SO—; —SO$_2$—; —O—; —NR$^{40'}$—; —SiR$^{45'}$R$^{46'}$—, —POR$^{47'}$—; —CR$^{38'}$=CR$^{39'}$—; or —C≡C—;

E is —OR$^{44'}$; —SR$^{44'}$; —NR$^{40'}$R$^{41'}$; —COR$^{43'}$; —COOR$^{42'}$; —CONR$^{40'}$R$^{41'}$; —CN; or F;

G is E, C$_1$-C$_{18}$-alkyl, C$_1$-C$_{18}$-alkyl which is interrupted by D C$_1$-C$_{18}$-perfluoroalkyl, C$_1$-C$_{18}$-alkoxy, or C$_1$-C$_{18}$-alkoxy which is substituted by E and/or interrupted by D, in which R$^{38'}$ and R$^{39'}$ are each independently H, C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—;

R$^{40'}$ and R$^{41'}$ are each independently C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—; or R$^{40'}$ and R$^{41'}$ together form a 6-membered ring;

R$^{42'}$ and R$^{43'}$ are each independently C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—, R$^{44'}$ is C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—, R$^{45'}$ and R$^{46'}$ are each independently C$_1$-C$_{18}$-alkyl, C$_6$-C$_{18}$-aryl or C$_6$-C$_{18}$-aryl which is substituted by C$_1$-C$_{18}$-alkyl, R$^{47'}$ is C$_1$-C$_{18}$-alkyl, C$_6$-C$_{18}$-aryl or C$_6$-C$_{18}$-aryl which is substituted by C$_1$-C$_{18}$-alkyl.

Preferred compounds of the formula (VIII) are compounds of the formula (VIIIa)

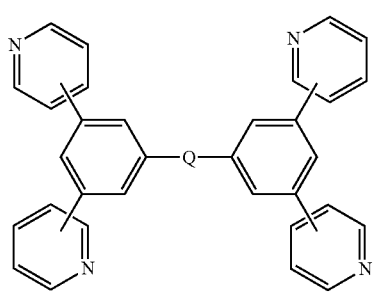

(VIIIa)

in which Q is:

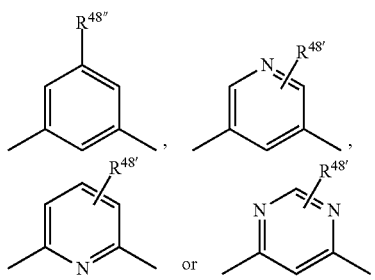

R$^{48'}$ is H or C$_1$-C$_{18}$-alkyl and R$^{48''}$ is H, C$_1$-C$_{18}$-alkyl or

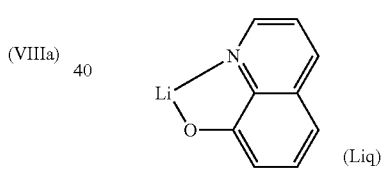

Particular preference is given to a compound of the formula

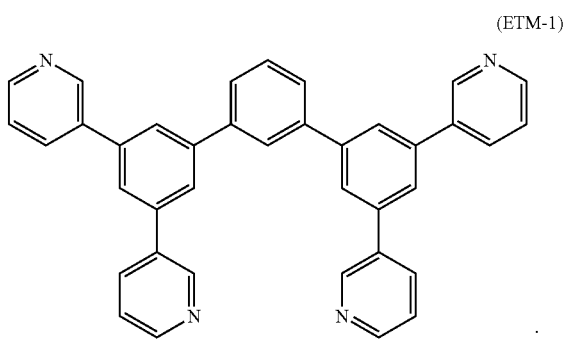

(ETM-1)

In a further, very particularly preferred embodiment, the electron transport layer comprises a compound of the formula

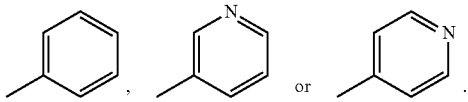

(Liq)

and a compound ETM-1.

In a preferred embodiment, the electron transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

It is likewise possible to use mixtures of alkali metal hydroxyquinolate complexes, preferably Liq, and dibenzofuran compounds in the electron transport layer. Reference is made to WO2011/157790. Dibenzofuran compounds A-1 to A-36 and B-1 to B-22 described in WO 2011/157790 are preferred, wherein dibenzofuran compound

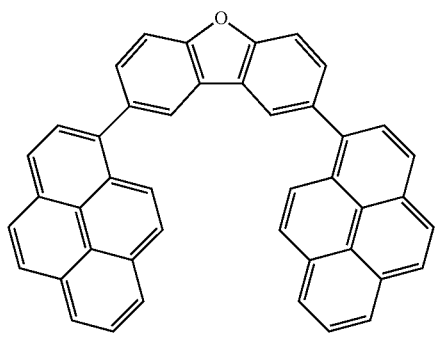 [SMILES: c1cc2ccc3ccc(-c4ccc5oc6ccc(-c7ccc8ccc9cccc%10ccc7c8c9%10)cc6c5c4)c4ccc(c1)c2c34]

(A-10; =ETM-2) is most preferred.

In a preferred embodiment, the electron transport layer comprises Liq in an amount of 99 to 1% by weight, preferably 75 to 25% by weight, more preferably about 50% by weight, where the amount of Liq and the amount of the dibenzofuran compound(s), especially ETM-2, adds up to a total of 100% by weight.

In a preferred embodiment, the electron transport layer comprises at least one phenanthroline derivative and/or pyridine derivative.

In a further preferred embodiment, the electron transport layer comprises at least one phenanthroline derivative and/or pyridine derivative and at least one alkali metal hydroxyquinolate complex.

In a further preferred embodiment, the electron transport layer comprises at least one of the dibenzofuran compounds A-1 to A-36 and B-1 to B-22 described in WO2011/157790, especially ETM-2.

In a further preferred embodiment, the electron transport layer comprises a compound described in WO 2012/111462, WO 2012/147397 and US 2012/0261654, such as, for example, a compound of formula (ETM-4)

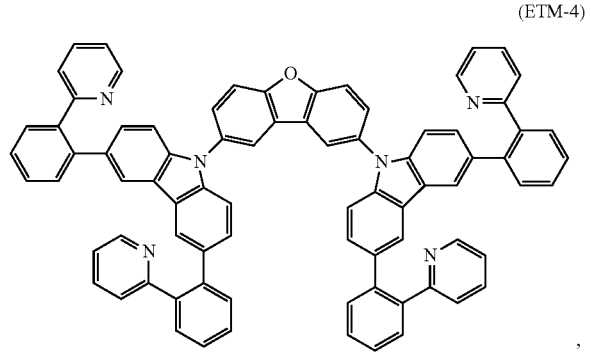 [SMILES: c1ccc(-c2ccccc2-c2ccc3c(c2)c2cc(-c4ccccc4-c4ccccn4)ccc2n3-c2ccc3oc4ccc(-n5c6ccc(-c7ccccc7-c7ccccn7)cc6c6cc(-c7ccccc7-c7ccccn7)ccc65)cc4c3c2)nc1]

WO 2012/115034, such as for example, such as, for example, a compound of formula (ETM-5)

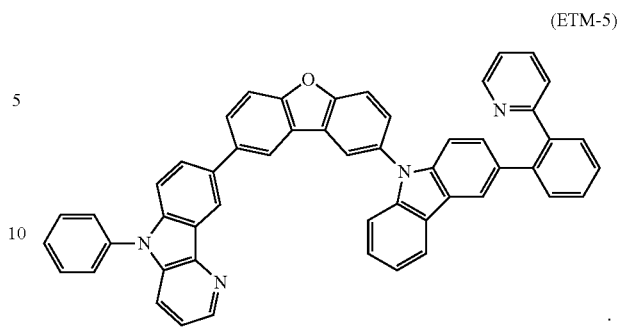

Hole Injection Layer (h)

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics, e.g. Plxecore AJ20-1000), and copolymers such as poly(3,4-ethylenedioxythiophene)/poly(4-styrenesulfonate) also called PEDOT/PSS.

The hole injection materials mentioned above are commercially available and/or prepared by processes known by a person skilled in the art.

Electron Injection Layer (i)

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (b) as an electron injection layer (i) in order to reduce the operating voltage.

The electron injection materials mentioned above are commercially available and/or prepared by processes known by a person skilled in the art.

In general, the different layers in the inventive OLED, if present, have the following thicknesses:
anode (a): 50 to 500 nm, preferably 100 to 200 nm;
a hole injection layer (h): 5 to 100 nm, preferably 20 to 80 nm,
hole-transport layer (d): 5 to 100 nm, preferably 10 to 80 nm,
electron/exciton blocking layer (e): 1 to 50 nm, preferably 5 to 10 nm,
light-emitting layer (c): 1 to 100 nm, preferably 5 to 60 nm,
a hole/exciton blocking layer (f): 1 to 50 nm, preferably 5 to 10 nm,
electron-transport layer (g): 5 to 100 nm, preferably 20 to 80 nm,
electron injection layer (i): 1 to 50 nm, preferably 2 to 10 nm,
cathode (b): 20 to 1000 nm, preferably 30 to 500 nm.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive organic electronic device, preferably OLED, can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the organic electronic device, preferably OLED, can be applied from solutions or dispersions in suitable solvents, employing coating techniques known to those skilled in the art.

The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer has/have greater thicknesses than the layer thicknesses specified when they are electrically doped.

In a further embodiment the present invention relates to the use of a cyclometallated Ir complex of formula (I) according to the present invention in an OLED, preferably as emitter material. Suitable and preferred cyclometallated Ir complexes of formula (I) and suitable and preferred OLEDs are mentioned above. The emitter material is present in the light-emitting layer of the OLED.

Use of at least one cyclometallated Ir complex of formula (I) according to the present invention in an OLED, preferably as emitter material makes it possible to obtain OLEDs with high efficiency and/or high luminous efficacy and/or with high stability and especially long lifetimes.

The organic electronic devices, preferably OLEDs, can be used in all apparatus in which electroluminescence is useful. Suitable devices are preferably selected from the group consisting of stationary visual display units, such as visual display units of computers, televisions, visual display units in printers, kitchen appliances, advertising panels, information panels and illuminations; mobile visual display units such as visual display units in smartphones, cellphones, tablet computers, laptops, digital cameras, MP3-players, vehicles, keyboards and destination displays on buses and trains; illumination units; units in items of clothing; units in handbags, units in accessories, units in furniture and units in wallpaper.

The present invention therefore further relates to apparatus selected from the group consisting of stationary visual display units, such as visual display units of computers, televisions, visual display units in printers, kitchen appliances, advertising panels, information panels and illuminations; mobile visual display units such as visual display units in smartphones, cellphones, tablet computers, laptops, digital cameras, MP3-players, vehicles, keyboards and destination displays on buses and trains; illumination units; units in items of clothing; units in handbags, units in accessories, units in furniture and units in wallpaper, comprising at least one organic electronic device, preferably at least one OLED, according to the present invention or comprising at least one hole transport layer or at least one electron/exciton blocking layer according to the present invention or comprising at least one cyclometallated Ir complex of formula (I) according to the present invention.

In a further embodiment, the cyclometallated Ir complex of formula (I) can be used in white OLEDs.

The OLEDs may further comprise at least one second light-emitting layer. The overall emission of the OLEDs may be composed of the emission of the at least two light-emitting layers and may also comprise white light, as described for example in EP13160198.1.

In addition, the cyclometallated Ir complex of formula (I) can be used in OLEDs with inverse structure. The structure of inverse OLEDs and the materials typically used therein are known to those skilled in the art.

It is also possible to stack two OLEDs or to stack three or more OLEDs ("stacked device concept"). These devices usually use a transparent charge generating interlayer such as indium tin oxide (ITO), $V_2O_5$, or an organic p-n junction.

The stacked OLED (SOLED) usually includes at least two individual sub-elements.

Each sub-element comprises at least three layers: an electron transport layer, an emitter layer and a hole-transport layer. Additional layers may be added to a sub-element. Each SOLED sub-element may include for example a hole injection layer, a hole transport layer, an electron/exciton blocking layer, an emitter layer, a hole/exciton blocking layer, an electron transport layer, an electron injection layer. Each SOLED sub-element may have the same layer structure or different layer structure from the other sub-elements.

Suitable SOLED structures are known by a person skilled in the art.

Not only the organic electronic devices as mentioned above are a subject of the present invention but also all cyclometallated Ir complexes of formula (I) as described in the present application.

In a further embodiment, the present invention relates to a cyclometallated Ir of formula (I) as described in the present application, and to a process for preparing the inventive metal-carbene complex, by contacting suitable compounds comprising Ir with appropriate ligands or ligand precursors. A suitable process is described above.

The present invention further relates to the use of the inventive cyclometallated Ir complex of formula (I) as described in the present application in organic electronic devices, preferably in OLEDs, more preferably as emitter materials in OLEDs. Suitable organic electronic devices and suitable OLEDs are described above.

The following examples are included for illustrative purposes only and do not limit the scope of the claims.

EXAMPLES

The examples which follow, more particularly the methods, materials, conditions, process parameters, apparatus and the like detailed in the examples, are intended to support the present invention, but not to restrict the scope of the present invention.

All experiments are carried out in protective gas atmosphere.

The percentages and ratios mentioned in the examples below—unless stated otherwise—are % by weight and weight ratios.

A Synthesis of the Inventive Ir Complexes

1 Synthesis of

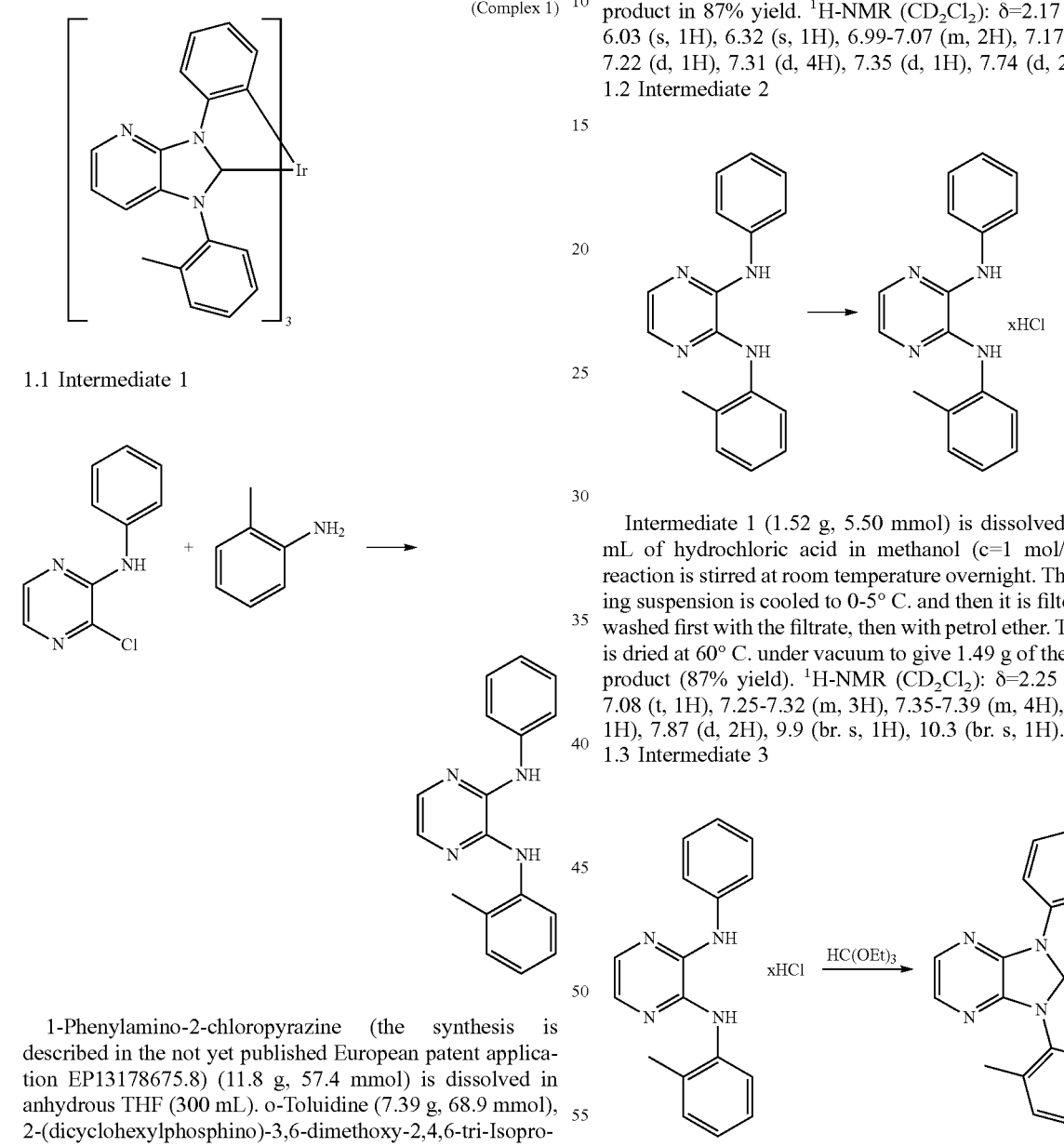

(Complex 1)

1.1 Intermediate 1

1-Phenylamino-2-chloropyrazine (the synthesis is described in the not yet published European patent application EP13178675.8) (11.8 g, 57.4 mmol) is dissolved in anhydrous THF (300 mL). o-Toluidine (7.39 g, 68.9 mmol), 2-(dicyclohexylphosphino)-3,6-dimethoxy-2,4,6-tri-Isopropyl-1,1-biphenyl (BrettPhos) (0.31 g, 0.57 mmol) and chloro[2-(dicyclohexylphosphino)3,6-dimethoxy-2',4',6'-tri-i-propyl-1,1'-biphenyl][2-(2-aminoethyl)phenyl]palladium(II) (0.47 g, 0.57 mmol) are added. To the solution cesium carbonate (22.7 g, 68.9 mmol) is added. The suspension is stirred at 80° C. for 24 h. After cooling to room temperature, the suspension is filtered. The filtrate is reduced under vacuum and the residue is dissolved in 200 mL of hot acetonitrile. The hot solution is cooled to 20° C. and 200 mL of n-pentane is added. Then the mixture is cooled to −15° C. After 5 minutes stirring at this temperature the precipitate is filtered off and washed with cold n-pentane. The solid is dried at 30° C. under vacuum to give 11.0 g of the desired product. The acetonitrile/n-pentane filtrate is evaporated and the residue is dissolved in 100 mL of hot acetonitrile. The hot solution is cooled to 20° C. and 100 mL of n-pentane are added. Then the mixture is cooled to −15° C. After 5 minutes stirring at this temperature the precipitate is filtered off and washed with cold n-pentane to give 2.80 g of the desired product. The collected solids give 13.8 g of the desired product in 87% yield. $^1$H-NMR (CD$_2$Cl$_2$): δ=2.17 (s, 3H), 6.03 (s, 1H), 6.32 (s, 1H), 6.99-7.07 (m, 2H), 7.17 (t, 1H), 7.22 (d, 1H), 7.31 (d, 4H), 7.35 (d, 1H), 7.74 (d, 2H).

1.2 Intermediate 2

Intermediate 1 (1.52 g, 5.50 mmol) is dissolved in 27.5 mL of hydrochloric acid in methanol (c=1 mol/L). The reaction is stirred at room temperature overnight. The resulting suspension is cooled to 0-5° C. and then it is filtered and washed first with the filtrate, then with petrol ether. The solid is dried at 60° C. under vacuum to give 1.49 g of the desired product (87% yield). $^1$H-NMR (CD$_2$Cl$_2$): δ=2.25 (s, 3H), 7.08 (t, 1H), 7.25-7.32 (m, 3H), 7.35-7.39 (m, 4H), 7.52 (s, 1H), 7.87 (d, 2H), 9.9 (br. s, 1H), 10.3 (br. s, 1H).

1.3 Intermediate 3

Intermediate 2 (1.33 g, 4.26 mol) and molecular sieves (5 Å and 3 Å, 3 g each) are added in a flask. Then 28 mL of trimethylorthoformate are added. The mixture is purged with argon and then heated to reflux for 1.5 h. After cooling to room temperature, the mixture is evaporated under vacuum. Then the residue is dissolved in dichloromethane and evaporated again (3×). The residue is directly used in the next step. $^1$H-NMR (CD$_2$Cl$_2$): δ=2.27 (s, 3H), 3.20 (s, 3H), 7.13 (s, 1H), 7.18 (t, 1H), 7.30-7.40 (m, 5H), 7.41-7.47 (m, 3H), 8.03 (d, 2H).

1.4 Complex 1 (fac und mer)

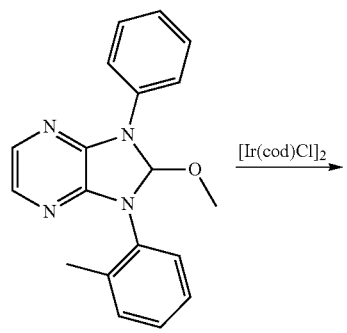

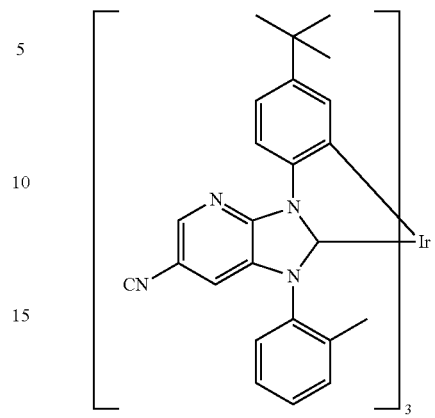

(Complex 2; mer Complex)

2.1 Intermediate 1

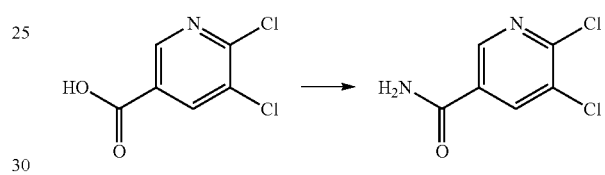

5,6-dichloropyridine-3-carboxylic acid (33 g, 0.17 mol) is dissolved in 310 mL of THF. To this solution thionyl chloride (26.2 mL, 0.22 mol) is added. Then 0.17 mL of DMF is added. The reaction mixture is stirred for 2.5 h at 50° C. After cooling to room temperature, the reaction mixture is poured into 390 mL of a concentrated ammonia solution (25%) and 500 mL of water. The mixture is cooled to 0° C. and stirred overnight to room temperature. The THF is reduced under vacuum, the aqueous solution is extracted with ethyl acetate. The organic layer is washed with water, followed by a sodium hydroxide solution (10%). After drying over anhydrous sodium sulfate the solvent is reduced. The residue is dried under vacuum to give 30.9 g of the desired product in 95% yield. $^1$H-NMR (DMSO): δ=7.83 (s, 1H), 8.28 (s, 1H), 8.49 (s, 1H), 8.81 (s, 1H).

2.2 Intermediate 2

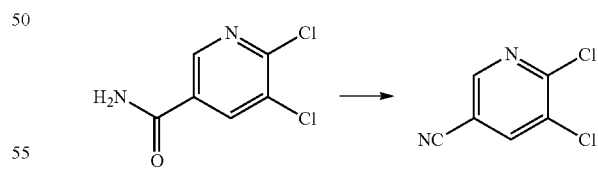

Intermediate 3 (1.36 g, 4.26 mmol) is dissolved in 40 mL of anhydrous o-xylene under argon. Then di-μ-chloro-bis[(cycloocta-1,5-dien)iridium(I)] (0.29 g, 0.43 mmol) is added to the solution. After degassing the solution with argon flux, the reaction is heated up to 140° C. overnight. The solvent of the reaction mixture is removed and the residue is purified by column chromatography (silica). One fraction yields 140 mg of the fac isomer (15%). The solid obtained from another fraction is stirred in a solution of acetone/acetonitrile and precipitated by addition of acetone to yield 295 mg of the mer isomer (33%).

fac isomer $^1$H-NMR (CD$_2$Cl$_2$): δ=0.68 (s, 9H), 6.49-6.55 (m, 6H), 6.66 (t, 3H), 6.77 (t, 3H), 6.87 (d, 3H), 7.05 (t, 3H), 7.84 (d, 3H), 8.07 (d, 3H), 8.24 (d, 3H), 8.44 (d, 3H).

Photoluminescence (2% film in PMMA): $\lambda_{max}$=475 nm; $\tau_0$=3.0 μs; PLQY=93%.

mer isomer MALDI-MS: m/z=1047.228.

Photoluminescence (2% film in PMMA): $\lambda_{max}$=521 nm; $\tau_0$=1.2 μs; PLQY=75%.

2 Synthesis of

Intermediate 1 (8.4 g, 44 mmol) is suspended in 76 mL of thionyl chloride. The reaction mixture is stirred under reflux for 72 h. The solvent is reduced under vacuum and the residue is dissolved in chloroform. The organic layer is washed with water and dried over anhydrous sodium sulfate. After reducing the solvent under vacuum, the solid is first purified via column chromatography (reversed phase, eluent: acetonitrile/dichloromethane) and then crystallized in ethyl acetate to give the title product in 78% yield (5.95 g). $^1$H-NMR (CDCl$_3$): δ=8.05 (s, 1H), 8.60 (s, 1H).

2.3 Intermediate 3

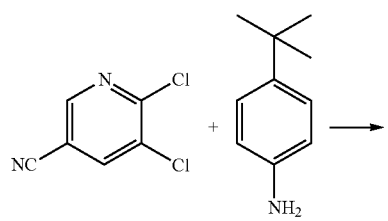

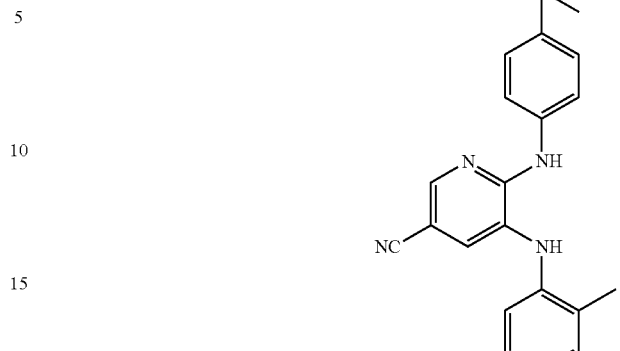

Intermediate 2 (10.0 g, 58 mmol), 4-tert-butylphenylamine (9.5 g, 64 mmol) and 30 mL of diisopropylethylamine are suspended in 200 mL of dimethylacetamide under argon atmosphere. The suspension is heated to 120° C. and stirred overnight. After cooling to room temperature, the remaining liquid is removed and the residue is taken up in methylene chloride. The organic phase is sequentially washed with hydrochloric acid (5%), a saturated sodium hydrogen carbonate solution and finally with water. The organic layer is dried over anhydrous sodium sulfate. The remaining solution is filtered over silica, then the solvent is removed and the solid dried at 40° C. under vacuum. The yellow product is crystallized in ethyl acetate to give the title product as a white powder (15.5 g) in 93% yield. $^1$H-NMR (400 MHz, CDCl$_3$): δ=1.33 (s, 9H), 7.28 (br. s, 1H), 7.41 (d, 2H), 7.50 (d, 2H), 7.75 (d, 1H), 8.38 (d, 1H).

2.4 Intermediate 4

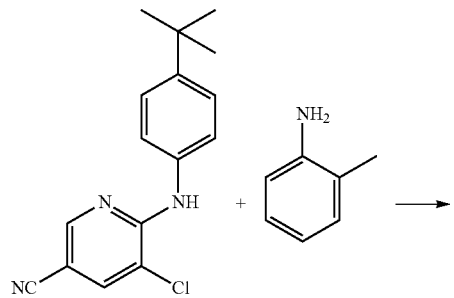

Intermediate 3 (13.2 g, 46.2 mmol) is suspended in 150 mL of THF. Then 8.94 g (64.7 mmol) potassium carbonate, 248 mg (1.16 mmol) 2-(dicyclohexylphosphino)-3,6-dimethoxy-2,4,6-tri-Isopropyl-1,1-biphenyl, 369 mg (1.16 mmol) chloro-[2-(dicyclohexylphosphino)-3,6-dimethoxy-2,4,6-tri-Isopropyl-1,1-biphenyl]-[2-(2-aminoethyl)phenyl]palladium(II) and 4.95 g (46.2 mmol) o-toluidine are added under argon atmosphere. The mixture is stirred for 48 h at 66° C. After cooling to room temperature, the reaction is diluted with 500 mL of methylene chloride. The organic phase is washed with water, then dried over anhydrous sodium sulfate and the solvents are removed. The residue is dissolved in methylene chloride and filtered over silica. After removing the solvent the brown oil is purified via column chromatography (silica, cyclohexane/ethyl acetate) and the desired product is obtained in 46% yield (7.52 g).

$^1$H-NMR (400 MHz, CDCl$_3$): δ=1.31 (s, 9H), 2.27 (s, 3H), 5.00 (s, 1H), 6.67 (d, 1H), 6.98 (t, 1H), 7.14 (t, 1H), 7.23 (d, 2H), 7.31 (s, 1H), 7.36 (d, 2H), 7.43 (d, 2H), 8.29 (d, 1H).

2.5 Intermediate 5

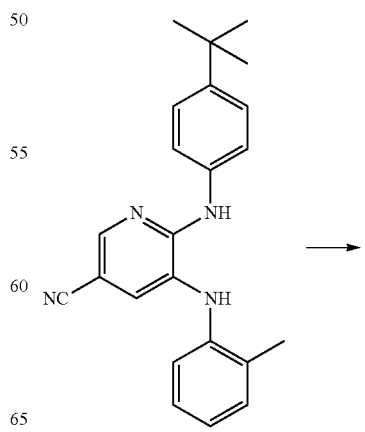

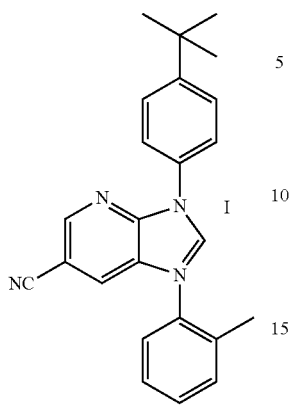

Intermediate 4 (3.15 g, 8.84 mmol) is dissolved in 107 mL of acetonitrile under argon atmosphere. The mixture is degassed with argon for 5 minutes and then cooled to 0° C. (Chlormethylene)dimethylammonium chloride (3.4 g, 26.5 mmol) is added. The mixture is stirred at 0-15° C. for 24 h. Then 3.98 g (26.5 mmol) sodium iodide is added at 0° C. to the reaction. The mixture is stirred at 0-12° C. overnight. The suspension is filtered and the residue is washed with cold acetonitrile. The filtrate is evaporated and dissolved in acetonitrile. This solution is washed with petrol ether. The acetonitrile phase is evaporated again to give an oily residue. The oil is mixed with a mixture of methyl tert-butyl ether and methylene chloride (3:1). A yellow precipitate is falling out. The suspension is stirred overnight, then filtered and washed with a mixture of methyl tert-butyl ether and methylene chloride (3:2). The residue is dried at 40° C. under vacuum to give 5.69 g of the desired product. $^1$H-NMR (400 MHz, CD$_2$Cl$_2$): δ=1.42 (s, 9H), 2.33 (s, 3H), 7.54-7.59 (m, 2H), 7.68 (t, 1H), 7.75 (d, 2H), 8.13 (d, 1H), 8.20 (t, 3H), 8.40 (s, 1H), 9.09 (s, 1H), 10.91 (s, 1H).

2.6 Intermediate 6

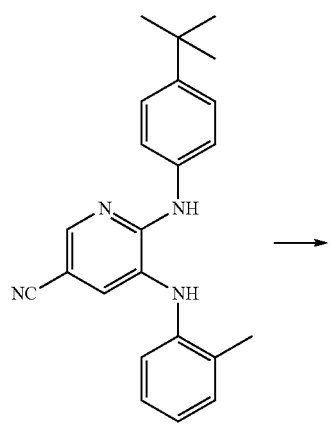

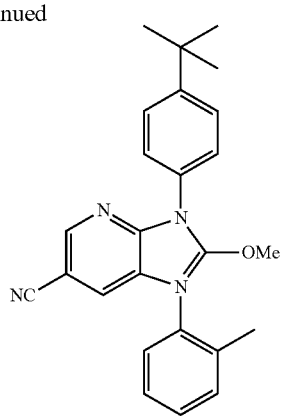

Intermediate 5 (2.8 g, 6.0 mmol) is dissolved in 60 mL of methanol under argon atmosphere. The mixture is cooled to 0° C. Sodium methanolate (325 mg, 6.0 mmol) is added to the solution. The mixture is stirred at 0° C. up to room temperature overnight. The resulting suspension is filtered and washed with cold methanol. The residue is dried at 40° C. under vacuum. The desired product is obtained as a solid in 55% yield (1.04 g). $^1$H-NMR (400 MHz, CD$_2$Cl$_2$): δ=1.35 (s, 9H), 2.25 (s, 3H), 3.19 (s, 3H), 6.42 (s, 1H), 7.08 (s, 1H), 7.33-7.41 (m, 4H), 7.48 (d, 2H), 7.84 (d, 2H), 7.93 (d, 1H).

2.7 Complex 2 (mer complex)

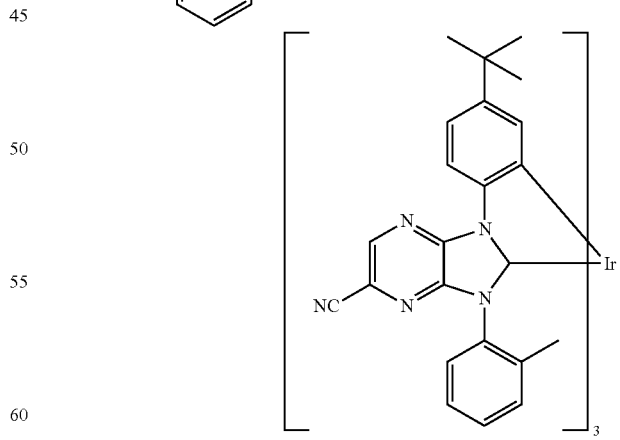

Intermediate 6 (0.97 g, 2.43 mmol) is added to a mixture of 58 mL of o-xylene and 163 mg (0.243 mmol) di-μ-chloro-bis[(cycloocta-1,5-dien)iridium(I)]. After degassing the mixture with argon for 5 minutes, the reaction is heated up to 140° C. overnight. After cooling to room temperature, the reaction mixture is filtered and the residue is washed with o-xylene. The filtrate is evaporated under vacuum and the obtained residue is purified via column chromatography (silica, cyclohexane/ethyl acetate) to give 863 mg of the desired product. The solid is stirred in a solution of acetone/acetonitrile (1:1; 8 mL) overnight, filtered and washed with clean acetone/acetonitrile mixture (1:1) to give 495 mg of the desired product (79%). MALDI-MS: m/z =1289.501.

Photoluminescence (2% film in PMMA): $\lambda_{max}$=512 nm; $\tau_0$=0.9 µs; PLQY=80%.

3 Synthesis of

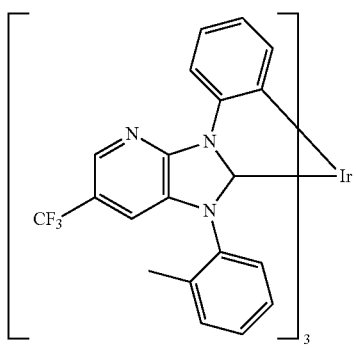

(Complex 3; mer Complex)

3.1 Intermediate 1

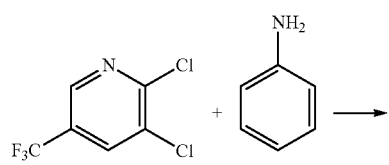

40.0 g (0.19 mol) 5-(trifluoromethyl)-2,3-dichloropyridine, 19.0 g (0.20 mol) aniline and 91.8 g (0.71 mol) diisopropylethylamine are dissolved in 200 mL of DMA. The mixture is purged with argon for 10 minutes and then heated to 110° C. overnight. The orange solution is evaporated under vacuum and the residue is dried in vacuum at 80° C. for 1.5 h. The residue is heated in 250 mL of toluene and activated char coal. After filtration and evaporating the solvent, the residue is dissolved again in toluene and filtered over silica. The filtrate is again evaporated under vacuum, then dissolved in dichloromethane and filtered. The yellow solution is concentrated and dried to give 13.1 g of the desired product in 26% yield. $^1$H-NMR (400 MHz, CD$_2$Cl$_2$): δ=7.13 (t, 1H), 7.29 (br. s, 1H), 7.36 (t, 2H), 7.64 (d, 2H), 7.80 (d, 1H), 8.36 (d, 1H).

3.2 Intermediate 2

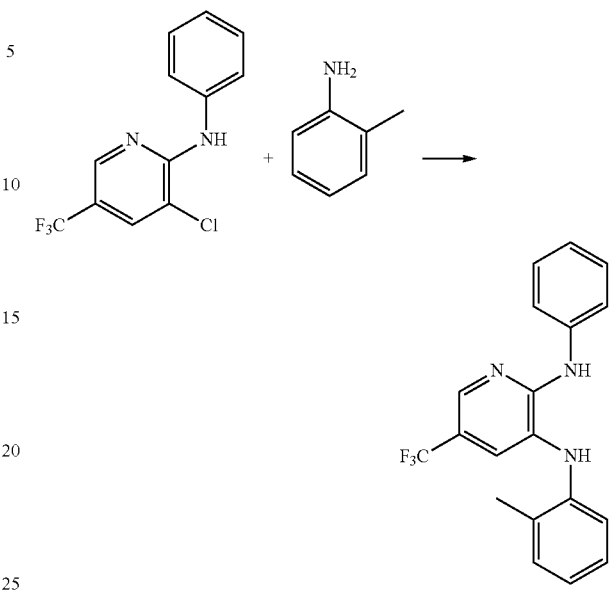

8.80 g (63.7 mmol) potassium carbonate, 5.45 g (50.9 mmol) o-toluidine, 0.61 g (1.14 mmol) 2-(dicyclohexylphosphino)-3,6-dimethoxy-2,4,6-triisopropyl-1,1-biphenyl and 0.91 g (1.14 mmol) chloro[2-(dicyclohexylphosphino)-3,6-dimethoxy-2',4',6'-tri-i-propyl-1,1'-biphenyl][2-(2-aminoethyl)phenyl]palladium(II) are added to a solution of intermediate 1 (13.0 g, 47.7 mmol) in 500 mL of THF. The reaction mixture is degassed with argon and then heated to reflux overnight. After cooling to room temperature, the suspension is filtered and washed with dichloromethane. The filtrate is concentrated. The residue is dissolved in toluene and filtered over 7 cm silica column to give 13.7 g of the product in 83% yield. $^1$H-NMR (400 MHz, CD$_2$Cl$_2$): δ=2.29 (s, 3H), 5.10 (s, 1H), 6.64-6.69 (m, 1H), 6.91-7.42 (m, 8H), 7.54-7.59 (m, 2H), 8.29 (s, 1H).

3.3 Intermediate 3

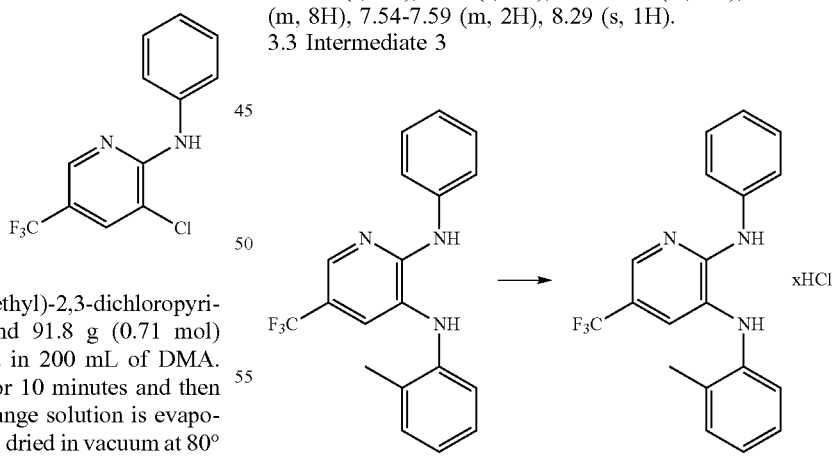

Intermediate 2 (13.7 g, 39.8 mmol) is suspended in 50 mL of toluene. To this mixture 20 mL of hydrochloric acid (32%) are added. After 10 minutes the suspension is diluted with 50 mL of toluene and the reaction is stirred overnight at room temperature. The suspension is filtered and washed with toluene. The residue is dried at 50° C. under vacuum to give 12.4 g of the desired product in 82% yield. $^1$H-NMR (400 MHz, DMSO): δ=2.19 (s, 3H), 6.81 (s, 1H), 6.99-7.09

(m, 3H), 7.21 (t, 1H), 7.29 (d, 1H), 7.35 (t, 2H), 7.75 (d, 2H), 8.00 (s, 1H), 9.02 (br. s, 1H).

3.4 Intermediate 4

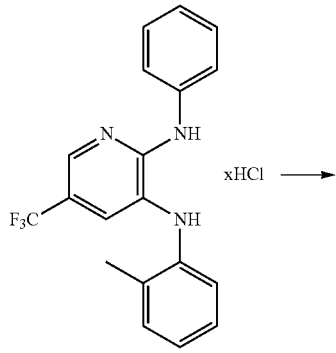

xHCl ⟶

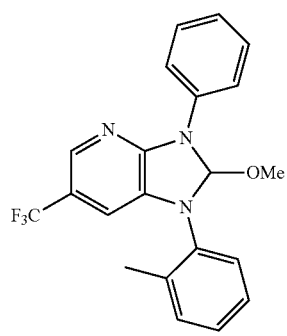

Intermediate 3 (12.0 g, 31.6 mmol) is suspended in 120 mL of trimethylorthoformate. The suspension is degassed with argon and then heated to 120° C. overnight. The orange solution is concentrated under vacuum to give 12.2 g of a brown oil which is used without further purification. $^1$H-NMR (400 MHz, DMSO): δ=2.26 (s, 3H), 3.10 (s, 3H), 6.40 (s, 1H), 7.22 (t, 1H), 7.35-7.61 (m, 7H), 7.93 (s, 1H), 8.04 (d, 2H).

3.5 Complex 3 (mer Complex)

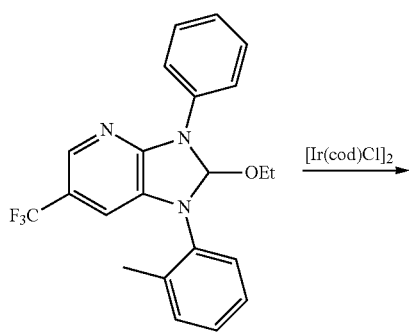

[Ir(cod)Cl]$_2$ ⟶

-continued

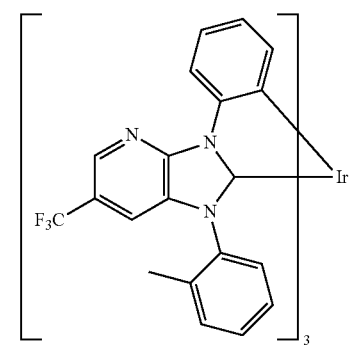

Intermediate 4 (2.48 g, 6.44 mmol) is dissolved in 60 ml xylene. Molecular sieve (3 Å, 2.5 g) and then di-μ-chloro-bis[cycloocta-1,5-dien)iridium(I)] (432 mg, 0.643 mmol) are added to the solution. After degassing the solution with argon for 30 minutes, the reaction is stirred overnight at 120° C. After cooling to room temperature, the solid residues are removed by filtration and washed with dichloromethane. The solvent is removed and the residue is dissolved in toluene. The solution is stirred overnight. The precipitate is filtered off and the filtrate is concentrated under vacuum. The residue is purified via column chromatography (silica, cyclohexane/ethyl acetate). The resulting product is stirred in MTBE overnight, then filtered and dried. The product is obtained as a yellow solid in 49% yield (780 mg).

Photoluminescence (2% film in PMMA): λ$_{max}$=488 nm; τ$_0$=0.9 μs; PLQY=91%.

4 Synthesis of

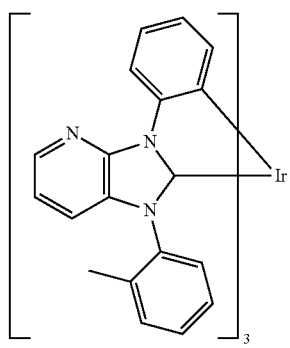

(Complex 4, mer Complex)

4.1 Intermediate 1

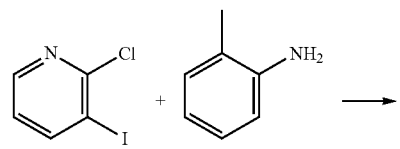

+ ⟶

-continued

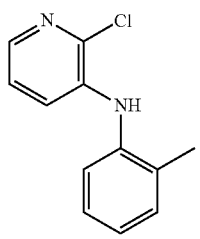

2-Chloro-3-iodopyridine (4.22 g, 17.6 mmol) is dissolved in toluene (50 mL) and degassed under argon flux. Then palladium(II)acetate (117 mg, 0.52 mmol), (R)-BINAP (333 mg, 0.53 mmol), cesium carbonate (5.38 g, 16.5 mmol) and o-toluidine (1.90 g, 17.7 mmol) are added. The mixture is heated to reflux and stirred for 72 h. After cooling to room temperature, the reaction mixture is filtered and the filtrate is concentrated under vacuum. The residue is purified by column chromatography (silica, eluent: toluene). The product is obtained in 73% yield (2.81 g). $^1$H-NMR (400 MHz, $CD_2Cl_2$): δ=2.24 (s, 3H), 5.94 (s, 1H), 7.05 (d, 2H), 7.12 (m, 1H), 7.22 (d, 2H), 7.29 (d, 1H), 7.78 (t, 1H).

4.2 Intermediate 2

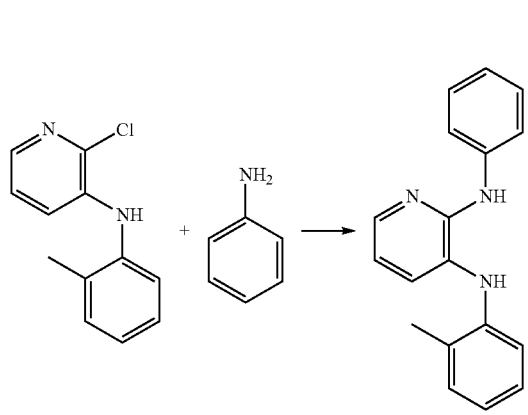

Intermediate 1 (1.80 g, 8.23 mmol) is dissolved in toluene (42 mL) and degassed with an argon flux. Then tris(dibenzylideneacetone)dipalladium(0) (113 mg, 0.12 mmol), (R)-BINAP (234 mg, 0.38 mmol), sodium tert-butoxide (1.15 g, 12.0 mmol) and aniline (0.92 g, 9.88 mmol) are added. The suspension is heated to reflux and stirred for 3 d. After cooling to room temperature, the reaction mixture is filtered and the residue is washed with dichloromethane. The filtrate is concentrated under vacuum. Then the residue is dissolved in dichloromethane and silica is added to the solution, till the color of the overlaying solvent is orange. The mixture is filtered with dichloromethane over a layer of silica and the product is obtained in 92% yield (2.08 g). $^1$H-NMR (400 MHz, $CD_2Cl_2$): δ=2.29 (s, 3H), 5.07 (s, 1H), 6.61 (d, 1H), 6.78 (q, 1H), 6.85 (t, 1H), 6.91 (s, 1H), 6.96 (t, 1H), 7.05 (t, 1H), 7.19 (d, 1H), 7.27 (t, 3H), 7.53 (d, 2H), 8.05 (d, 1H).

4.3 Intermediate 3

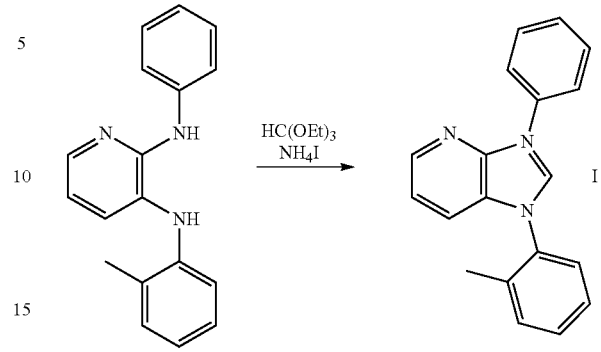

Intermediate 2 (1.41 g, 5.12 mmol) and ammonium iodide (0.78 g, 5.38 mmol) are suspended in triethylorthoformate (8.5 mL) under argon. The mixture is heated to 80° C. and stirred for 3 d. The formed suspension is filtered and the product is obtained in 52% yield (1.11 g). $^1$H-NMR (400 MHz, $CD_2Cl_2$): δ=2.31 (s, 3H), 7.58 (m, 2H), 7.71 (m, 5H), 7.89 (d, 1H), 7.96 (d, 1H), 8.32 (d, 2H), 8.89 (d, 1H), 11.15 (s, 1H).

4.4 Complex 4 (mer Complex)

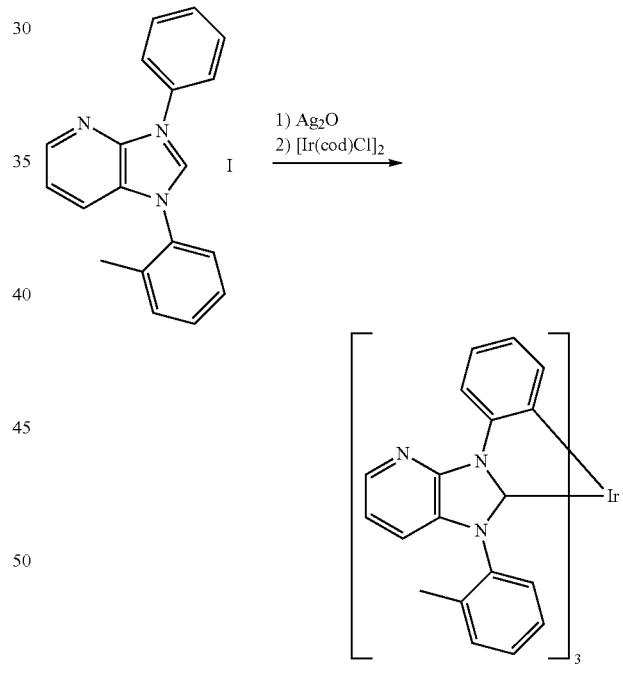

Intermediate 3 (300 mg, 0.93 mmol) and molecular sieve 3 Å (4 g) are suspended in anhydrous 1,4-dioxane (20 mL). The suspension is degassed with argon flux and then silver oxide (163 mg, 0.70 mmol) is added. The reaction is stirred in the dark at room temperature for 20 h. Then a degassed solution of di-μ-chloro-bis[(cycloocta-1,5-dien)iridium(I)] (63 mg, 0.09 mmol) in anhydrous o-xylene (20 mL) is added to the suspension. The mixture is heated to 150° C. and the 1,4-dioxane is distilled off. The resulting suspension is stirred at reflux over the weekend. The reaction mixture is filtered over a thin layer of silica and the residue is washed with o-xylene. The received filtrate is concentrated under vacuum and purified by column chromatography (silica, eluent: cyclohexane/ethyl acetate). The product is obtained in 26% yield (52 mg). MALDI-MS: m/z =1043,588.

Photoluminescence (2% film in PMMA): $\lambda_{max}$=453 nm; $\tau_0$=0.9 µs; PLQY=72%.

5 Synthesis of

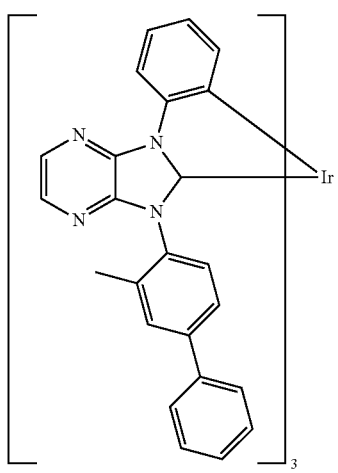

(Complex 5)

5.1 Intermediate 1

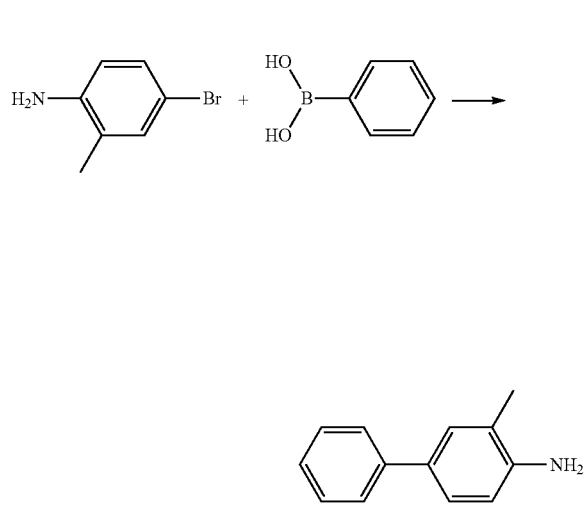

4-Bromo-2-methylaniline (20.0 g, 0.11 mol), phenylboronic acid (19.8 g, 0.16 mol) and Pd(dppf)Cl$_2$*CH$_2$Cl$_2$ (4.4 g, 5.4 mmol) are suspended in toluene (1000 mL) under argon atmosphere. Then a 3 M sodium hydroxide solution (108 mL) is added dropwise to the suspension. The mixture is heated to 90° C. and stirred overnight. After cooling to room temperature the reaction mixture is filtered over a layer of celite and the filtrate is concentrated under vacuum. The residue is dissolved in dichloromethane and extracted with water and a saturated sodium hydrogen carbonate solution. The organic layer is dried over sodium sulfate and the solvent is removed. The remaining brown oil is purified by column chromatography (silica, eluent: cyclohexane/ethyl acetate) to obtain the product in 66% yield (13.1 g). $^1$H-NMR (400 MHz, CD$_2$Cl$_2$): δ=2.21 (s, 3H), 3.70 (s, 2H), 6.72 (d, 1H), 7.25 (m, 2H), 7.31 (s, 1H), 7.37 (t, 2H), 7.53 (q, 2H).

5.2 Intermediate 2

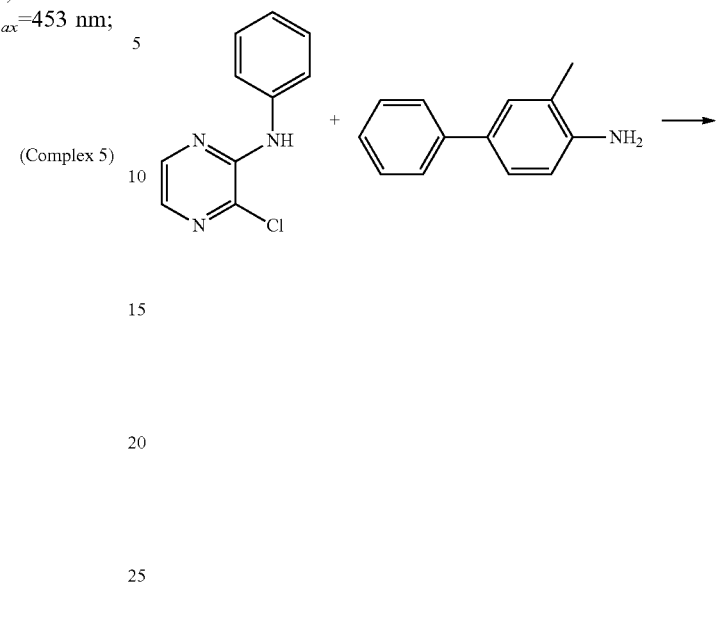

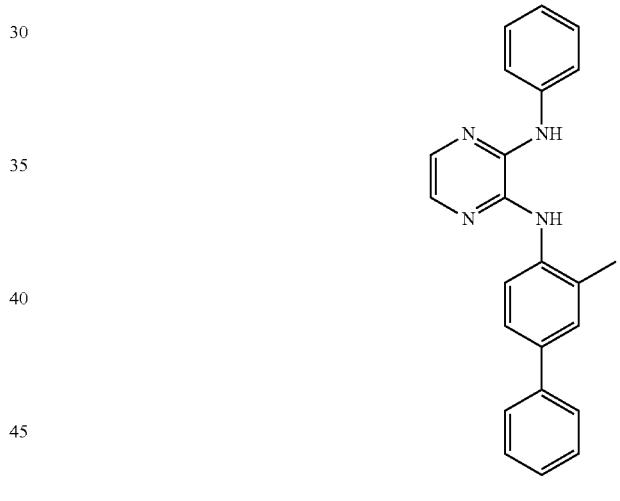

1-Phenylamino-2-chloropyrazine (14.6 g, 0.071 mol) is suspended in tetrahydrofuran (300 mL) under argon atmosphere. Then 2-(dicyclohexylphosphino)-3,6-dimethoxy-2,4,6-tri-Isopropyl-1,1-biphenyl (BrettPhos) (389 mg, 0.71 mmol) is added and stirred until it is solved. The same procedure is done with chloro[2-(dicyclohexylphosphino)-3,6-dimethoxy-2',4',6'-tri-i-propyl-1,1'-biphenyl][2-(2-aminoethyl)phenyl]palladium(II) (579 mg, 0.71 mmol). Then cesium carbonate (27.8 g, 0.085 mol) and intermediate 1 (13.0 g, 0.071 mol) are added to the solution. The suspension is heated to 78° C. and stirred for 22 h. After cooling to room temperature the mixture is filtered under vacuum and the residue washed with tetrahydrofuran. The concentrated filtrate yields 26.1 g product which is used for the next step without further purification. $^1$H-NMR (400 MHz, DMSO): δ=2.24 (s, 3H), 6.99 (t, 1H), 7.33 (q, 3H), 7.47 (m, 5H), 7.54 (d, 1H), 7.56 (s, 1H), 7.68 (d, 2H), 7.72 (d, 2H), 8.074 (s, 1H), 8.513 (s, 1H).

5.3 Intermediate 3

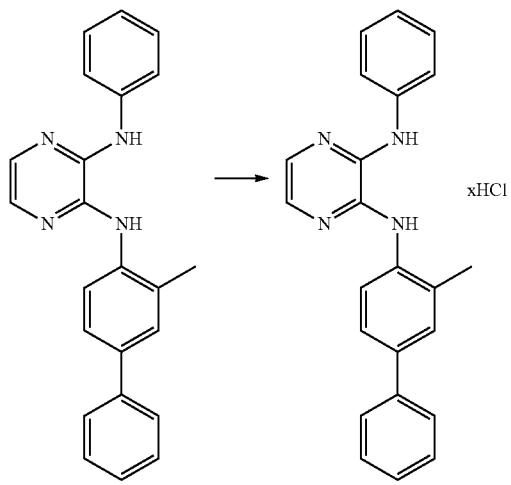 [SMILES: Cc1cc(-c2ccccc2)ccc1Nc1nccnc1Nc1ccccc1 ; Cc1cc(-c2ccccc2)ccc1Nc1nccnc1Nc1ccccc1]

Intermediate 2 (1.5 g, 4.25 mmol) is suspended in 32% hydrochloric acid (40 mL) and stirred at room temperature overnight. Then water (40 mL) is added and the mixture is stirred at room temperature for 2 d. The suspension is filtered and the solid is washed with diethyl ether and dried in vacuum. The filtrate is concentrated under vacuum, dissolved in methanol and precipitated with water. The precipitate is filtered, washed with diethyl ether and also dried in a vacuum oven. The combined residues give 1.63 g product in 98% yield. $^1$H-NMR (400 MHz, DMSO): δ=2.26 (s, 3H), 7.02 (t, 1H), 7.35 (q, 3H), 7.45 (m, 4H), 7.53 (q, 2H), 7.59 (d, 1H), 7.69 (d, 2H), 7.76 (d, 2H), 8.63 (s, 1H), 8.87 (d, 2H).

5.4 Intermediate 4

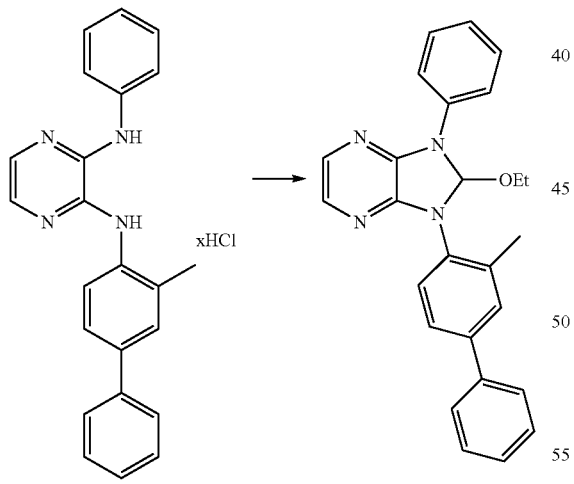

Intermediate 3 (1.97 g, 5.1 mmol) is dissolved in triethyl orthoformate (50 mL) under argon atmosphere. The mixture is heated to 100° C. and stirred for 1 h. The solution is diluted with dichloromethane and the solvent is evaporated under vacuum. The resulting solid (1.97 g) is used for the next step without further purification. $^1$H-NMR (400 MHz, CD$_2$Cl$_2$): δ=1.09 (t, 3H), 2.34 (s, 3H), 3.37-3.44 (m, 1H), 3.53-3.62 (m, 1H), 7.15 (s, 1H), 7.18 (t, 1H), 7.35-7.40 (m, 2H), 7.41-7.49 (m, 6H), 7.56 (dd, 1H), 7.61 (s, 1H), 7.64 (d, 2H), 8.05 (d, 2H).

5.5 Complex 5 (fac and mer)

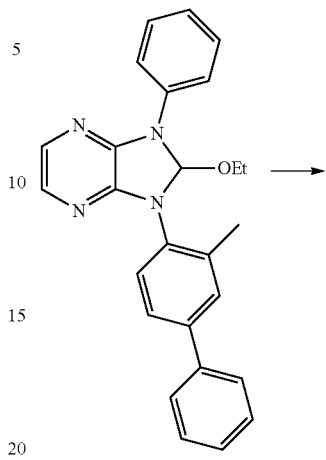

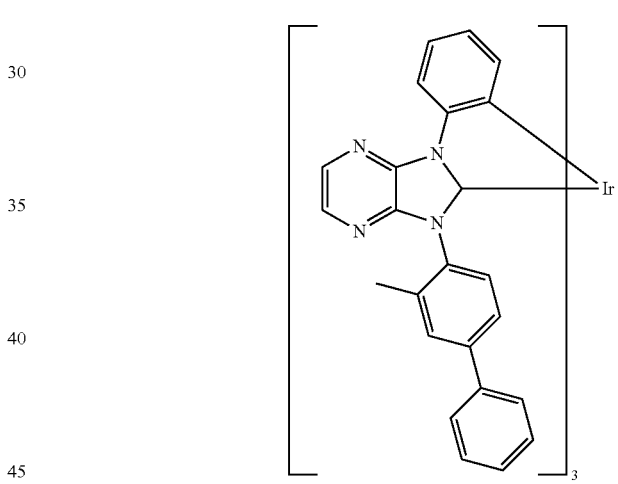

Intermediate 4 (1.97 g, 4.8 mmol) and di-μ-chloro-bis[(cycloocta-1,5-dien)iridium(I)] (324 mg, 0.48 mmol) are suspended in anhydrous o-xylene (138 mL) and the suspension is degassed under argon flux. The mixture is heated to 140° C. and stirred overnight. The suspension is cooled to room temperature and the solid is filtered off. The filtrate is concentrated and the residue is purified by column chromatography (eluent: cyclohexane/dichloromethane). The solid of one fraction is stirred in a mixture of acetone/acetonitrile 1:1 to yield 99 mg of the fac isomer (8%). Another fraction is purified further by stirring in a mixture of acetone/acetonitrile 1:1 to yield 410 mg of the mer isomer (33%).

fac isomer $^1$H-NMR (CD$_2$Cl$_2$): δ=0.77 (s, 9H), 6.48 (dd, 3H), 6.65 (dt, 3H), 7.06 (dt, 3H), 7.22-7.38 (m, 21H), 7.70 (d, 3H), 7.80 (d, 3H), 8.10 (d, 3H), 8.50 (d, 3H).

Photoluminescence (2% film in PMMA): $\lambda_{max}$=471 nm; $\tau_0$=3.7 μs; PLQY=90%.

mer isomer: Photoluminescence (2% film in PMMA): $\lambda_{max}$=521 nm; $\tau_0$=1.1 μs; PLQY=70%.

6 Synthesis of

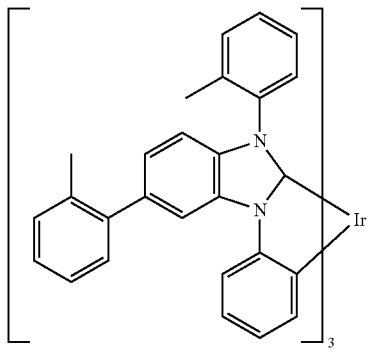

(Complex 6; mer Complex)

6.1 Intermediate 1

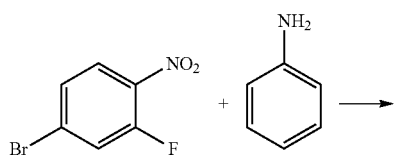

4-bromo-2-fluoronitrobenzene (1.0 g, 4.3 mmol) and aniline (490 mg, 5.2 mmol) are suspended in 1-methyl-2-pyrrolidon (2 mL). The mixture is purged with argon, then heated to 50° C. for 15 h. Additional aniline (350 mg, 3.7 mmol) is added to the reaction. The mixture is stirred at 50° C. for 15 h. After cooling to room temperature the mixture is diluted with 2 mL of methanol and 15 mL of water. The obtained precipitate is filtered and washed twice with methanol/water-solution (2:1). The solid is dried at 60° C. under vacuum. The desired product is obtained in 88% yield (1.1 g). $^1$H-NMR (400 MHz, CD$_2$Cl$_2$): δ=6.89 (d, 1H), 7.32-7.26 (m, 3H), 7.33 (s, 1H), 7.46 (t, 2H), 8.05 (d, 1H), 9.47 (s, 1H).

6.2 Intermediate 2

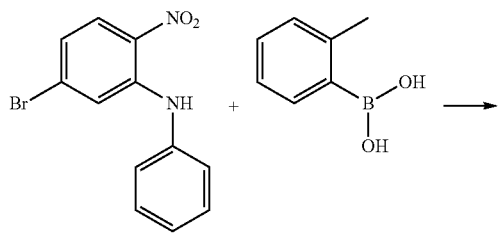

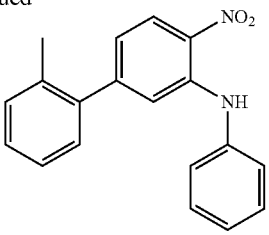

Intermediate 1 (1.0 g, 4.3 mmol) is suspended in 10 mL of dioxane and 2.5 mL of 5N NaOH solution. The mixture is purged with argon. Then 2-methylphenylboronic acid (1.09 g, 7.86 mmol) and Pd[P(tBu)$_3$]$_2$ (75 mg, 0.14 mmol) are added under argon atmosphere. The reaction mixture is heated to 85° C. and stirred for 15 h. After cooling to room temperature the reaction mixture is filtered over celite and washed with dichloromethane. The combined organic layers are washed with water, dried over anhydrous sodium sulphate and concentrated under vacuum. The residue is purified via column chromatography (silica, eluent: n-hexane/THF) and the desired product is obtained in 93% yield (1.2 g). $^1$H-NMR (400 MHz, CD$_2$Cl$_2$): δ=2.24 (s, 3H), 6.76 (d, 1H), 7.13 (s, 1H), 7.15 (d, 1H), 7.18-7.26 (m, 4H), 7.31 (d, 2H), 7.40 (t, 2H), 8.22 (d, 1H), 9.54 (s, 1H).

6.3 Intermediate 3

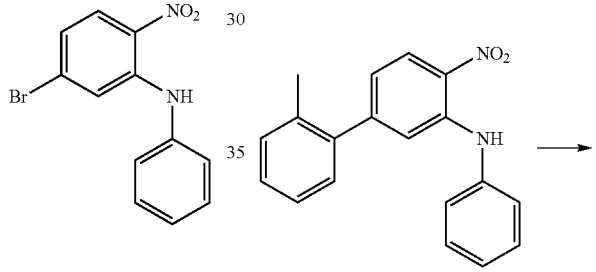

Intermediate 2 (736 mg, 2.42 mmol) is suspended in 30 mL of methanol. After adding 10 mL of THF the solid is solved in an ultrasonic bath. Saturated ammonia chloride solution (4 mL) is added and zinc powder (380 mg, 5.8 mmol) is added at room temperature. The yellow reaction mixture is stirred at room temperature for 18 h. Then 20 mL of THF and additional zinc powder (380 mg, 5.8 mmol) are added. After keeping the reaction mixture in an ultrasonic bath, the mixture is stirred at room temperature overnight. The solvent is evaporated and the residue is diluted in dichloromethane (50 mL). The suspension is filtered over celite and washed with dichloromethane. The filtrate is washed with water and then dried over Na$_2$SO$_4$. The desired product is obtained as a yellow solid (97%, 640 mg). $^1$H-NMR (400 MHz, CD$_2$Cl$_2$): δ=2.28 (s, 3H), 3.84 (s, 2H), 5.26 (s, 1H), 6.79 (m, 3H), 6.85 (d, 1H), 6.96 (d, 1H), 7.10 (s, 1H), 7.15-7.25 (m, 6H).

6.4 Intermediate 4

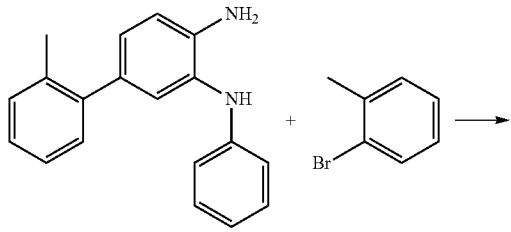

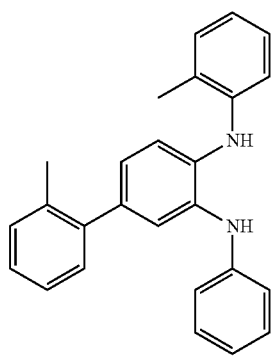

Intermediate 3 (0.27 g, 1.0 mmol), 2-bromotoluene (0.17 g, 1.0 mmol) and potassium carbonate (0.19 g, 1.4 mmol) in t-butanol (10 mL) is added 2-(Dicyclohexylphosphino)-3,6-dimethoxy-2,4,6-tri-Isopropyl-1,1-biphenyl (0.027 g, 0.05 mmol) and 2-Chloro-[2-(Dicyclohexylphosphino)3,6-dimethoxy-2,4,6-tri-Isopropyl-1,1-biphenyl]-[2-(2-aminoethyl)phenyl]palladium(II) (0.040 g, 0.05 mmol) under argon atmosphere. The reaction mixture is stirred at 40° C. for 30 minutes, then heated to 80° C. and stirred overnight. After cooling to room temperature the reaction mixture is diluted with dichloromethane and water. After separation of the layers, the organic layer is washed several times with water and then dried with anhydrous sodium sulphate. The organic layers are concentrated and the residue is purified via column chromatography (silica, eluent: cyclohexane/ethyl acetate). The desired product is obtained in 97% yield (0.35 g).

6.5 Intermediate 5

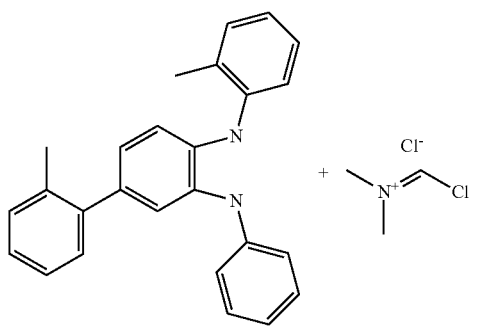

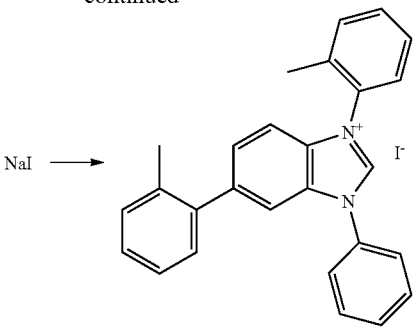

Intermediate 4 (2.0 g, 5.5 mmol) is suspended in 70 mL of acetonitrile and purged with argon. Then the mixture is cooled to 0° C. (Chlormethyl)-dimethylammonium chloride (2.11 g, 16.5 mmol) is added. The resulting solution is allowed to reach room temperature overnight while stirring. The mixture is cooled again to 0° C. and sodium iodide (2.47 g, 16.5 mmol), suspended in 10 mL of acetonitrile, is added. A yellow precipitate is forming. After stirring at 0° C. for 5 h the suspension is filtered and the solid is washed with acetonitrile. The filtrate is diluted with dichloromethane. The combined organic layers are washed several times with water, then dried over $Na_2SO_4$ and concentrated under vacuum. The desired product is obtained as a yellow solid in 95% yield (2.6 g). $^1$H-NMR (400 MHz, $CD_2Cl_2$): δ=2.26 (s, 3H), 2.35 (s, 3H), 7.21-7.32 (m, 4H), 7.49 (d, 1H), 7.52-7.61 (m, 2H), 7.62-7.77 (m, 6H), 7.93 (d, 1H), 8.10 (d, 2H), 10.84 (s, 1H).

6.6 Intermediate 6

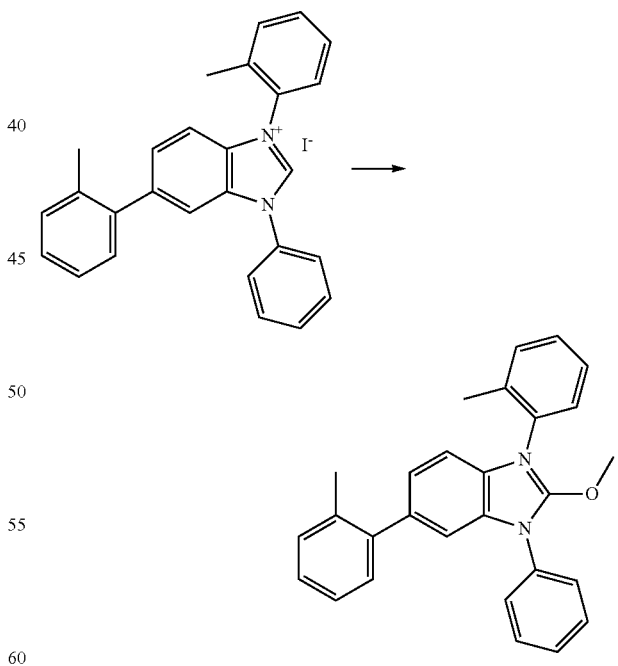

Intermediate 5 (1.0 g, 2.0 mmol) is solved in 60 mL of methanol and cooled to 0° C. Sodium methanolate (0.44 g, 2.4 mmol) in methanol is added dropwise. The mixture is stirred and allowed to reach room temperature overnight. The obtained suspension is cooled to 0° C. and filtered. The solid is washed two times with cold methanol and is then dried at 40° C. overnight. The desired product is obtained as a colorless solid (0.63 g, 64%). $^1$H-NMR (400 MHz, CD$_2$Cl$_2$): δ=2.29 (s, 3H), 2.33 (s, 3H), 3.23 (s, 3H), 6.38 (d, 1H), 6.68 (d, 1H), 6.81 (s, 1H), 7.06-7.49 (m, 11H), 7.56 (d, 2H).

6.7 Complex 6 (mer isomer)

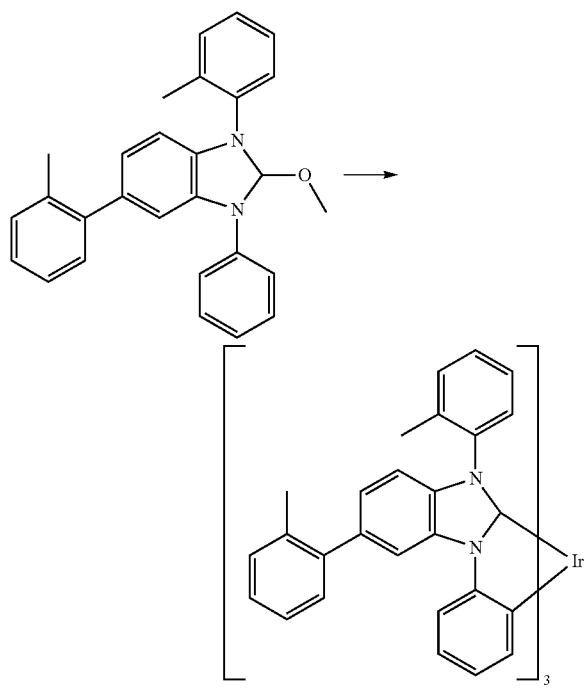

Intermediate 6 (0.61 g, 1.5 mmol) is solved in o-xylene (78 mL). Molecular sieves (5 Å and 3 Å, 0.5 g each), chloro([1,5]cyclooctadien)Iridium(I)-dimer (0.17 g, 0.25 mmol) and DMF (13 mL) are added to the solution. After purging with an argon flux for 5 minutes, the reaction is heated at 140° C. for 15 h. After cooling to room temperature, the solids are removed by filtration and washed with o-xylene. The filtrate is concentrated under vacuum and then purified several times via column chromatography (silica, eluent: 1× cyclohexane/dichloromethane; 2× toluene). The desired product is obtained in 4 isomers. MALDI-MS 1312

Photoluminescence (2% film in PMMA): λ$_{max}$=428 nm; τ$_0$=3.8 μs; PLQY=42%.

7 Synthesis of

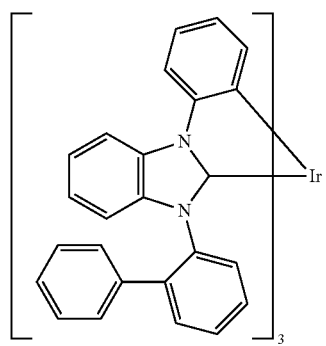

(Complex 7; mer Complex)

7.1 Intermediate 1

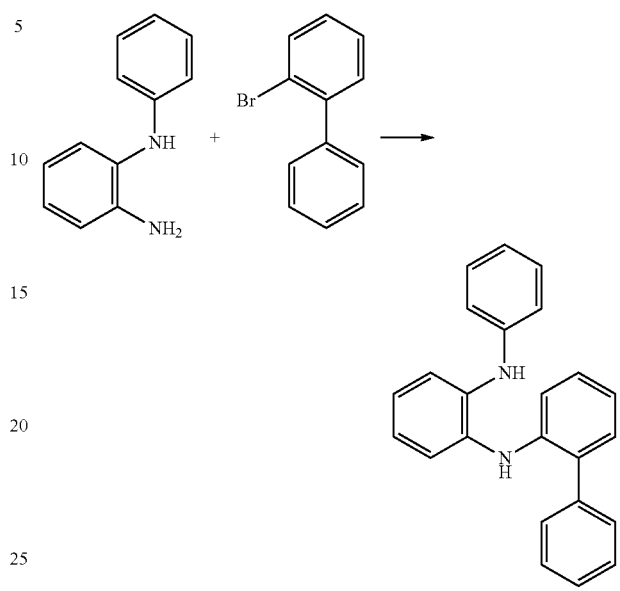

Under argon atmosphere N-phenyl-o-diaminobenzene (23.0 g, 122 mmol) and 2-brombiphenyl (29.1 g, 122 mmol) are suspended in toluene (275 mL). To this mixture xantphos (97%, 4.38 g, 7.34 mmol), Pd$_2$(dba)$_3$ (2.24 g, 2.45 mmol), NaOtBu (11.8 g, 122 mmol) and water (1.5 mL) are added. The reaction is stirred at reflux overnight. The reaction is cooled to room temperature and purged with argon for 10 minutes. Then additional xantphos (2.18 g, 3.67 mmol) and Pd$_2$(dba)$_3$ (1.11 g, 1.22 mmol) are added. The reaction is heated to reflux and stirred overnight. Then the reaction is again cooled to room temperature and purged with argon for 10 minutes. Then additional xantphos (2.18 g, 3.67 mmol) and Pd$_2$(dba)$_3$ (1.11 g, 1.22 mmol) are added for the third time. The reaction is heated to reflux and stirred overnight. After cooling to room temperature the suspension is filtered under vacuum and washed with toluene. The filtrate is concentrated under vacuum. The residue is purified via column chromatography (silica, cyclohexane/dichloromethane) and the desired product is obtained in 94% yield (39 g). $^1$H-NMR (400 MHz, CD$_2$Cl$_2$): δ=5.68 (d, 2H), 6.81 - 6.90 (m, 3H), 7.00 (m, 3H), 7.02 (d, 1H), 7.13 - 7.25 (q, 6H), 7.27 - 7.44 (m, 5H).

7.2 Intermediate 2

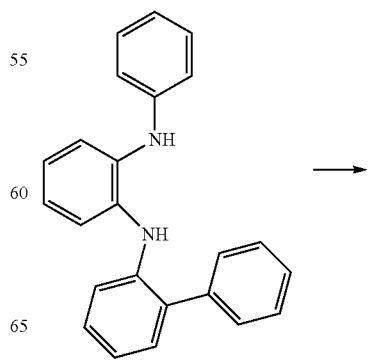

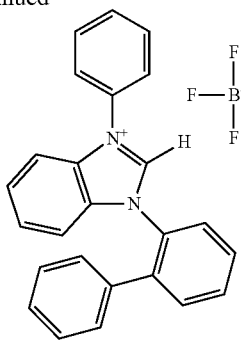

Intermediate 1 (600 mg, 1.8 mmol) is suspended in 5 mL of triethylorthoformate under argon atmosphere. To this mixture NH$_4$BF$_4$ (190 mg, 1.8 mmol) is added. The reaction is kept under reflux for 15 h. After cooling to room temperature the reaction mixture is diluted with CH$_2$Cl$_2$ and evaporated under vacuum. The brown residue is suspended in MeOtBu and ethyl acetate (10 mL, each) and is filtered and washed with MeOtBu. The product is dried at 45° C. for 15 h to give a solid (93%, 720 g). $^1$H-NMR (400 MHz, DMSO): δ=7.16-7.32 (m, 5H), 7.44 (d, 1H), 7.56 (t, 1H), 7.65 (t, 1H), 7.70-7.94 (m, 9H), 7.99 (d, 1H), 10.51 (s, 1H).

7.3 Complex 7 (mer isomer)

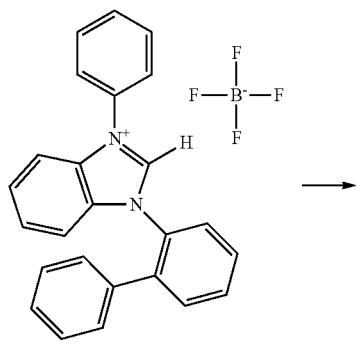

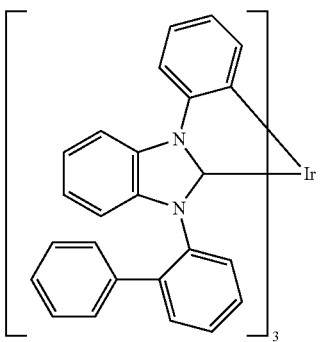

Tetrafluoroborate salt B (2.00 g, 4.61 mmol) is suspended in toluene (30 mL) and potassium hexamethyldisilizan (KHMDS, 0.5 M in toluene, 9.2 mL, 4.6 mmol) added dropwise over 25 min. The reaction mixture is stirred for 30 minutes at room temperature and then transferred dropwise within 20 minutes to a mixture of di-µ-chloro-bis[(cycloocta-1,5-dien)-iridium(I)] (310 mg, 0.46 mmol) in toluene (30 mL). The reaction mixture is heated reflux for 18 h. After cooling to room temperature the suspension is filtered and the residue is washed with toluene. The combined organic layers are concentrated. The formed solid is dissolved in dichloromethane (20 mL) and ethanol (40 ml). Solvent is removed until a precipitate is formed, which is filtered and washed with ethanol. This procedure is repeated for a second time. Then the solid is suspended in THF (30 mL), the residue filtered and the filtrate is slightly concentrated to yield a second portion of solid, which both contain the meridional isomer of the complex (21%).

Photoluminescence (2% film in PMMA): $\lambda_{max}$=434 nm; $\tau_0$=17 µs; PLQY=27%.

8 Synthesis of

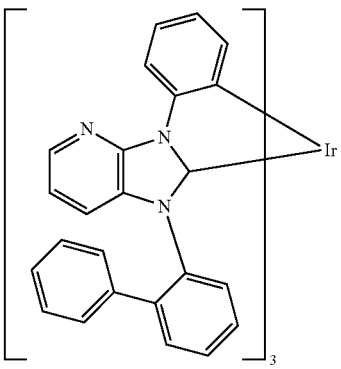

(Complex 8; mer Complex)

8.1 Intermediate 1

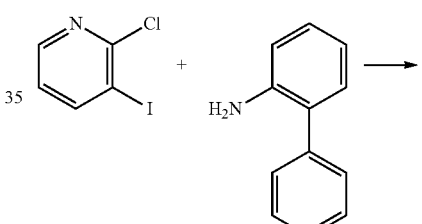

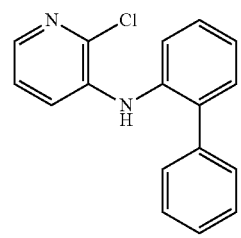

In 36 mL of toluene 2-chloro-3-iodpyridine (1.4 g, 6.0 mmol) and (1.0 g, 5.7 mmol) 2-aminobiphenyl are added under argon atmosphere. The suspension is degassed 10 min with argon flux, then BINAP (112 mg, 0.18 mmol) and Pd(OAc)$_2$ (40 mg, 0.18 mmol) are added. The suspension is stirred a few minutes then cesium carbonate (9.7 g, 30 mmol) and triethyl amine (550 mg, 5.4 mmol) are added. The suspension is stirred for 5 minutes at room temperature and is then heated to reflux. The reaction is stirred for 4 h, then BINAP (112 mg, 0.18 mmol) and Pd(OAc)$_2$ (40 mg, 0.18 mmol) are added. After stirring over night at reflux, again BINAP (112 mg, 0.18 mmol) and Pd(OAc)$_2$ (40 mg, 0.18 mmol) are added. The reaction is stirred at reflux for 15 h. After cooling to room temperature, the suspension is filtered under vacuum and washed with toluene. The filtrate is concentrated to 3 mL. The residue is diluted with methanol. A brown precipitate is formed. After filtration the filtrate is concentrated. The residue is purified via column chromatography (silica, eluent: cyclohexane/dichloromethane) and the desired product is obtained in 77% yield (1.24 g). $^1$H-NMR (400 MHz, CD$_2$Cl$_2$): δ=6.10 (s, 1H), 7.03-7.10 (m, 1H), 7.15-7.24 (m, 1H), 7.32-7.48 (m, 9H), 7.79 (d, 1H).

8.2 Intermediate 2

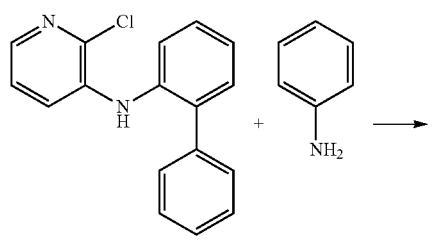

Intermediate 1 (14.3 g, 50.8 mmol) and aniline (5.06 g, 54.3 mmol) are suspended in 175 mL of toluene. The mixture is degassed for 10 minutes with argon. Then BINAP (1.42 g, 2.28 mmol) and Pd$_2$(dba)$_3$ (697 mg, 0.761 mmol) are added. The mixture is stirred a 5 minutes at room temperature. Then sodium tert-butylat (7.04 g, 71.1 mmol) is added. After stirring for 5 min at room temperature, the mixture is heated to reflux for 15 h. After cooling to room temperature the suspension is filtered and washed with toluene. The filtrate is concentrated. The residue is charged on celite and purified via column chromatography (silica, eluent toluene/ethyl acetate). The obtained product fractions are concentrated under reduced pressure. The solid is solved in dichloromethane and diluted with the same amount of methanol. After removing a part of the solvent a white precipitate is formed. The solid is filtered and washed with methanol. The desired product is obtained in 45% yield (7.76 g). $^1$H-NMR (400 MHz, CD$_2$Cl$_2$): δ=5.29 (s, 1H), 6.71 (d, 1H), 6.73-6.79 (m, 1H), 6.91-7.00 (m, 3H), 7.18 (t, 1H), 7.21-7.30 (q, 3H), 7.34-7.42 (m, 2H), 7.44-7.57 (m, 6H), 8.05 (d, 1H).

8.3 Intermediate 3

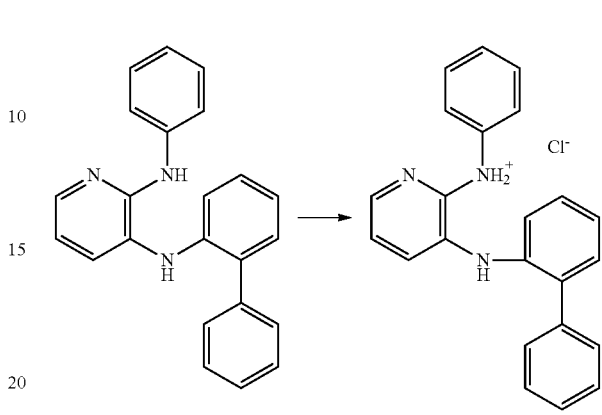

Intermediate 2 (7.70 g, 22.8 mmol) is suspended in 180 mL of hydrochloric acid (32%) at room temperature. The suspension is stirred at room temperature for 15 h. After treatment in an ultrasonic bath the mixture is stirred at 30° C. for 15 h. The suspension is filtered and the residue is washed with water. After drying at 45° C. the desired product is obtained in 96% yield (8.22 g). $^1$H-NMR (400 MHz, CD$_2$Cl$_2$): δ=4.38 (s, 1H), 6.69 (t, 1H), 6.96 (d, 1H), 7.20-7.35 (m, 7H), 7.35-7.44 (m, 4H), 7.45-7.56 (m, 4H), 8.08 (s, 1H), 10.09 (s, 1H), 8.4 Intermediate 4

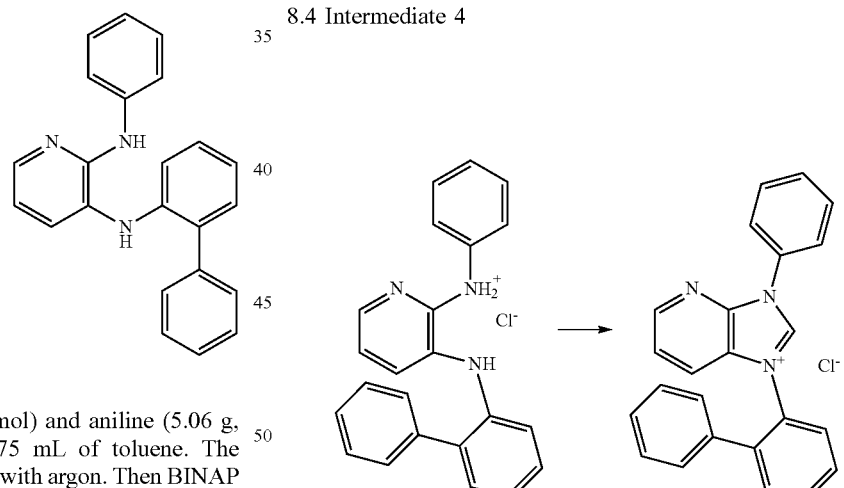

Intermediate 3 (300 mg, 0.80 mmol) is suspended in 5 mL of triethyl ortho formate. The reaction is heated to reflux and stirred for 15 h. After cooling to room temperature the suspension is filtered and washed a few times with ethyl acetate. The solid is dried at 45° C. under vacuum. The desired product is obtained in 84% yield (260 mg). $^1$H-NMR (400 MHz, DMSO): δ=7.20-7.30 (m, 3H), 7.36 (d, 2H), 7.58-7.65 (q, 1H), 7.69-7.87 (m, 5H), 7.91 (t, 1H), 7.97 (t, 3H), 8.05 (d, 1H), 8.73 (d, 1H), 10.90 (s, 1H).

8.5 Complex 8 (mer Isomer)

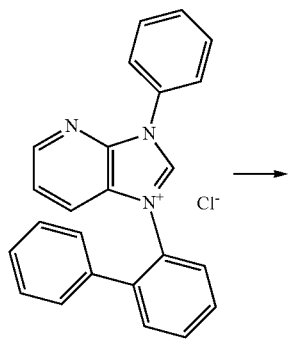

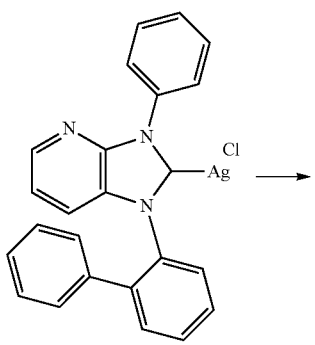

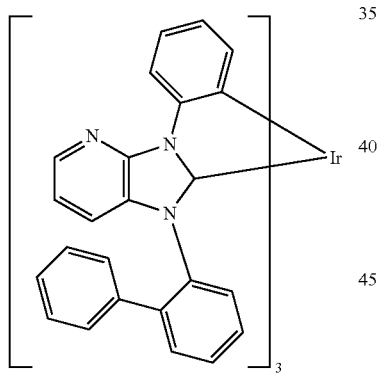

Intermediate 4 (3.38 g, 8.81 mmol) is suspended in 100 mL of anhydrous acetonitrile. The suspension is sparkled with argon flux for 10 minutes. Then silver oxide (1.03 g, 4.40 mmol) is added to the suspension and the reaction is stirred at room temperature for 18 h. The suspension is evaporated under reduced pressure. The solid is diluted with anhydrous o-xylene, then [Ir(COD)Cl]$_2$ (600 mg, 0.88 mmol) is added. Under an argon flux the reaction is heated to reflux for 18 h. After cooling to room temperature the brown reaction mixture is filtered under vacuum. The filtrate is evaporated and the residue is solved in a few mL of dichloromethane. This solution is diluted with 100 mL of ethanol, while a solid is formed. The precipitate is filtered and dried at 40° C. The mixture is purified via column chromatography (silica, eluent: cyclohexane/ethyl acetate) to yield the product as light yellow solid (0.53 g, 25%).

Photoluminescence (2% film in PMMA): $\lambda_{max}$=455 nm; $\tau_0$=1.3 μs; PLQY=79%.

9 Synthesis of

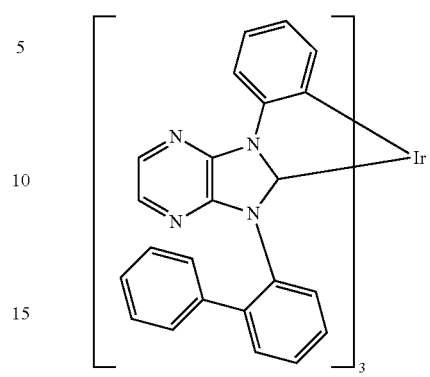

(Complex 9; mer Complex)

9.1 Intermediate 1

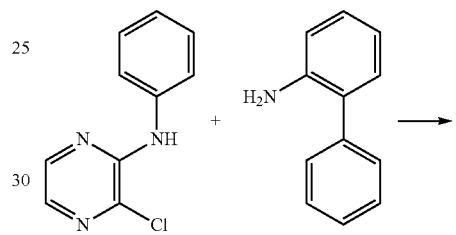

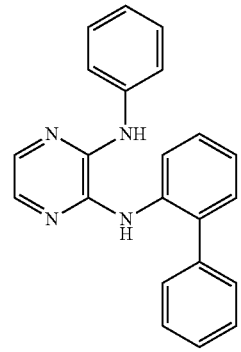

1-Amino-2-chloropyrazine (4.64 g, 22.6 mmol), 2-aminobiphenyl (4.72 g, 22.1 mmol) and cesium carbonate (8.82 g, 27.1 mmol) are suspended in 125 mL of THF under argon atmosphere. The suspension is degassed 10 minutes under argon flux. Then BrettPhos (250 mg, 0.45 mmol) and BrettPhos Palladacycle (370 mg, 0.45 mmol) are added. The suspension is stirred a few minutes at room temperature and is then heated to reflux for 18 h. After cooling to room temperature the reaction mixture is filtered over silica gel and washed with THF. The filtrate is evaporated under vacuum. The residue is stirred in 50 mL of acetonitrile. The suspension is filtered and the residue is washed twice with a few mL of acetonitrile. The solid is dried at 45° C. under reduced pressure. The solid is recrystallized (100 mL of acetonitrile, drying at 45° C.) to yield the product in 58% yield (4.48 g). $^1$H-NMR (400 MHz, CD$_2$Cl$_2$): δ=6.09 (s, 1H), 6.28 (s, 1H), 7.00 (t, 1H), 7.12 (t, 1H), 7.17 (d, 2H), 7.26 (t, 3H), 7.30-7.44 (m, 6H), 7.73 (d, 2H), 7.83 (d, 1H).

9.2 Intermediate 2

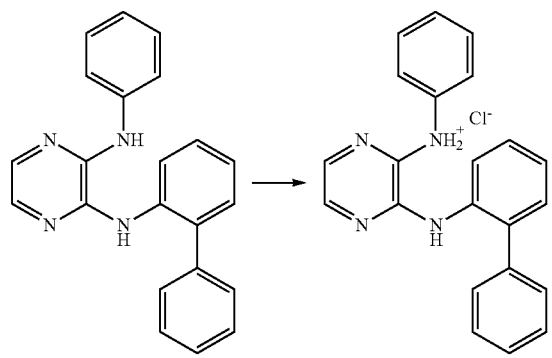 [SMILES: c1ccc(Nc2nccnc2Nc2ccccc2-c2ccccc2)cc1 ; c1ccc(Nc2nccnc2Nc2ccccc2-c2ccccc2)cc1 ; [Cl-]]

Intermediate 1 (1.00 g, 2.96 mmol) is suspended in 65 mL of hydrochloric acid (32%) at room temperature under nitrogen atmosphere. The mixture is stirred for 2 h at room temperature. Then the mixture is poured into 200 mL of water. The yellow precipitate is filtered and washed with water. After drying at 45° C. the desired product is obtained in 81% yield (0.81 g). 1H-NMR (400 MHz, $CD_2Cl_2$): δ=7.05-7.10 (m, 2H), 7.22-7.28 (m, 1H), 7.30-7.36 (m, 4H), 7.40 (d, 1H), 7.45-7.53 (m, 6H), 7.75 (d, 2H), 9.60 (br.s, 1H), 10.50 (br.s, 1H).

9.3 Intermediate 3

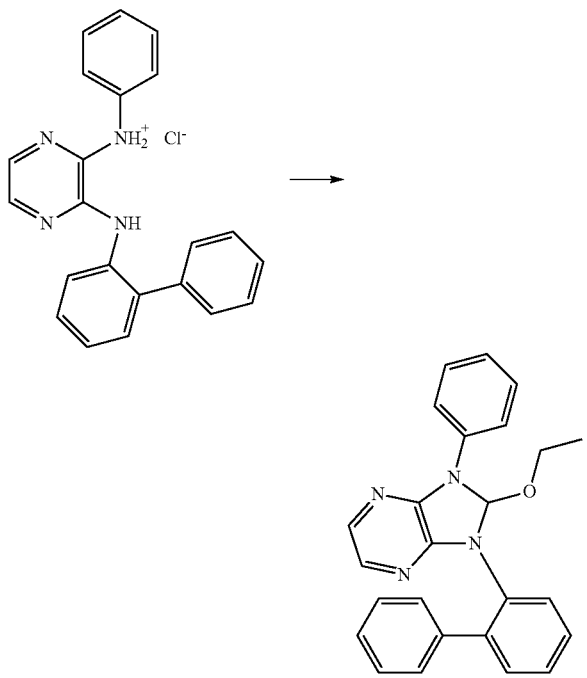

Intermediate 2 (975 mg, 2.27 mmol) is suspended in 42 mL of triethylorthoformate. The reaction is stirred for 1 h at room temperature, then 2 h at 50° C. and then 2 h at 70° C. Then the reaction is stirred at room temperature overnight. The reaction is concentrated under vacuum. The yellow residue is suspended in ethanol and sonificated. The solid is filtered and washed with anhydrous ethanol. After drying at 40° C. the desired product is obtained in 77% yield (0.8 g). $^1$H-NMR (400 MHz, $CD_2Cl_2$): δ=0.87 (t, 3H), 3.10-3.29 (m, 2H), 6.27 (s, 1H), 7.10 (t, 1H), 7.24-7.38 (m, 8H), 7.41 (d, 1H), 7.45-7.55 (m, 3H), 7.57-7.69 (d, 2H).

9.4 Complex 9 (mer Isomer)

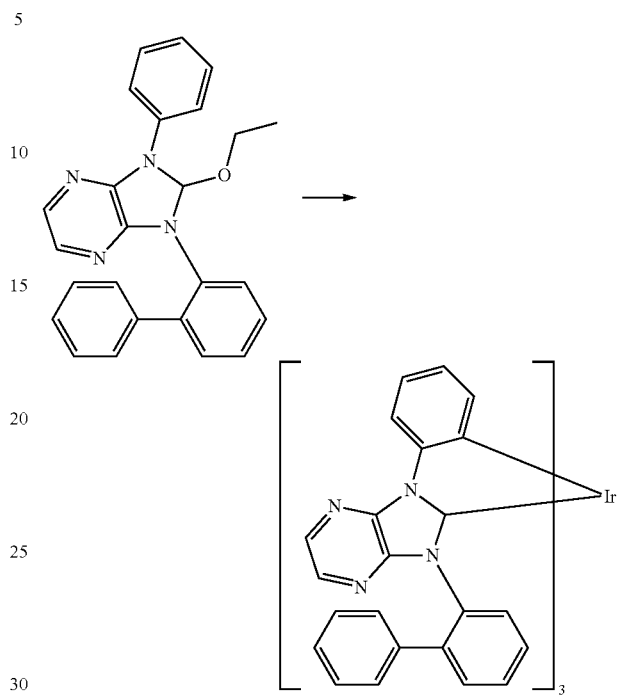

Intermediate 3 (660 mg, 1.67 mmol) and [Ir(COD)Cl]$_2$ (112.38 mg, 0.167 mmol) are suspended in 10 mL of anhydrous o-xylene. The reaction is sparkled with argon for 10 minutes and then heated to reflux for 18 h. After cooling to room temperature, the suspension is filtered and the filtrate is evaporated under vacuum. The brown residue is suspended in 10 mL of ethanol. The solid is filtered and washed with a few mL of ethanol. The solid is solved in dichloromethane and diluted with ethanol. The solution is evaporated under vacuum until a yellow precipitate is formed. This mixture is stirred at room temperature for 18 h. After filtering the suspension, the solid is washed with a few mL of ethanol. Then the product is purified via column chromatography (silica, eluent: cyclohexane/ethyl acetate). The product is isolated in 17% yield (69 mg). Maldi-MS 1235 (M+H)

Photoluminescence (2% film in PMMA): $\lambda_{max}$=521 nm; $\tau_0$=1.3 µs; PLQY=63%.

B Device Examples

Device examples: all initial performance given at 1000 cd/m$^2$

1 OLED Comprising Complex 1 as Emitter (E-X)

40 nm HIL Plexcore AJ20-1000—10 nm Ir(DPBIC)$_3$: MoO$_3$ (50:50)—10 nm Ir(DPBIC)$_3$—40 nm E-X/Ir(DPBIC)$_3$/SH-2 (10:10:80)—5 nm SH-2-25 nm ETM-2:Liq (50:50)—4 nm KF—100 nm Al

| Example | E-X | Voltage [V] | CurrEff [cd/A] | LumEff [lm/W] | EQE [%] | CIE x, y | LT$_{50}$ [relative value][1] |
|---|---|---|---|---|---|---|---|
| Device 1.1 | Complex 1 | 5.3 | 44.7 | 26.4 | 13.9 | 0.34; 0.56 | 2500% |

[1]in view of the OLED in example 3 with complex 3V as E-X

2 OLED Comprising Complex 1 or 2 as Emitter (E-X)

40 nm HIL Plexcore AJ20-1000—10 nm Ir(DPBIC)$_3$:MoO$_3$ (90:10)—10 nm Ir(DPBIC)$_3$—40 nm E-X/Ir(DPBIC)$_3$/SH-2 (10:10:80)—5 nm SH-2-20 nm ETM-2:Liq (50:50)—4 nm KF—100 nm Al

| Example | E-X | Voltage [V] | CurrEff [cd/A] | LumEff [lm/W] | EQE [%] | CIE x, y | LT$_{50}$ [relative values][1] |
|---|---|---|---|---|---|---|---|
| Device 2.1 | Complex 2 | 5.9 | 43.6 | 23.4 | 13.9 | 0.32; 0.55 | 1500% |
| Device 2.2 | Complex 1 | 5.1 | 45.1 | 27.8 | 14.1 | 0.35; 0.56 | 2200% |

[1] in view of the OLED in example 3 with complex 3V as E-X

3 OLED Comprising Complex 3 or 3V (Comparative Example) as Emitter (E-X)

40 nm HIL Plexcore AJ20-1000—10 nm Ir(DPBIC)$_3$:NDP-9 (99:1)—10 nm Ir(DPBIC)$_3$ —40 nm O18742/Ir(DPBIC)$_3$/SH-2 (10:10:80)—5 nm SH-2-25 nm ETM-2:Liq (50:50)—4 nm KF—100 nm Al

| Example | E-X | Voltage [V] | CurrEff [cd/A] | LumEff [lm/W] | EQE [%] | CIE x, y | LT$_{50}$ [relative value] |
|---|---|---|---|---|---|---|---|
| Device 3.1 (comp. example) | Complex 3V | 4.8 | 41.3 | 27.1 | 17.2 | 0.21; 0.38 | 100% |
| Device 3.2 | Complex 3 | 4.5 | 42.1 | 29.1 | 15.8 | 0.23; 0.44 | 490% |

Comparative Complex 3V:

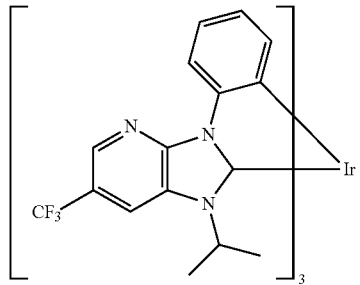

(described in WO 2012/172482)

4 OLED Comprising Complexes 5 or 9 as Emitter (E-X)

40 nm HIL Plexcore AJ20-1000—10 nm Ir(DPBIC)$_3$:MoO$_3$ (90:10)—10 nm Ir(DPBIC)$_3$—40 nm E-X/Ir(DPBIC)$_3$/SH-2 (10:10:80)—5 nm SH-2-20 nm ETM-2:Liq (50:50)—4 nm KF—100 nm Al
Device 4.1: E-X: Complex 5
Device 4.2: E-X: Complex 9

Luminescent OLEDs with long lifetimes are obtained in examples 4.1 and 4.2.

5 OLED Comprising Complexes 4 or 8 as Emitter (E-X)

40 nm HIL Plexcore AJ20-1000—10 nm Ir(DPBIC)$_3$:MoO$_3$ (90:10)—10 nm Ir(DPBIC)$_3$—40 nm E-X/Ir(DPBIC)$_3$/SH-2 (10:10:80)—5 nm Host-X—20 nm ETM-2:Liq (50:50)—4 nm KF—100 nm Al
Device 5.1: E-X: Complex 4
Device 5.2: E-X: Complex 8

Luminescent OLEDs with long lifetimes are obtained in examples 5.1 and 5.2.

6 OLED Comprising Complex 4 (Mer) or 4V (Comparative Example) as Emitter (E-X)

ITO 120 nm—Ir(DPBIC)$_3$:MoO$_3$ (90:10) 90 nm—Ir(DPBIC)$_3$ 10 nm—Emitter:Host-X (% Host-X=100%-% Emitter) 40 nm—Host-X 5 nm—ETM-2:Liq (50:50) 25 nm—KF 4 nm—Alu

| Emitter | % Emitter | Voltage [V] | CurrEff [cd/A] | LumEff [lm/W] | EQE [%] | CIEx | CIEy | LT$_{50}$ [relative value] |
|---|---|---|---|---|---|---|---|---|
| 4V | 30 | 5.22 | 16.46 | 9.91 | 12.65 | 0.152 | 0.167 | 100% |
| 4 | 30 | 5.35 | 12.86 | 7.55 | 8.72 | 0.161 | 0.190 | 367% |
| 4V | 40 | 4.72 | 18.73 | 12.46 | 13.23 | 0.152 | 0.188 | 100% |
| 4 | 40 | 5.25 | 12.68 | 7.58 | 7.65 | 0.167 | 0.229 | 300% |

Diaryl substituted, yet meridional, emitters show better lifetime in OLEDs than those with monoaryl-monoalkyl substituted meridional emitters.

Comparative Complex 4V:

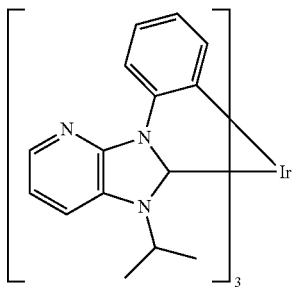

(mer Em-2, described in WO 2012/172482)

Host-X in devices 5.1 and 5.2 and 6 has the following formula:

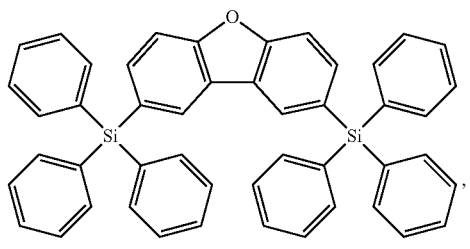

(published in WO2009/003898, compound 4g)

SH-2 and ETM-2 employed in the devices mentioned above have the following formulae:

SH-2

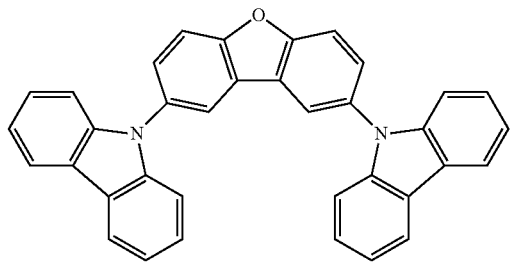

-continued

ETM-2

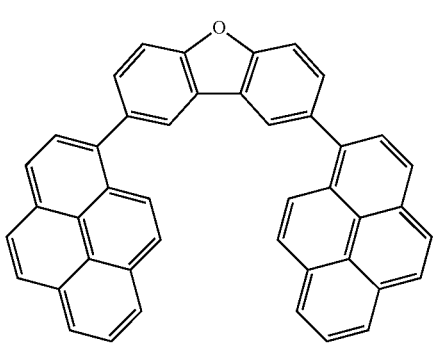

The invention claimed is:

1. A process for preparing cyclometallated Ir complex of formula (I):

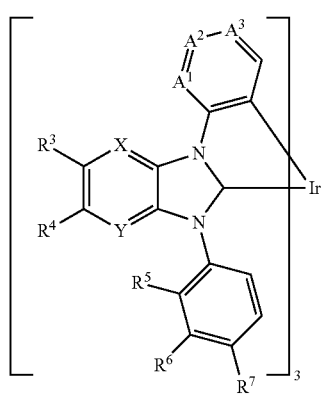

(I)

wherein a weight ratio of mer to fac isomer of the cyclometallated Ir complex of formula (I) is 100% - 60% (mer) to 0% to 40% (fac),
wherein
$A^1$ is CH or N;
$A^2$ is $CR^1$ or N;
$A^3$ is $CR^2$ or N
wherein in the case that $A^1$ and/or $A^3$ are N, $A^2$ is $CR^1$;
$R^1$, $R^2$, $R^3$, $R^4$, $R^6$ and $R^7$ are each independently hydrogen; deuterium; a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action; selected from the group consisting of methoxy, phenyloxy, halogenated $C_1$-$C_4$-alkyl, halogen, CN, $SiR^{10}R^{11}R^{12}$, diphenylamino and —C(O)O$C_1$-$C_4$-alkyl;
$R^{10}$, $R^{11}$, $R^{12}$ are each independently a linear or branched alkyl radical, having from 1 to 6 carbon atoms; a substituted or unsubstituted aryl radical, having from 6 to 12 carbon atoms; a substituted or unsubstituted heteroaryl radical, having a total of from 5 to 15 carbon atoms and/or heteroatoms; a substituted or unsubstituted cycloalkyl radical having a total of from 3 to 7 carbon atoms;
or
$R^1$ and $R^2$, $R^3$ and $R^4$ and/or $R^6$ and $R^7$ may form, independently of each other, together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms;
$R^5$ is a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action, selected from the group consisting of methoxy, phenyloxy, halogenated $C_1$-$C_4$-alkyl, halogen, CN, $SiR^{10}R^{11}R^{12}$, diphenylamino and —C(O)O$C_1$-$C_4$-alkyl;
X is CH, CD or N;
Y is $CR^8$ or N;
$R^8$ is hydrogen; deuterium; a linear or branched, substituted or unsubstituted alkyl radical having from 1 to 20 carbon atoms, optionally interrupted by at least one heteroatom, selected from O, S and N; a substituted or unsubstituted cycloalkyl radical having a total of from 3 to 30 carbon atoms; a substituted or unsubstituted heterocyclo alkyl radical, interrupted by at least one heteroatom selected from O, S and N and having a total of from 3 to 30 carbon atoms and/or heteroatoms; a substituted or unsubstituted aryl radical, having a total of from 6 to 30 carbon atoms; a substituted or unsubstituted heteroaryl radical, having a total of from 5 to 30 carbon atoms and/or heteroatoms, selected from O, S and N; or a group with donor or acceptor action, selected from the group consisting of methoxy, phenyloxy, halogenated $C_1$-$C_4$-alkyl, halogen, CN, $SiR^{10}R^{11}R^{12}$, diphenylamino and —C(O)O$C_1$-$C_4$-alkyl;
by contacting suitable compounds comprising Ir with appropriate ligand precursors,
wherein suitable compounds comprising Ir are complexes of iridium with halides, 1,5-cyclooctadiene, cyclooctene, phosphines, cyanides, alkoxides, pseudohalides and/or alkyl ligands, and appropriate ligand precursors are Ag-carbene complexes corresponding to the Ir complex of formula (I) or compounds of the general formula (IV)

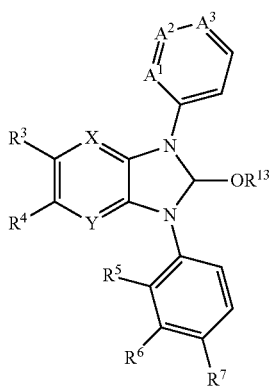

(IV)

wherein $A^1$, $A^2$, $A^3$, $R^3$, $R^4$, $R^6$, $R^5$, $R^7$, X and Y are each as already defined above for the compounds of the general formula (I), and $R^{13}$ is defined as follows:
$R^{13}$ is independently $SiR^{14}R^{15}R^{16}$, aryl, heteroaryl, alkyl, cycloalkyl or heterocycloalkyl,
$R^{14}$, $R^{15}$, $R^{16}$ are each independently aryl, heteroaryl, alkyl, cycloalkyl or heterocycloalkyl.

2. The process according to claim 1, wherein
$R^1$, $R^2$, $R^3$, $R^4$, $R^6$ and $R^7$ are each independently hydrogen; deuterium; methyl, ethyl, n-propyl, iso-propyl, n-butyl, tert-butyl, sec-butyl, iso-butyl, cyclopentyl, cyclohexyl, $OCH_3$, $OCF_3$; phenyl, pyridyl, primidyl, pyrazinyl, carbazolyl, dibenzofuranyl, dibenzothiophenyl, benzofuranyl and benzothiophenyl wherein the aforementioned radicals may be unsubstituted or substituted by methyl, ethyl, n-propyl, iso-propyl, n-butyl, tert-butyl, sec-butyl, iso-butyl, methoxy, $CF_3$ or phenyl; a group with donor or acceptor action, selected from F, $CF_3$, CN and $SiPh_3$; and
$R^5$ is methyl, ethyl, n-propyl, iso-propyl, n-butyl, tert-butyl, sec-butyl, iso-butyl, cyclopentyl, cyclohexyl, $OCH_3$, $OCF_3$; phenyl, pyridyl, primidyl, pyrazinyl, wherein the aforementioned radicals may be substituted by, preferably monosubstituted, by methyl, ethyl, n-propyl, iso-propyl, n-butyl, tert-butyl, sec-butyl, iso-butyl, methoxy or phenyl or unsubstituted; a group with donor or acceptor action, selected from $CF_3$ and CN.

3. The process according to claim 1, wherein
$R^1$, $R^2$, $R^3$, $R^4$, $R^6$ and $R^7$ are each independently hydrogen; deuterium; methyl, ethyl, n-propyl, iso-propyl, n-butyl, tert-butyl, sec-butyl, iso-butyl; phenyl, pyridyl, primidyl, pyrazinyl, carbazolyl, dibenzofuranyl, dibenzothiophenyl, wherein the aforementioned radicals may be unsubstituted or substituted by methyl, ethyl, iso-propyl, tert-butyl, iso-butyl or methoxy; $CF_3$ or CN; and
$R^5$ is methyl, ethyl, n-propyl, iso-propyl, n-butyl, sec-butyl, iso-butyl; phenyl, tolyl or pyridyl.

4. The process according to claim 1, wherein
X, Y are each independently CH, CD or N.

5. The process according to claim 1, wherein
X is N; and
Y is $CR^8$.

6. The process according to claim 1, wherein
X is N; and
Y is N.

7. The process according to claim 1, wherein
X is CH or CD; and
Y is $CR^8$.

8. The process according to claim 1, wherein the cyclometallated Ir complex one of the following formulae:

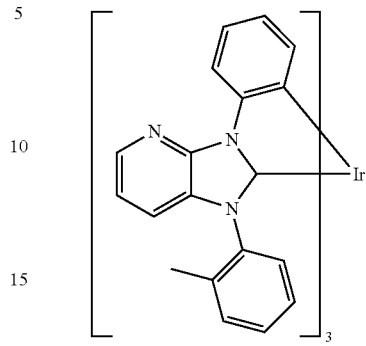

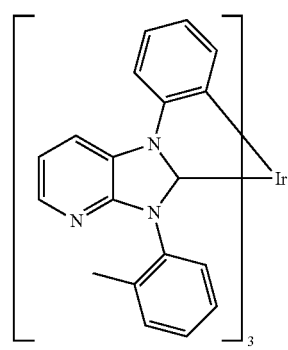

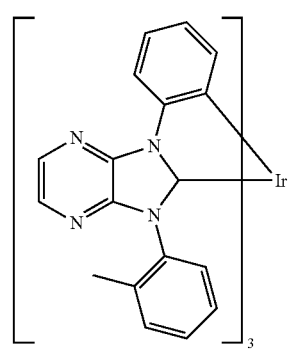

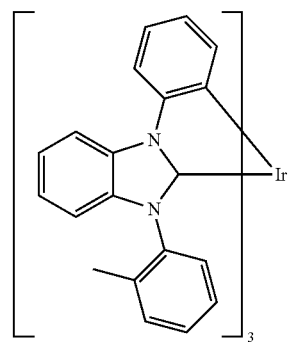

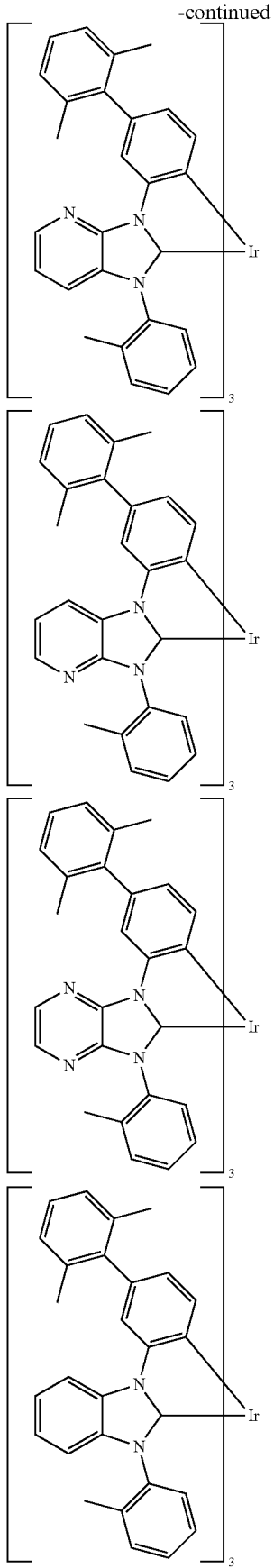
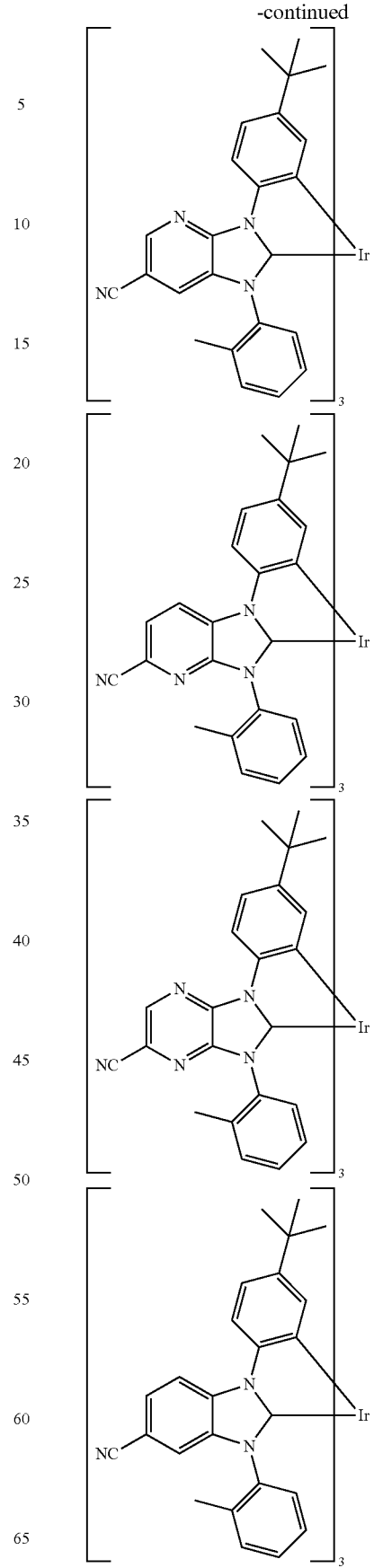

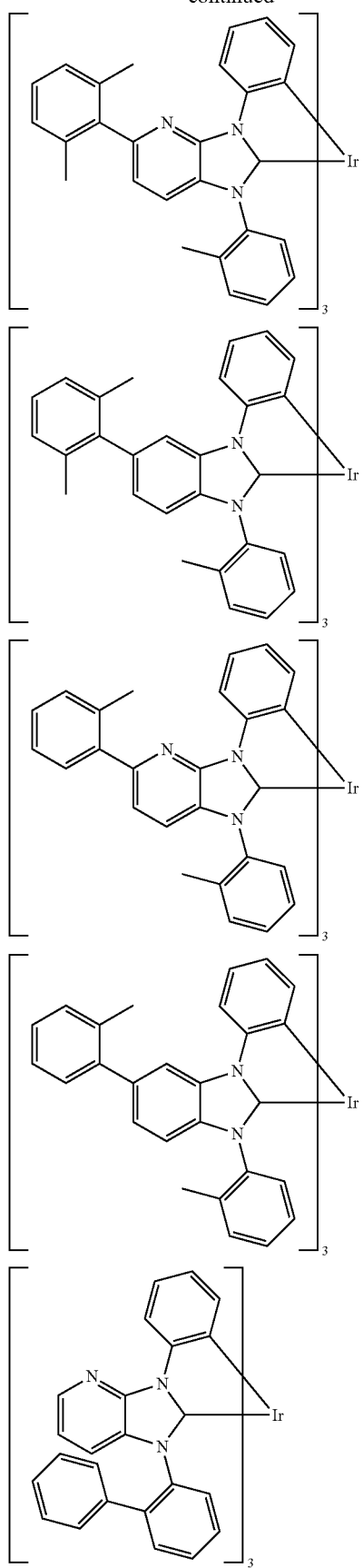
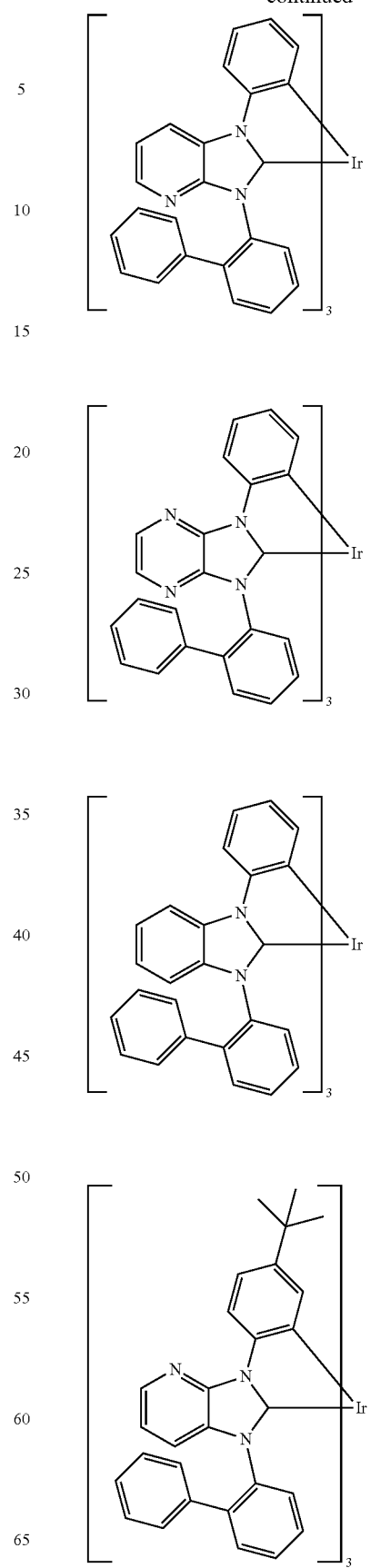

-continued
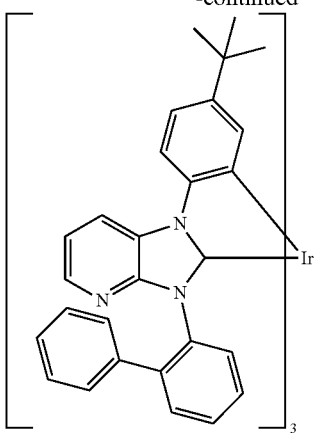
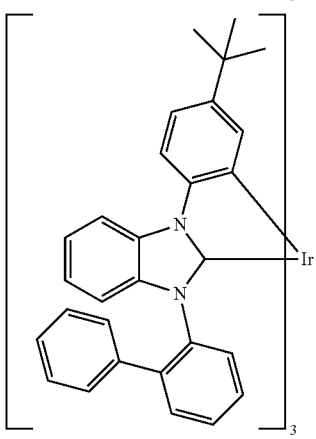
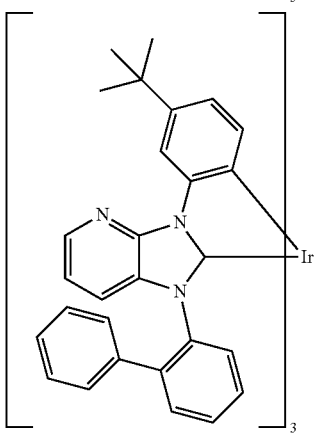
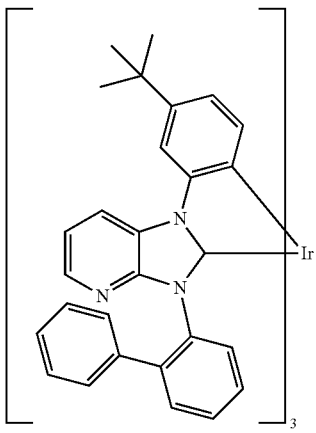
-continued
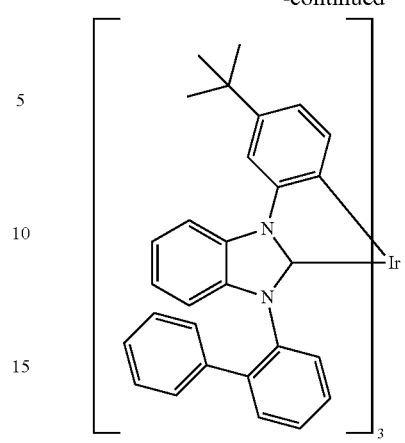
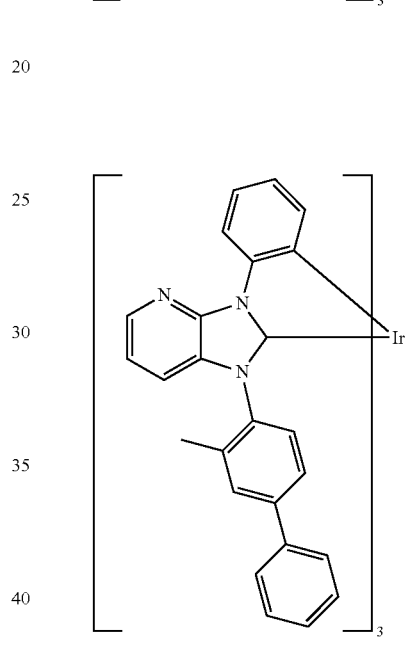
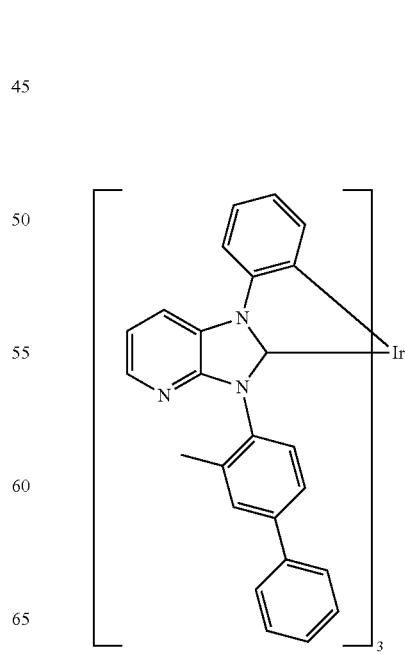

-continued
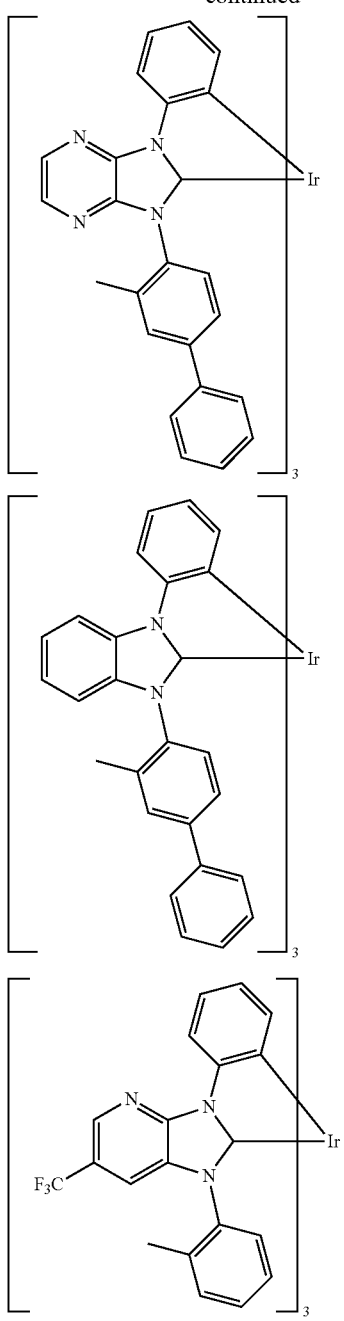
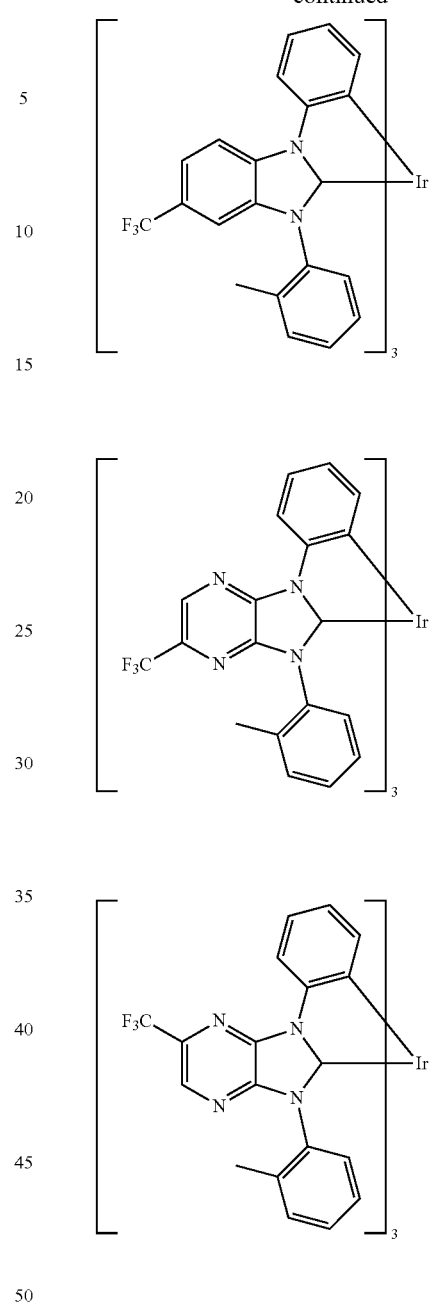
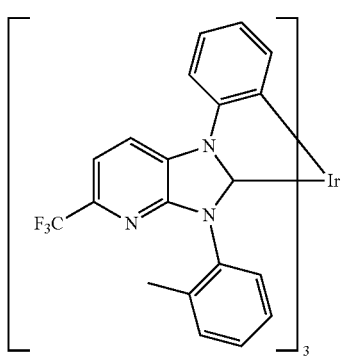
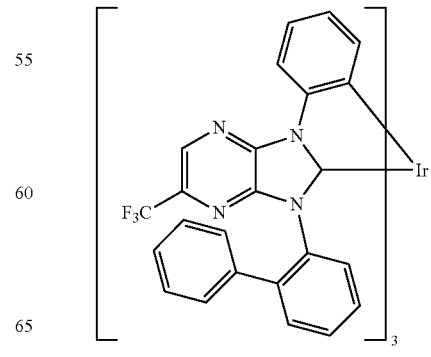

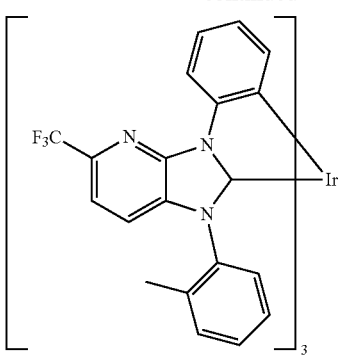
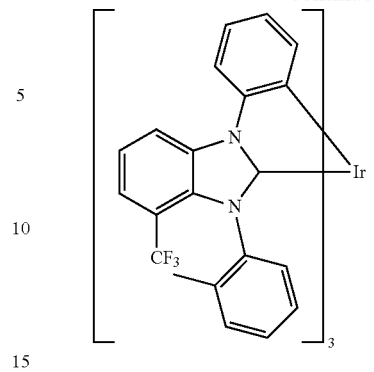
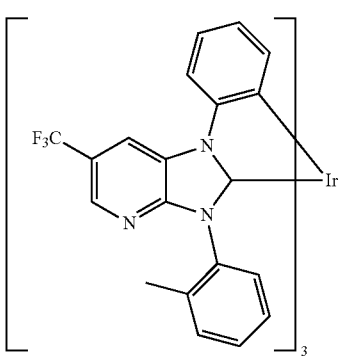
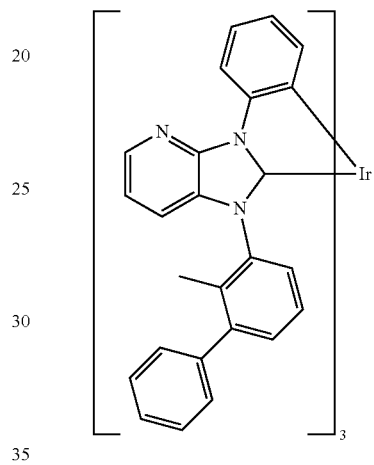
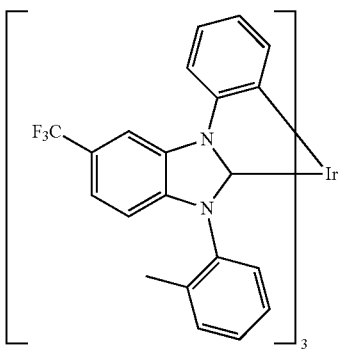
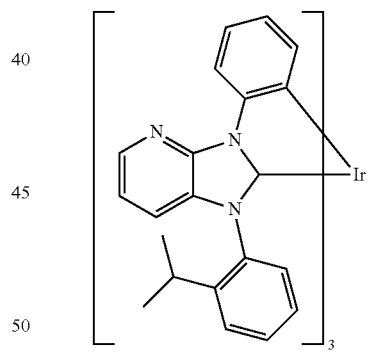
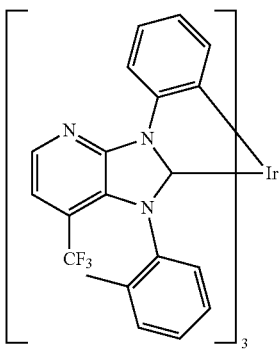
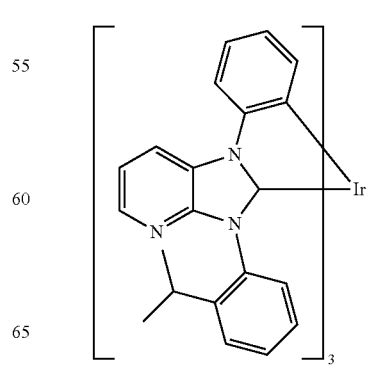

147
-continued
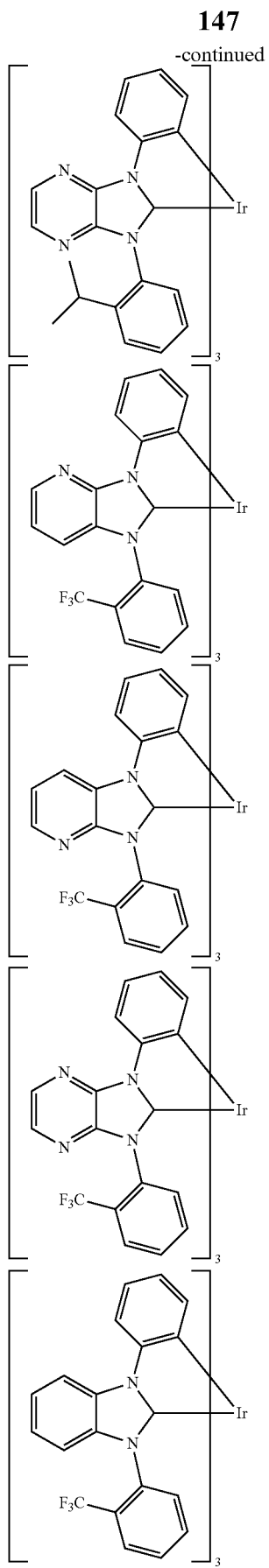
148
-continued
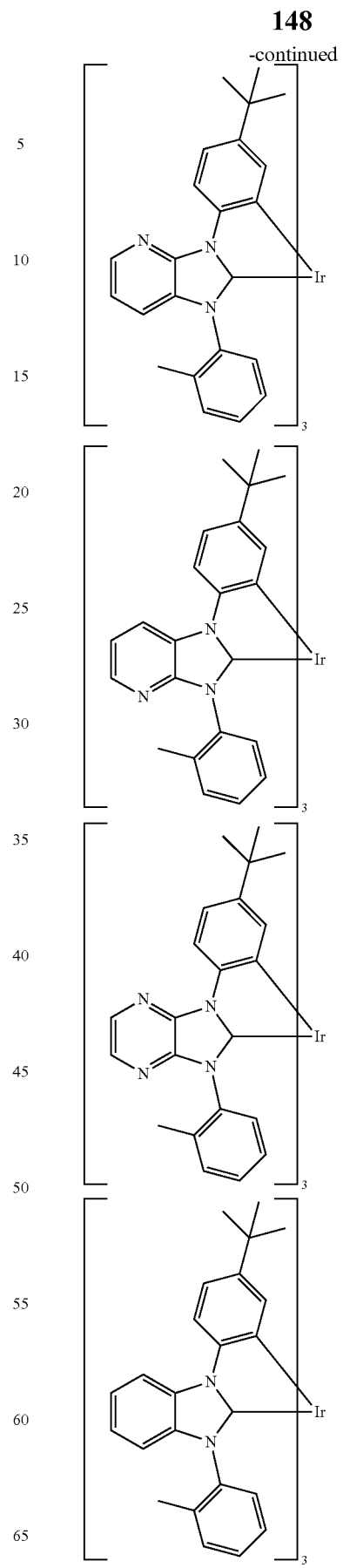

149
-continued
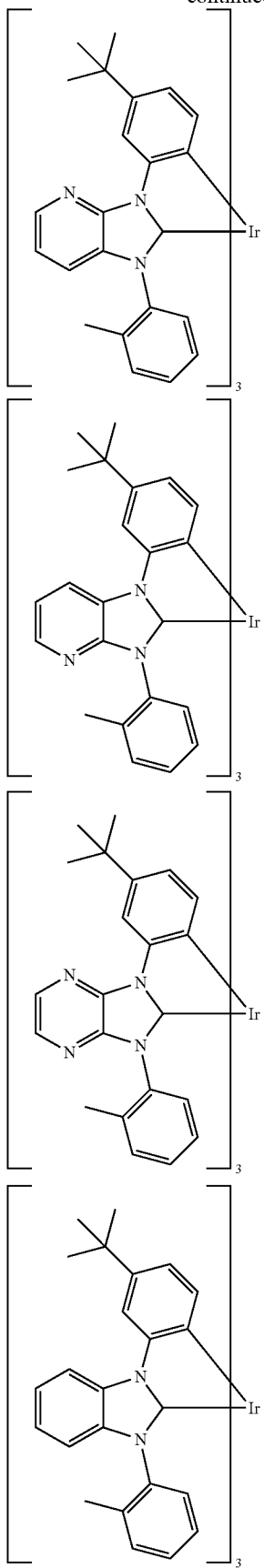
150
-continued
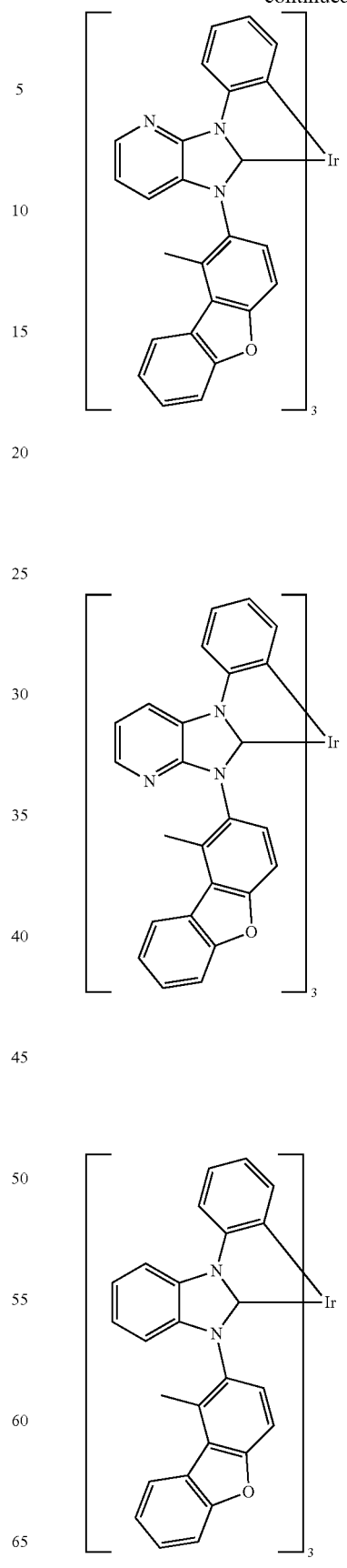

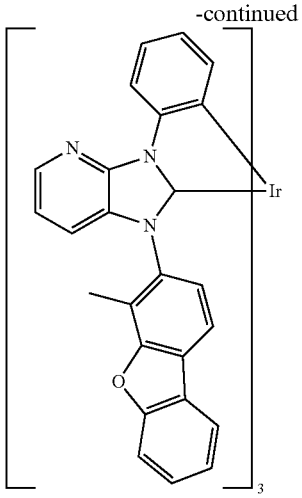

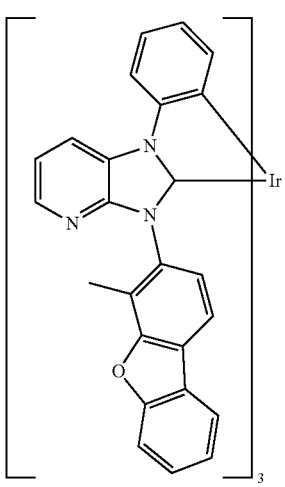

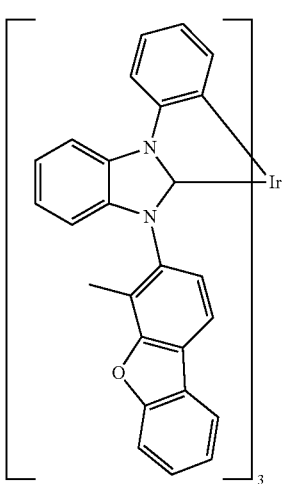

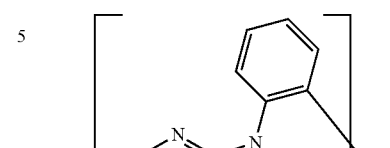

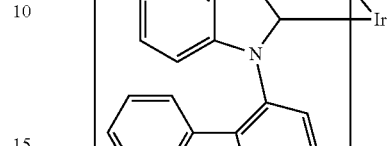

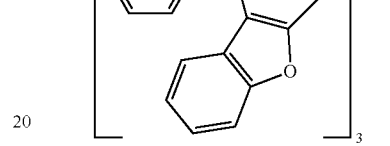

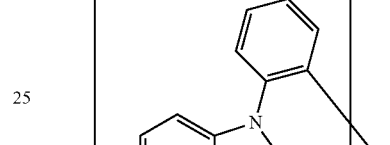

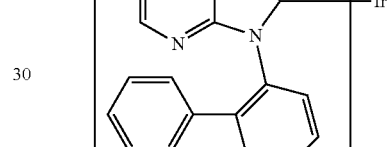

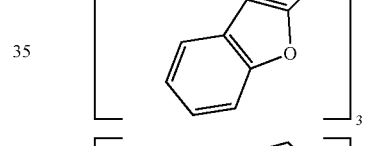

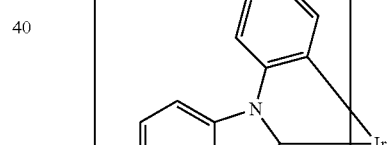

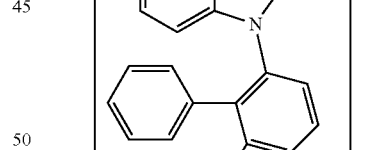

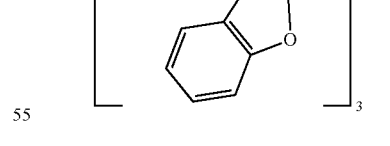

9. An organic electronic device comprising at least one cyclometallated Ir complex according to claim 1.

10. The organic electronic device according to claim 9, wherein the organic electronic device is selected from organic light-emitting diodes (OLED), light-emitting electrochemical cells (LEEC), organic photovoltaic cells (OPV) and organic field-effect transistors (OFET).

11. The organic electronic device according to claim 9, wherein the cyclometallated Ir complex of formula (I) is employed in OLEDs or LEECs or in OPVs.

12. The organic electronic device according to claim 11, wherein the OLED comprises
   (a) an anode,
   (b) a cathode,
   (c) a light-emitting layer between the anode and the cathode,
   (d) optionally a hole transport layer between the light-emitting layer and the anode,
   wherein the cyclometallated Ir complex of formula (I) is present in the light-emitting layer and/or—if present—in the hole transport layer of the OLED.

13. The organic electronic device according to claim 9, wherein the cyclometallated Ir complex of formula (I) is employed in combination with at least one host material.

14. A light-emitting layer comprising at least one cyclometallated Ir complex of formula (I) as defined in claim 1 as emitter.

15. An organic light-emitting diode (OLED) comprising a cyclometallated Ir complex of formula (I) as defined in claim 1.

16. An apparatus selected from the group consisting of stationary visual display units, such as visual display units of computers, televisions, visual display units in printers, kitchen appliances, advertising panels, information panels and illuminations; mobile visual display units such as visual display units in smartphones, cellphones, tablet computers, laptops, digital cameras, MP3-players, vehicles, keyboards and destination displays on buses and trains; illumination units; units in items of clothing; units in handbags, units in accessories, units in furniture and units in wallpaper, comprising the organic electronic device according to claim 9.

17. A cyclometallated Ir complex having one of the following formulae:

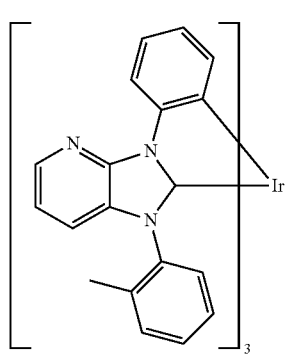

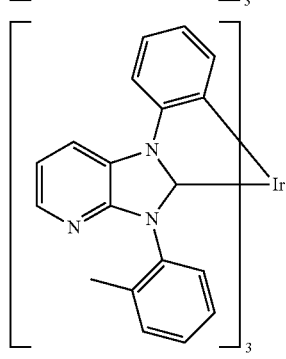

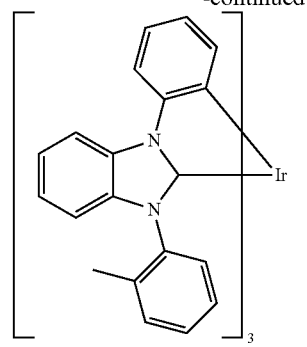

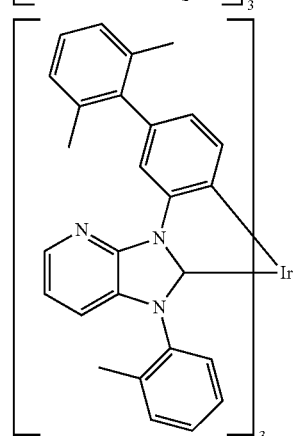

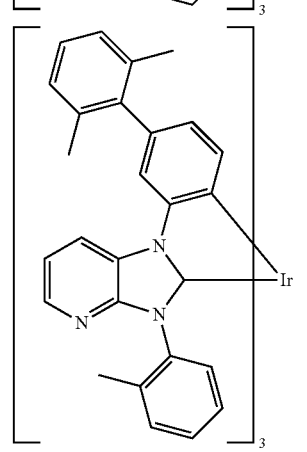

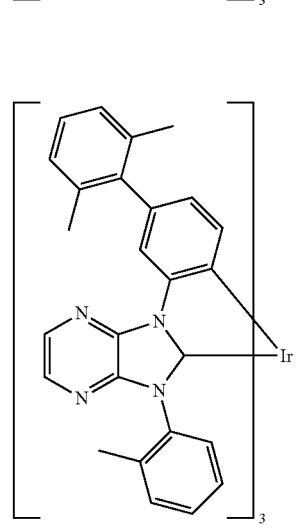

-continued
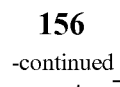
-continued
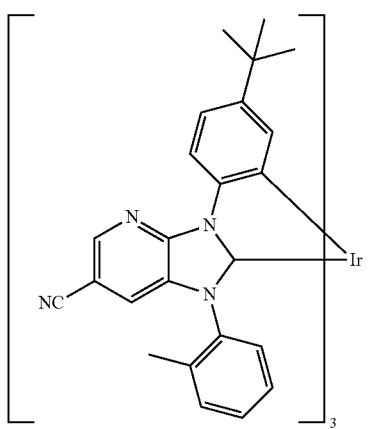
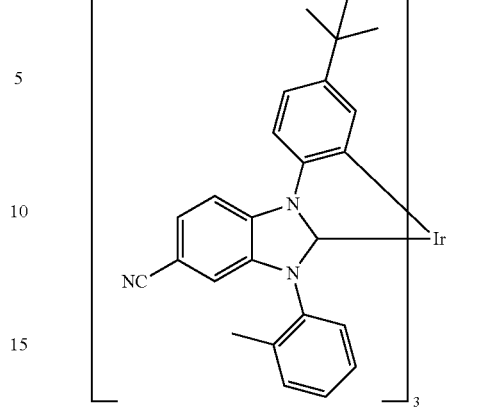
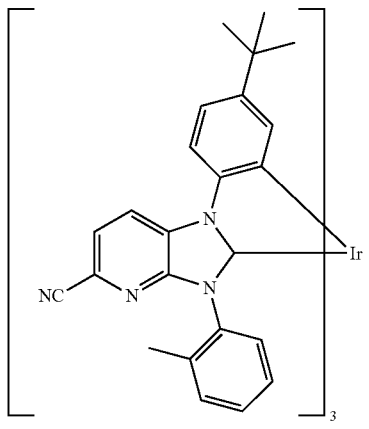
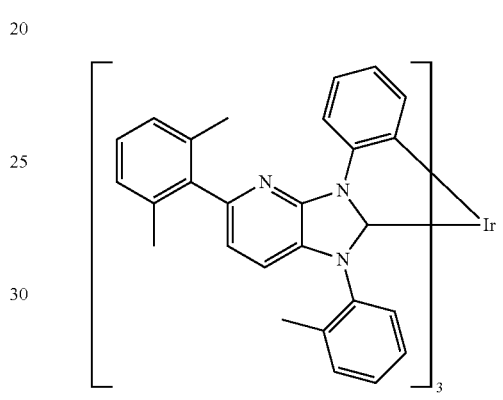
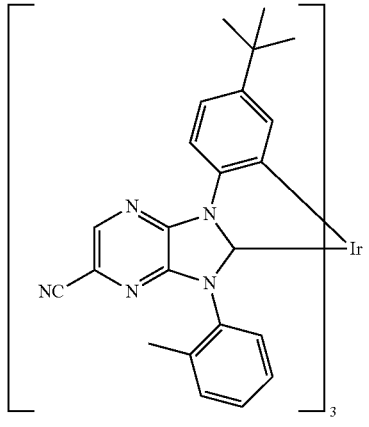
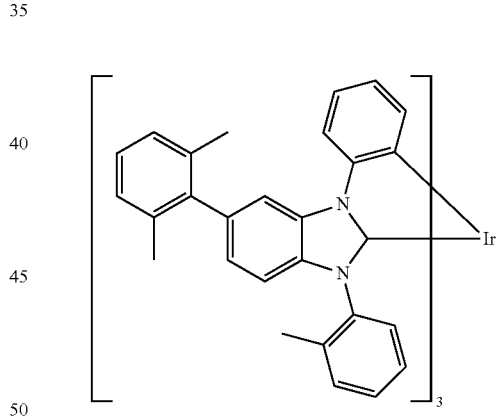
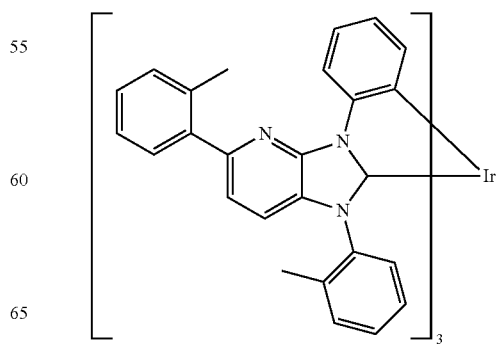

157
-continued
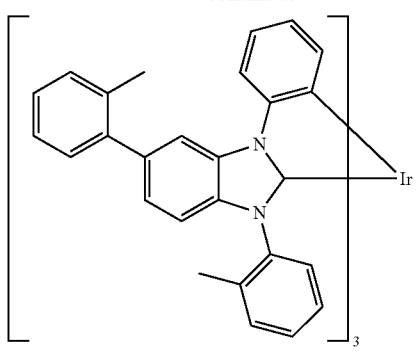
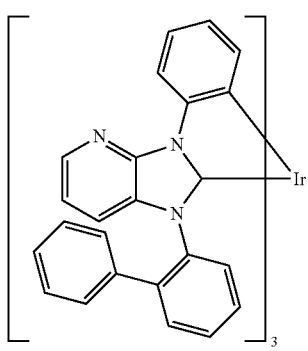
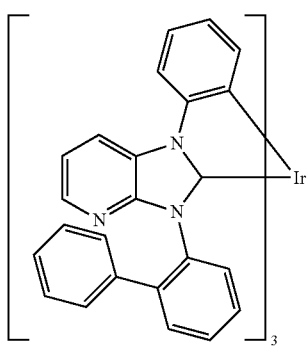
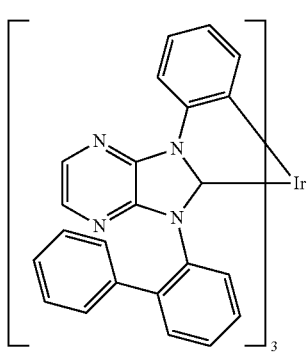
158
-continued
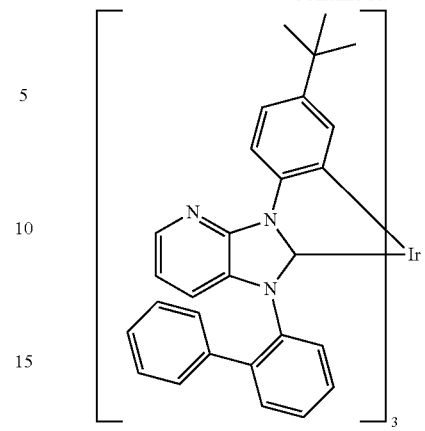
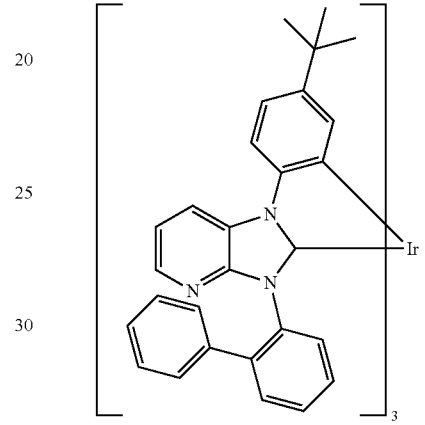
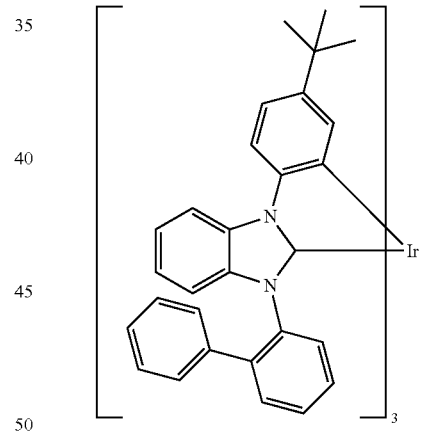
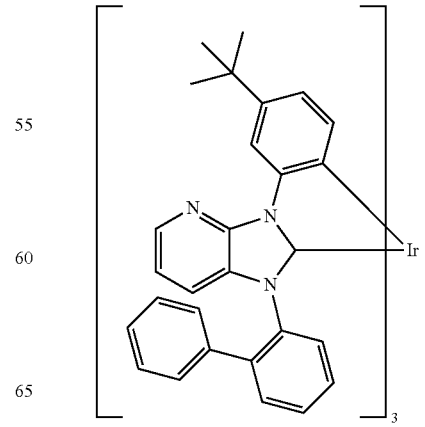

159
-continued
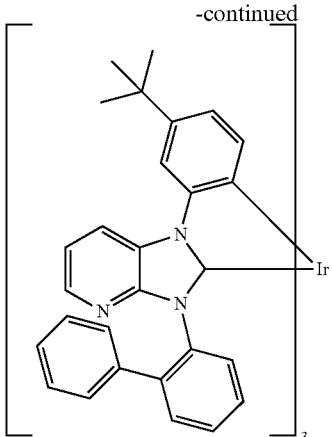
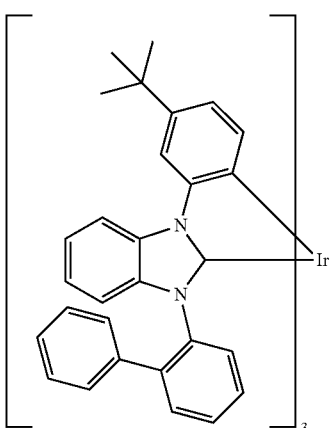
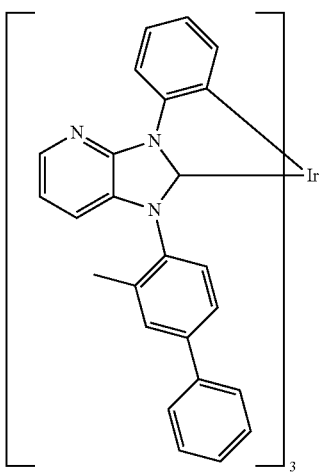
160
-continued
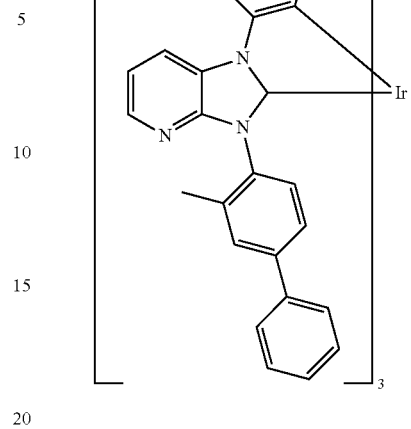
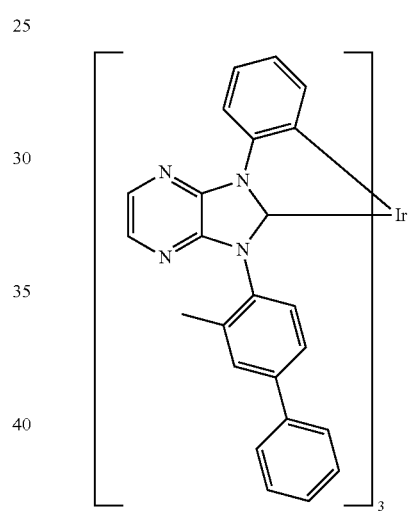
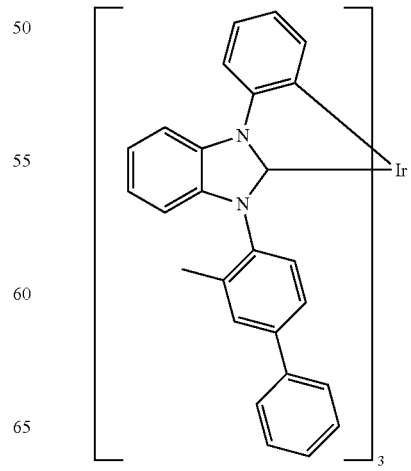

-continued
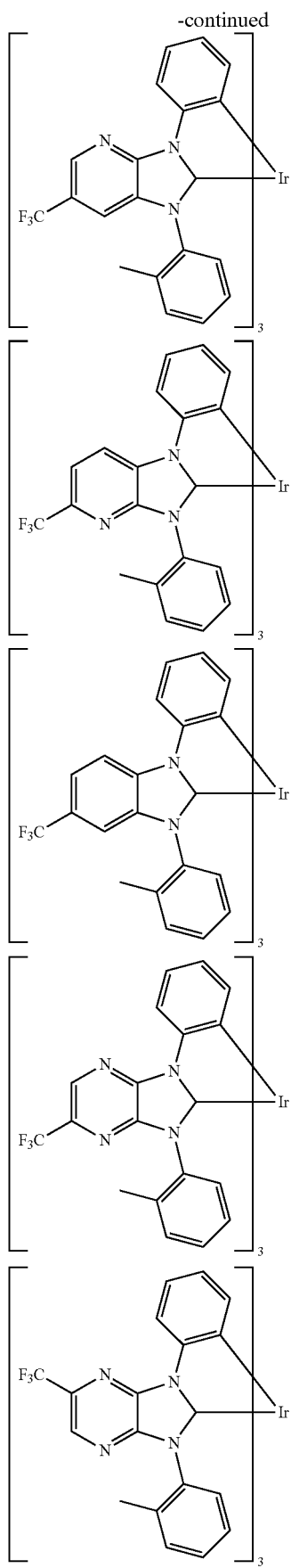
-continued
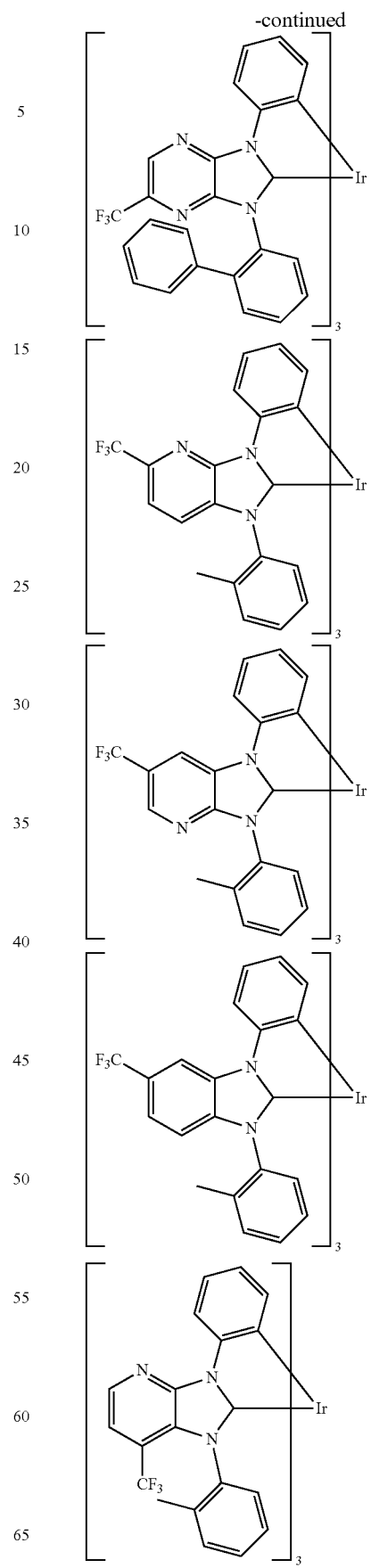

163
-continued
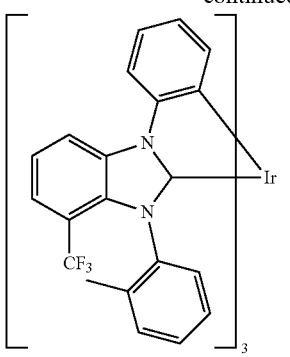
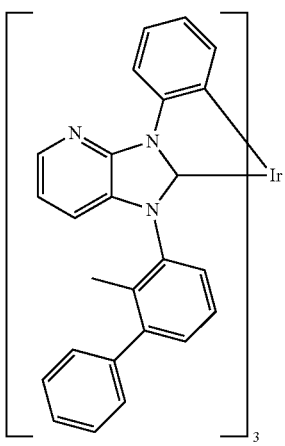
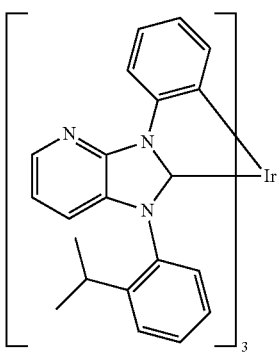
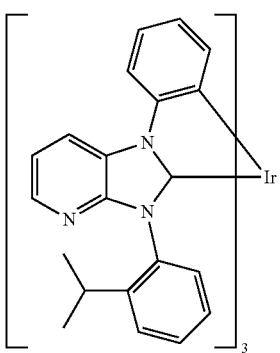
164
-continued
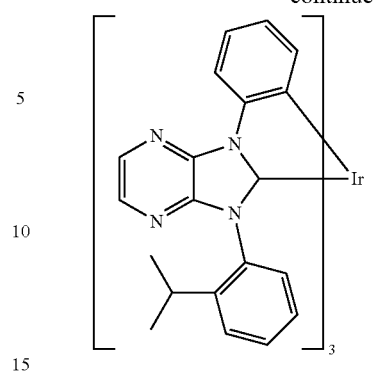
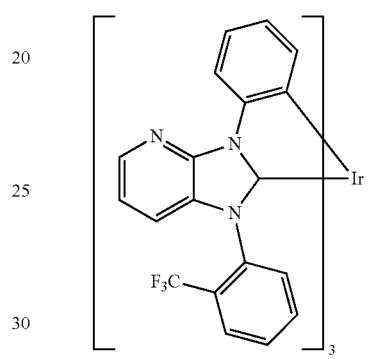
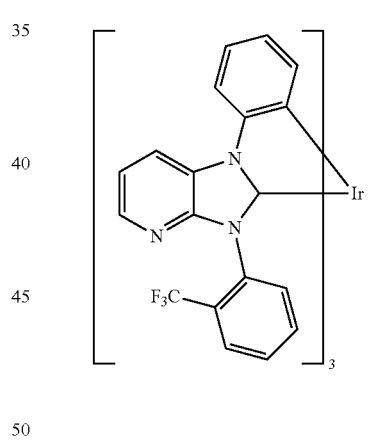
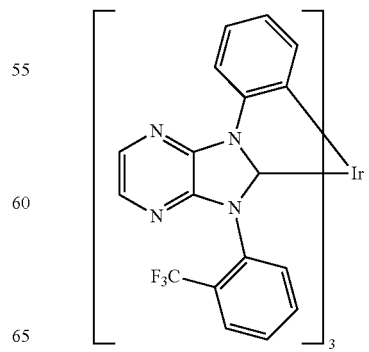

165
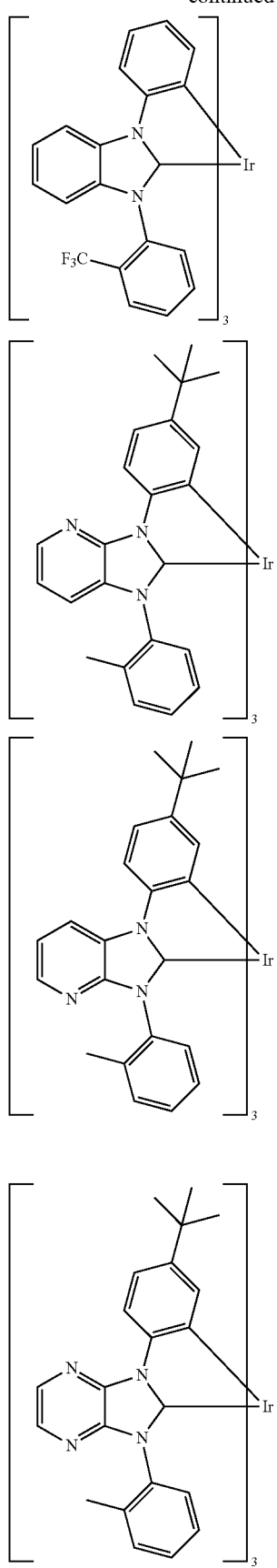
-continued
166
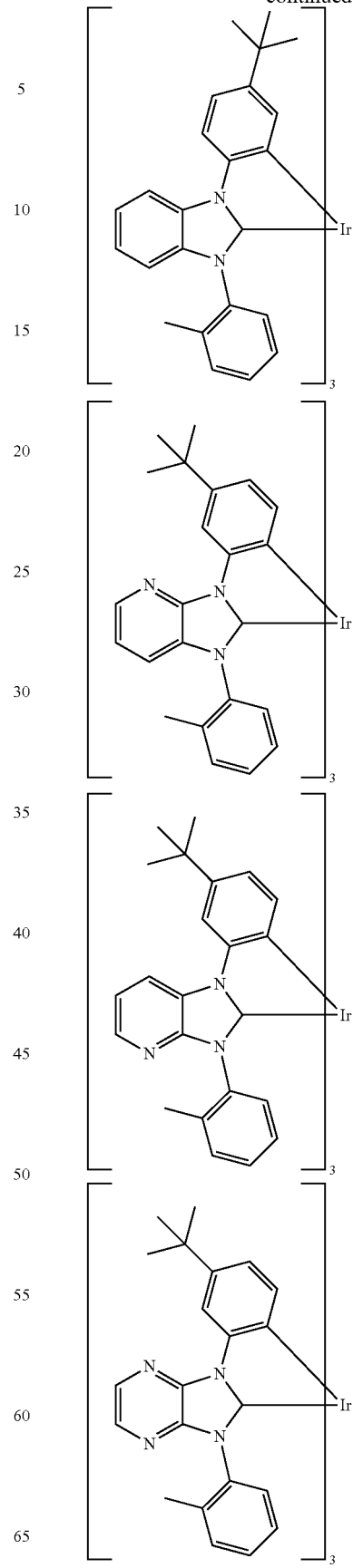
-continued

167
-continued
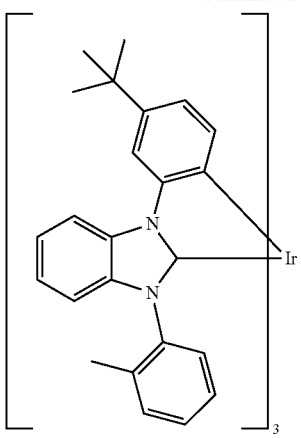
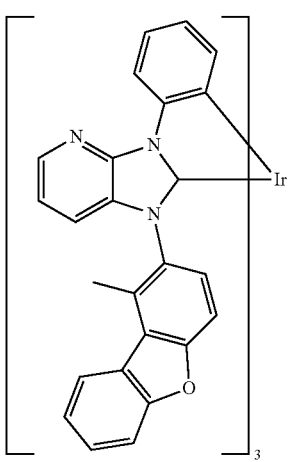
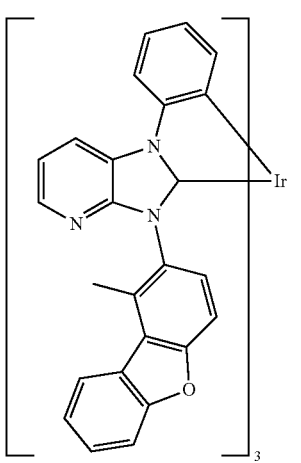
168
-continued
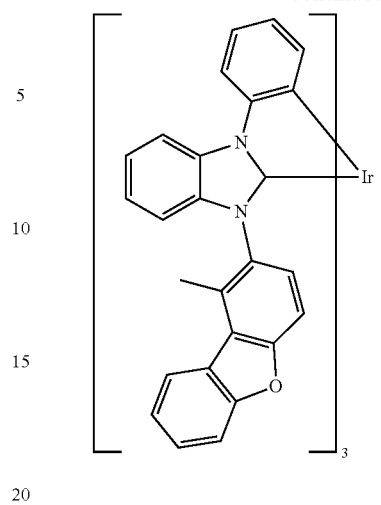
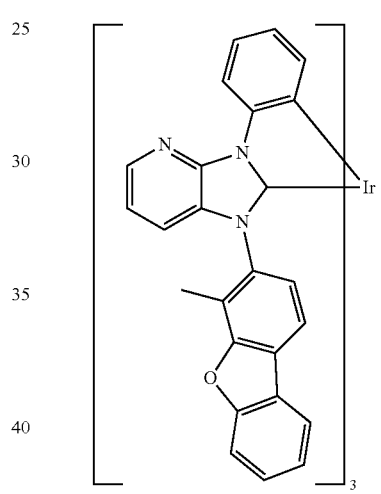
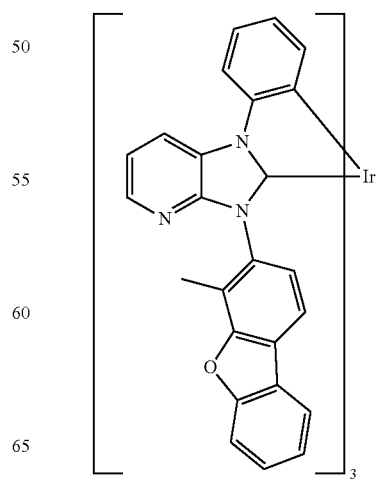

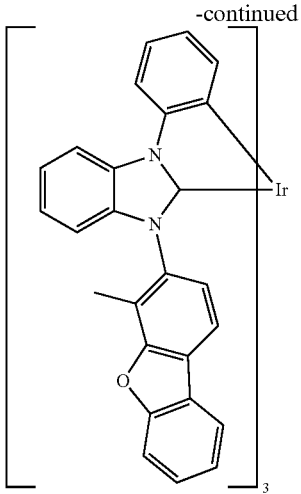
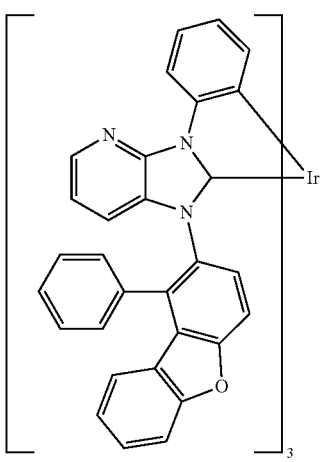
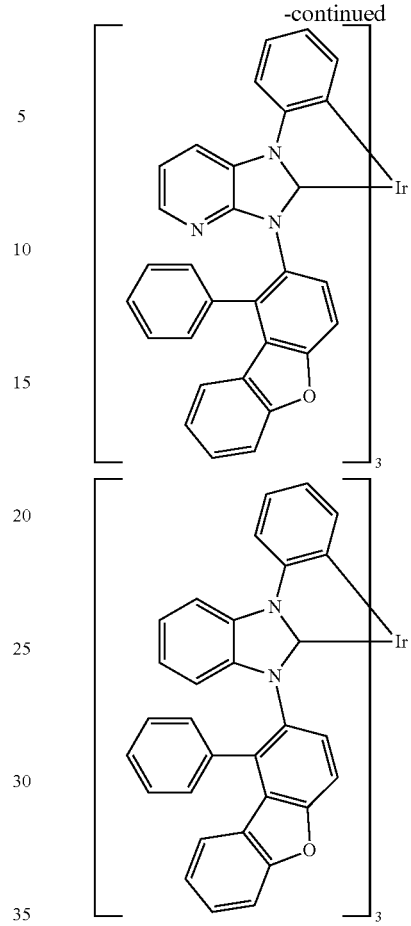
having an emission decay time $\tau_o$ of the luminescence emission of from 0.1 to 4 microseconds.
* * * * *